US012709747B2

(12) United States Patent
Duong et al.

(10) Patent No.: US 12,709,747 B2
(45) **Date of Patent: *Aug. 18, 2026**

(54) RAPID DESIGN, BUILD, TEST, AND LEARN TECHNOLOGIES FOR IDENTIFYING AND USING NON-VIRAL CARRIERS

(71) Applicant: BATTELLE MEMORIAL INSTITUTE, Columbus, OH (US)

(72) Inventors: Anthony D. Duong, Columbus, OH (US); Danielle J. Huk, Hilliard, OH (US); Cherry Gupta, Columbus, OH (US); Kenneth R. Sims, Jr., Delaware, OH (US); Michael S. Koeris, Irvine, CA (US); Zachary R. Shank, London, OH (US); Ashlee J. Colbert, Blacklick, OH (US); Andrea D. McCue, Columbus, OH (US); Emma K. Schmitz, Columbus, OH (US); Caleb T. Hillrich, Columbus, OH (US); Shannon D. Miller, Hilliard, OH (US); Joanna L. Hoy, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/475,879

(22) Filed: Sep. 27, 2023

(65) Prior Publication Data

US 2024/0117339 A1 Apr. 11, 2024

Related U.S. Application Data

(63) Continuation of application No. 17/715,784, filed on Apr. 7, 2022, now Pat. No. 12,031,128.

(60) Provisional application No. 63/172,069, filed on Apr. 7, 2021.

(51) Int. Cl.

| | |
|---|---|
| ***C12N 15/10*** | (2006.01) |
| ***A61K 48/00*** | (2006.01) |
| ***C12N 15/88*** | (2006.01) |
| *C12Q 1/6804* | (2018.01) |
| *C12Q 1/6816* | (2018.01) |
| *C12Q 1/682* | (2018.01) |
| *G01N 33/53* | (2006.01) |

(52) U.S. Cl.

CPC ...... *C12N 15/1065* (2013.01); *A61K 48/0041* (2013.01); *A61K 48/0091* (2013.01); *C12N 15/88* (2013.01); *C12Q 1/6804* (2013.01); *C12Q 1/6816* (2013.01); *C12Q 1/682* (2013.01); *C12Q 2525/301* (2013.01); *C12Q 2525/313* (2013.01); *G01N 33/5308* (2013.01)

(58) Field of Classification Search

CPC .......................... C12N 15/1065; C12N 15/88; A61K 48/0041; A61K 48/0091; C12Q 1/6816

See application file for complete search history.

(56) References Cited

U.S. PATENT DOCUMENTS

| | | | |
|---|---|---|---|
| 3,562,806 | A | 2/1971 | Grant et al. |
| 3,678,098 | A | 7/1972 | Lewis et al. |
| 3,691,123 | A | 9/1972 | Clarke et al. |
| 3,706,564 | A | 12/1972 | Perry et al. |
| 3,706,565 | A | 12/1972 | Harris |
| 3,739,042 | A | 6/1973 | Chu et al. |
| 3,744,969 | A | 7/1973 | Alps et al. |
| 3,829,564 | A | 8/1974 | Merry et al. |
| 3,847,857 | A | 11/1974 | Haag et al. |
| 4,036,766 | A | 7/1977 | Yamamoto et al. |
| 4,056,559 | A | 11/1977 | Lewis et al. |
| 4,219,616 | A | 8/1980 | Pope et al. |
| 4,237,253 | A | 12/1980 | Jacquet et al. |
| 4,377,481 | A | 3/1983 | Jakabhazy |
| 4,434,268 | A | 2/1984 | Doroszkowsky et al. |
| 4,544,621 | A | 10/1985 | Roth |
| 4,557,997 | A | 12/1985 | Iwasaki et al. |
| 4,559,293 | A | 12/1985 | Moriya et al. |
| 4,592,816 | A | 6/1986 | Emmons et al. |
| 4,595,722 | A | 6/1986 | Such |
| 4,656,027 | A | 4/1987 | Sjoovist |
| 4,735,887 | A | 4/1988 | Foss et al. |
| 4,755,563 | A | 7/1988 | West |
| 4,775,721 | A | 10/1988 | Horikawa et al. |
| 4,834,799 | A | 5/1989 | Song |
| 4,855,207 | A | 8/1989 | Tsubuko et al. |
| 4,925,764 | A | 5/1990 | Madeleine et al. |
| 4,985,160 | A | 1/1991 | Henry et al. |
| 5,085,698 | A | 2/1992 | Ma et al. |
| 5,124,381 | A | 6/1992 | Ward |
| 5,141,556 | A | 8/1992 | Matrick |
| 5,180,425 | A | 1/1993 | Matrick et al. |
| 5,205,861 | A | 4/1993 | Matrick |

(Continued)

FOREIGN PATENT DOCUMENTS

| | | |
|---|---|---|
| CN | 1323840 A | 11/2001 |
| CN | 1328106 A | 12/2001 |

(Continued)

OTHER PUBLICATIONS

Cheng C, Convertine AJ, Stayton PS, Bryers JD. Multifunctional triblock copolymers for intracellular messenger RNA delivery. Biomaterials. Oct. 2012;33(28):6868-76. doi: 10.1016/j.biomaterials.2012.06.020. Epub Jul. 9, 2012. PMID: 22784603; PMCID: PMC3412061.

(Continued)

*Primary Examiner* — Robert S Cabral
(74) *Attorney, Agent, or Firm* — Barnes & Thornburg

(57) ABSTRACT

The disclosure relates to barcoded polymer nanoparticles for in vivo screening and for in vivo therapeutic delivery, and methods therefor. More particularly, the invention relates to polymer nanoparticles, such as reversible addition-fragmentation chain transfer (RAFT) polymer compositions, associated with polynucleotide barcodes, for therapeutic delivery, and for high throughput in vivo screening of drug delivery nanoparticles.

18 Claims, 16 Drawing Sheets

Specification includes a Sequence Listing.

(56) References Cited

U.S. PATENT DOCUMENTS 5,271,765 A 12/1993 Ma
5,310,595 A 5/1994 Ali et al.
5,310,778 A 5/1994 Shor et al.
5,418,277 A 5/1995 Ma et al.
5,428,383 A 6/1995 Shields et al.
5,432,035 A 7/1995 Katagiri et al.
5,512,418 A 4/1996 Ma
5,518,534 A 5/1996 Pearlstine et al.
5,519,081 A 5/1996 Ashton et al.
5,519,085 A 5/1996 Ma et al.
5,525,450 A 6/1996 Spiewak et al.
5,620,883 A 4/1997 Shao et al.
5,698,016 A 12/1997 Adams et al.
5,709,714 A 1/1998 Natoli et al.
5,750,594 A 5/1998 Page et al.
5,969,046 A 10/1999 Schindler et al.
5,985,573 A 11/1999 Hennink et al.
6,004,582 A 12/1999 Faour et al.
6,004,712 A 12/1999 Barbetta et al.
6,022,533 A 2/2000 Goto et al.
6,022,908 A 2/2000 Ma et al.
6,040,358 A 3/2000 Page et al.
6,077,635 A 6/2000 Okado et al.
6,132,917 A 10/2000 Hoffend et al.
6,139,856 A 10/2000 Kaminska et al.
6,197,290 B1 3/2001 Goto et al.
6,207,631 B1 3/2001 Kasturi et al.
6,221,402 B1 4/2001 Itoh et al.
6,245,421 B1 6/2001 Aurenty et al.
6,247,808 B1 6/2001 Ma et al.
6,251,554 B1 6/2001 Hoffend et al.
6,276,273 B1 8/2001 Aurenty et al.
6,309,666 B1 10/2001 Hatano et al.
6,315,854 B1 11/2001 Anhauser et al.
6,372,708 B1 4/2002 Kasturi et al.
6,413,306 B1 7/2002 Kraiter et al.
6,471,349 B1 10/2002 Aurenty et al.
6,532,871 B1 3/2003 Aurenty et al.
6,624,210 B1 9/2003 Petereit et al.
6,692,769 B1 2/2004 Ishibashi et al.
6,720,387 B1 4/2004 Stark et al.
6,794,367 B1 9/2004 Tanida et al.
6,827,795 B1 12/2004 Kasturi et al.
6,903,064 B1 6/2005 Kasturi et al.
7,256,020 B2 8/2007 Lyamichev et al.
7,737,108 B1 6/2010 Hoffman et al.
8,758,860 B1 6/2014 Pyles et al.
9,085,618 B2 7/2015 Ramasubramanyan et al.
9,447,220 B2 9/2016 Cho et al.
9,644,204 B2 5/2017 Hindson
9,714,940 B2 7/2017 Lowery, Jr. et al.
9,850,482 B2 12/2017 Kwon
9,970,040 B2 5/2018 Elbaz et al.
10,201,503 B1 2/2019 Li et al.
10,695,443 B2 6/2020 Lötvall et al.
11,419,932 B2 8/2022 Bathe et al.
2002/0028410 A1 3/2002 Choi
2002/0187311 A1 12/2002 Golub et al.
2003/0049311 A1 3/2003 McAllister et al.
2003/0064036 A1 4/2003 Petereit et al.
2003/0071883 A1 4/2003 Suzuki et al.
2003/0106160 A1 6/2003 Sun et al.
2003/0124074 A1 7/2003 Mougin et al.
2003/0130160 A1 7/2003 Eason et al.
2003/0152856 A1 8/2003 Mizoe et al.
2003/0199419 A1 10/2003 Rodrigues et al.
2004/0091538 A1 5/2004 Pollock-Dove et al.
2004/0096490 A1 5/2004 Bracht et al.
2004/0104501 A1 6/2004 Petereit et al.
2004/0109869 A1 6/2004 Glenn et al.
2004/0198838 A1 10/2004 Alles et al.
2004/0208925 A1 10/2004 Oner et al.
2004/0219211 A1 11/2004 Criere et al.
2004/0249035 A1 12/2004 Petereit et al.
2005/0020779 A1 1/2005 Mougin et al.
2005/0026803 A1 2/2005 Sivik et al.
2005/0048112 A1 3/2005 Breitenbach et al.
2005/0053566 A1 3/2005 Nguyen-Kim et al.
2005/0070486 A1 3/2005 Wieland-Berghausen et al.
2005/0084529 A1 4/2005 Rosenberg et al.
2005/0090599 A1 4/2005 Spinelli
2005/0208133 A1 9/2005 Tsutsumi et al.
2005/0281871 A1 12/2005 Petereit et al.
2006/0051412 A1 3/2006 Petereit et al.
2006/0089425 A1 4/2006 Chopra et al.
2006/0110433 A1 5/2006 Terahara et al.
2006/0257484 A1 11/2006 Hwang et al.
2006/0280798 A1 12/2006 Ensoli
2007/0027213 A1 2/2007 Oberegger et al.
2007/0072996 A1 3/2007 Kedar et al.
2007/0088118 A1 4/2007 Dungworth et al.
2007/0141013 A1 6/2007 Nguyen-Kim et al.
2007/0178059 A1 8/2007 Moser et al.
2007/0203245 A1 8/2007 Koltun et al.
2007/0231397 A1 10/2007 Petereit et al.
2007/0259028 A1 11/2007 Ito
2007/0275060 A1 11/2007 Befumo et al.
2007/0275071 A1 11/2007 Ensoli et al.
2008/0050432 A1 2/2008 Jun et al.
2008/0050450 A1 2/2008 Arnold et al.
2008/0075689 A1 3/2008 Pierobon et al.
2008/0089853 A1 4/2008 Nguyen-Kim et al.
2008/0153982 A1 6/2008 Lai et al.
2008/0181948 A1 7/2008 Berndl et al.
2008/0193405 A1 8/2008 Mukherjee et al.
2008/0193544 A1 8/2008 Bruck-Scheffler et al.
2008/0226731 A1 9/2008 Vasanthavada et al.
2008/0233177 A1 9/2008 Meconi
2008/0280999 A1 11/2008 Lakshman
2008/0286221 A1 11/2008 Kim et al.
2008/0299391 A1 12/2008 White et al.
2008/0306233 A1 12/2008 Muhrer et al.
2009/0023754 A1 1/2009 Lee et al.
2009/0053315 A1 2/2009 Brough et al.
2009/0099075 A1 4/2009 Barg et al.
2009/0108241 A1 4/2009 Ogura et al.
2009/0118399 A1 5/2009 Benbakoura et al.
2009/0148522 A1 6/2009 Kowalski et al.
2009/0161058 A1 6/2009 Sherman
2009/0175952 A1 7/2009 Woo et al.
2009/0220596 A1 9/2009 Rosenberg et al.
2009/0221621 A1 9/2009 Sathyan et al.
2009/0280183 A1 11/2009 Lizio et al.
2009/0285891 A1 11/2009 Jung et al.
2009/0302493 A1 12/2009 Kessler et al.
2009/0311320 A1 12/2009 Oury et al.
2009/0318847 A1 12/2009 Sebree et al.
2009/0321945 A1 12/2009 Besling
2010/0038816 A1 2/2010 Ghogh et al.
2010/0048737 A1 2/2010 Wendel et al.
2010/0074951 A1 3/2010 Kim et al.
2010/0087544 A1 4/2010 Kim et al.
2010/0120970 A1 5/2010 Biggs et al.
2010/0143459 A1 6/2010 Liepold et al.
2010/0143470 A1 6/2010 Kim et al.
2010/0143590 A1 6/2010 Held et al.
2010/0152299 A1 6/2010 Vasanthavada et al.
2010/0160183 A1 6/2010 Xu et al.
2010/0174040 A1 7/2010 Kim et al.
2010/0209480 A1 8/2010 Altenburger et al.
2010/0209520 A1 8/2010 Kubo
2010/0233350 A1 9/2010 Herrmann
2010/0233447 A1 9/2010 Campbell
2010/0247635 A1 9/2010 Rosenberg et al.
2010/0266859 A1 10/2010 Abe et al.
2010/0272797 A1 10/2010 Kim et al.
2010/0278899 A1 11/2010 Sugiura et al.
2010/0286288 A1 11/2010 Langguth et al.
2010/0291311 A1 11/2010 Trouve et al.
2010/0310644 A1 12/2010 Liebmann et al.
2010/0323090 A1 12/2010 Ishizaki et al.
2011/0002988 A1 1/2011 Ishizaki et al.
2011/0005773 A1 1/2011 Dusterhoft et al.
2011/0032303 A1 2/2011 Li

(56) References Cited

U.S. PATENT DOCUMENTS

2011/0052683 A1 3/2011 Kim et al.
2011/0052699 A1 3/2011 Funke et al.
2011/0091563 A1 4/2011 Kurasawa et al.
2011/0111021 A1 5/2011 Kim et al.
2011/0111022 A1 5/2011 Kim et al.
2011/0117194 A1 5/2011 Kim et al.
2011/0123636 A1 5/2011 Stayton et al.
2011/0143435 A1 6/2011 Stayton
2011/0144260 A1 6/2011 Tanabe et al.
2011/0201759 A1 8/2011 Takahashi
2011/0242154 A1 10/2011 Roberts et al.
2011/0257289 A1 10/2011 Biggs et al.
2011/0263470 A1 10/2011 Qin et al.
2011/0269913 A1 11/2011 Balk et al.
2011/0274893 A1 11/2011 Kaser et al.
2011/0275775 A1 11/2011 Goto et al.
2011/0287100 A1 11/2011 Desset-Brethes et al.
2011/0305660 A1 12/2011 Stayton et al.
2011/0306632 A1 12/2011 Miller et al.
2011/0312973 A1 12/2011 Liepold et al.
2012/0009223 A1 1/2012 Wenguang et al.
2012/0021514 A1 1/2012 Johnson
2012/0053248 A1 3/2012 Kolter et al.
2012/0093982 A1 4/2012 Tsukioka et al.
2012/0143039 A1 6/2012 Hartwig et al.
2012/0172574 A1 7/2012 Helou et al.
2012/0183769 A1 7/2012 Nasu et al.
2012/0190724 A1 7/2012 Na et al.
2012/0213827 A1 8/2012 Chatterji et al.
2012/0220550 A1 8/2012 Bae et al.
2012/0232117 A1 9/2012 Bae et al.
2012/0251583 A1 10/2012 Rothemund
2012/0258909 A1 10/2012 Liepold et al.
2012/0282303 A1 11/2012 Ito
2012/0282310 A1 11/2012 Lucet-Levannier et al.
2012/0283670 A1 11/2012 Ito
2012/0323190 A1 12/2012 Ito
2012/0328891 A1 12/2012 Suwa et al.
2013/0005874 A1 1/2013 Nakajima et al.
2013/0011362 A1 1/2013 Monahan et al.
2013/0017245 A1 1/2013 Takano
2013/0034599 A1 2/2013 Thaxton et al.
2013/0040236 A1 2/2013 Fukushima et al.
2013/0085233 A1 4/2013 Niitani et al.
2013/0090480 A1 4/2013 Park Choo et al.
2013/0095168 A1 4/2013 Choi et al.
2013/0129869 A1 5/2013 Hafezi et al.
2013/0171646 A1 7/2013 Park et al.
2013/0172239 A1 7/2013 Gao et al.
2013/0214832 A1 8/2013 Palwai
2013/0224859 A1 8/2013 Bachelet et al.
2013/0236551 A1 9/2013 Cavazza
2013/0239339 A1 9/2013 Bown et al.
2013/0243873 A1 9/2013 Aversa et al.
2013/0261019 A1 10/2013 Lin et al.
2013/0274297 A1 10/2013 Gatti et al.
2013/0317096 A1 11/2013 Yap et al.
2014/0018404 A1 1/2014 Chen et al.
2014/0080868 A1 3/2014 Ng et al.
2014/0080869 A1 3/2014 Krishnan et al.
2014/0080886 A1 3/2014 Pilot-Matias et al.
2014/0088152 A1 3/2014 Bae et al.
2014/0128418 A1 5/2014 Bae et al.
2014/0128827 A1 5/2014 Song
2014/0155388 A1 6/2014 Brzeczko et al.
2014/0161893 A1 6/2014 Shen et al.
2014/0206742 A1 7/2014 Lomuscio et al.
2014/0235790 A1 8/2014 Stayton et al.
2014/0248350 A1 9/2014 Reyes et al.
2014/0271857 A1 9/2014 Nelson et al.
2014/0303334 A1 10/2014 Goto et al.
2015/0045353 A1 2/2015 Comer et al.
2015/0086624 A1 3/2015 Cho et al.
2015/0104408 A1 4/2015 Wakefield et al.
2015/0118294 A1 4/2015 Song et al.
2015/0132479 A1 5/2015 Arfsten et al.
2015/0164816 A1 6/2015 Jaklenec et al.
2015/0174250 A1 6/2015 Griffiths et al.
2015/0191132 A1 7/2015 Muramoto et al.
2015/0218125 A1 8/2015 Bae et al.
2015/0232729 A1 8/2015 Zhao et al.
2015/0258093 A1 9/2015 Miller et al.
2015/0283254 A1 10/2015 Duvall et al.
2015/0297526 A1 10/2015 Puniya et al.
2015/0374634 A1 12/2015 Koo et al.
2016/0045446 A1 2/2016 Shibata et al.
2016/0151498 A1 6/2016 Trieu
2016/0187323 A1 6/2016 Farokhzad et al.
2016/0193246 A1 7/2016 Grandfils et al.
2016/0194368 A1 7/2016 Hoge et al.
2016/0194625 A1 7/2016 Hoge et al.
2016/0220472 A1 8/2016 Wang et al.
2016/0243221 A1 8/2016 Hoge et al.
2016/0243274 A1 8/2016 Chisholm et al.
2016/0244501 A1 8/2016 Ellsworth et al.
2016/0244502 A1 8/2016 Bolen et al.
2016/0250170 A1 9/2016 Hsu et al.
2016/0279251 A1 9/2016 Stayton et al.
2016/0279289 A1 9/2016 Chisholm et al.
2016/0313566 A1 10/2016 Le et al.
2016/0317445 A1 11/2016 Saly et al.
2016/0317647 A1 11/2016 Ciaramella et al.
2016/0375017 A1 12/2016 Asmus et al.
2016/0375143 A1 12/2016 Gunatillake
2016/0376333 A1 12/2016 Procko et al.
2017/0002060 A1 1/2017 Bolen et al.
2017/0079932 A1 3/2017 Emgenbroich et al.
2017/0087174 A1 3/2017 Beumont et al.
2017/0105945 A1 4/2017 Emgenbroich et al.
2017/0119690 A1 5/2017 Hansen et al.
2017/0128380 A1 5/2017 Wang
2017/0173128 A1 6/2017 Hoge et al.
2017/0211023 A1 7/2017 Zhang
2017/0231989 A1 8/2017 Hayashi et al.
2017/0240765 A1 8/2017 Nabuurs et al.
2017/0247381 A1 8/2017 Mao et al.
2017/0296484 A1 10/2017 Kottayil et al.
2017/0304213 A1 10/2017 Shi et al.
2017/0327463 A1 11/2017 Fung et al.
2018/0031971 A1 2/2018 Hustad et al.
2018/0031972 A1 2/2018 Hustad et al.
2018/0200190 A1 7/2018 Dharmadhikari et al.
2018/0221295 A1 8/2018 Hansen et al.
2018/0221300 A1 8/2018 Emgenbroich et al.
2018/0221402 A1 8/2018 Prieve et al.
2018/0230489 A1 8/2018 Kotin
2018/0237800 A1 8/2018 Murthy et al.
2018/0318365 A1 11/2018 Yeung et al.
2018/0333683 A1 11/2018 Liu et al.
2018/0346797 A1 12/2018 Kalgaonkar et al.
2019/0000765 A1 1/2019 Hattori et al.
2019/0054069 A1 2/2019 Chen et al.
2019/0060425 A1 2/2019 Scheel et al.
2019/0070143 A1 3/2019 Boulas et al.
2019/0070233 A1 3/2019 Yeung et al.
2019/0077923 A1 3/2019 Beaume et al.
2019/0091339 A1 3/2019 Miller et al.
2019/0099381 A1 4/2019 Gong et al.
2019/0125663 A1 5/2019 Herry et al.
2019/0153471 A1 5/2019 Paul et al.
2019/0192691 A1 6/2019 Barrett et al.
2019/0194376 A1 6/2019 Maejima et al.
2019/0203030 A1 7/2019 Cheong et al.
2019/0224339 A1 7/2019 Paul et al.
2019/0231712 A1 8/2019 Matsumoto et al.
2019/0247350 A1 8/2019 Mizugaki et al.
2019/0254966 A1 8/2019 Bellinger et al.
2019/0270991 A1 9/2019 Foot et al.
2019/0274346 A1 9/2019 Gore et al.
2019/0358341 A1 11/2019 Adams
2019/0365773 A1 12/2019 Yokoyama et al.
2019/0376120 A1 12/2019 Strauss
2019/0382837 A1 12/2019 Spurbeck et al.
2020/0016092 A1 1/2020 Bernardo et al.

(56) References Cited

U.S. PATENT DOCUMENTS

| | | | |
|---|---|---|---|
| 2020/0038390 | A1 | 2/2020 | Park et al. |
| 2020/0051813 | A1 | 2/2020 | Osaki et al. |
| 2020/0069696 | A1 | 3/2020 | Liu |
| 2020/0078463 | A1 | 3/2020 | Park et al. |
| 2020/0086616 | A1 | 3/2020 | Meise et al. |
| 2020/0123391 | A1 | 4/2020 | Habets et al. |
| 2020/0129440 | A1 | 4/2020 | Baek et al. |
| 2020/0138072 | A1 | 5/2020 | Yucel et al. |
| 2020/0163962 | A1 | 5/2020 | Jahagirdar et al. |
| 2020/0165630 | A1 | 5/2020 | Paul et al. |
| 2020/0171169 | A1 | 6/2020 | Duvall et al. |
| 2020/0188290 | A1 | 6/2020 | Herrmann et al. |
| 2020/0197289 | A1 | 6/2020 | Wang et al. |
| 2020/0206133 | A1 | 7/2020 | Alsenz et al. |
| 2020/0224022 | A1 | 7/2020 | Gigmes et al. |
| 2020/0261426 | A1 | 8/2020 | Park et al. |
| 2020/0308331 | A1 | 10/2020 | Kang et al. |
| 2020/0390752 | A1 | 12/2020 | Moon et al. |
| 2021/0054436 | A1 * | 2/2021 | Lam .................... C12Q 1/6869 |
| 2021/0069111 | A1 | 3/2021 | Reineke et al. |
| 2021/0128479 | A1 | 5/2021 | Cheng et al. |
| 2021/0163933 | A1 | 6/2021 | Budnik et al. |
| 2021/0163985 | A1 | 6/2021 | Sah et al. |
| 2021/0196682 | A1 | 7/2021 | Chen et al. |
| 2021/0213002 | A1 | 7/2021 | Natori et al. |
| 2021/0330599 | A1 | 10/2021 | Benoit et al. |
| 2021/0347950 | A1 | 11/2021 | Kou et al. |
| 2021/0355454 | A1 | 11/2021 | Cardinal et al. |
| 2021/0371470 | A1 | 12/2021 | Murlidharan et al. |
| 2021/0373002 | A1 | 12/2021 | Gopinath et al. |
| 2021/0387156 | A1 | 12/2021 | Oschmann et al. |
| 2021/0387946 | A1 | 12/2021 | Lindemann et al. |
| 2022/0008346 | A1 | 1/2022 | Wilson et al. |
| 2022/0016098 | A1 | 1/2022 | Cho et al. |
| 2022/0016271 | A1 | 1/2022 | Farokhzad et al. |
| 2022/0025428 | A1 | 1/2022 | Hughes |
| 2022/0031607 | A1 | 2/2022 | Cho et al. |
| 2022/0143062 | A1 | 5/2022 | Kahvejian et al. |
| 2022/0175812 | A1 | 6/2022 | Duong et al. |
| 2022/0227778 | A1 | 7/2022 | Wang |
| 2022/0233514 | A1 | 7/2022 | Choi et al. |
| 2022/0233580 | A1 | 7/2022 | Takeshita et al. |
| 2022/0243225 | A1 | 8/2022 | Mathur et al. |
| 2022/0291432 | A1 | 9/2022 | O'Keeffe |
| 2022/0333097 | A1 | 10/2022 | Duong et al. |
| 2022/0396789 | A1 | 12/2022 | Banal et al. |
| 2023/0059080 | A1 | 2/2023 | Lee et al. |
| 2023/0067461 | A1 | 3/2023 | Lee et al. |
| 2023/0092431 | A1 | 3/2023 | Isabella et al. |
| 2023/0218536 | A1 | 7/2023 | Solomun et al. |
| 2023/0227687 | A1 | 7/2023 | Li et al. |
| 2023/0310621 | A1 | 10/2023 | Grandfils et al. |
| 2024/0067960 | A1 | 2/2024 | Gupta et al. |
| 2024/0074981 | A1 | 3/2024 | Gupta et al. |
| 2025/0108013 | A1 | 4/2025 | Duong |
| 2025/0108125 | A1 | 4/2025 | Sims, Jr. |
| 2025/0109235 | A1 | 4/2025 | Gupta |
| 2025/0188449 | A1 | 6/2025 | Gupta |
| 2025/0367133 | A1 | 12/2025 | Colbert |
| 2026/0014186 | A1 | 1/2026 | Duong |

FOREIGN PATENT DOCUMENTS

| | | | |
|---|---|---|---|
| CN | 1806901 | A | 7/2006 |
| CN | 1813683 | A | 8/2006 |
| CN | 1896112 | A | 1/2007 |
| CN | 101444513 | A | 6/2009 |
| CN | 101643412 | A | 2/2010 |
| CN | 101735383 | A | 6/2010 |
| CN | 102030871 | A | 4/2011 |
| CN | 102250278 | A | 11/2011 |
| CN | 102949342 | A | 3/2013 |
| CN | 103113509 | A | 5/2013 |
| CN | 103255174 | A | 8/2013 |
| CN | 103319668 | A | 9/2013 |
| CN | 103333283 | A | 10/2013 |
| CN | 103536972 | A | 1/2014 |
| CN | 103755870 | A | 4/2014 |
| CN | 103976972 | A | 8/2014 |
| CN | 104479064 | A | 4/2015 |
| CN | 104772051 | A | 7/2015 |
| CN | 104784155 | A | 7/2015 |
| CN | 104922078 | A | 9/2015 |
| CN | 104971073 | A | 10/2015 |
| CN | 105504923 | A | 4/2016 |
| CN | 105833272 | A | 8/2016 |
| CN | 105833287 | A | 8/2016 |
| CN | 105949365 | A | 9/2016 |
| CN | 106117580 | A | 11/2016 |
| CN | 106236785 | A | 12/2016 |
| CN | 106478904 | A | 3/2017 |
| CN | 106811998 | A | 6/2017 |
| CN | 107173546 | A | 9/2017 |
| CN | 107596368 | A | 1/2018 |
| CN | 109422960 | A | 3/2019 |
| CN | 115714187 | A | 2/2023 |
| DE | 2446449 | A1 | 4/1975 |
| EP | 0217137 | A2 | 4/1987 |
| EP | 0587333 | A2 | 3/1994 |
| EP | 0597577 | A1 | 5/1994 |
| EP | 0945148 | A1 | 9/1999 |
| EP | 1008634 | A1 | 6/2000 |
| GB | 1284489 | A | 8/1972 |
| GB | 1314285 | A | 4/1973 |
| GB | 1324087 | A | 7/1973 |
| IN | 2012MU01581 | A | 1/2014 |
| IN | 2014KO01127 | A | 5/2016 |
| IN | 201611026597 | A | 3/2018 |
| IN | 201921005566 | A | 8/2020 |
| JP | S5156886 | A | 5/1976 |
| JP | S51100129 | A | 9/1976 |
| JP | H01229014 | A | 9/1989 |
| JP | 2003345095 | A | 12/2003 |
| JP | 2008274217 | A | 11/2008 |
| JP | 2008274218 | A | 11/2008 |
| JP | 2008274219 | A | 11/2008 |
| JP | 2009016258 | A | 1/2009 |
| JP | 2010111781 | A | 5/2010 |
| JP | 2011074250 | A | 4/2011 |
| JP | 2011207963 | A | 10/2011 |
| JP | 2013029832 | A | 2/2013 |
| JP | 2013114184 | A | 6/2013 |
| JP | 2013203887 | | 10/2013 |
| JP | 2013237821 | A | 11/2013 |
| JP | 2016065115 | A | 4/2016 |
| JP | 2016126154 | A | 7/2016 |
| JP | 2017058405 | A | 3/2017 |
| JP | 2018154752 | A | 10/2018 |
| JP | 2018174919 | A | 11/2018 |
| JP | 2018203987 | A | 12/2018 |
| JP | 2019127444 | A | 8/2019 |
| JP | 2020074704 | A | 5/2020 |
| JP | 2022057447 | A | 4/2022 |
| JP | 2022076360 | A | 5/2022 |
| JP | 2022117407 | A | 8/2022 |
| KR | 830000972 | A | 4/1983 |
| KR | 20020016069 | A | 3/2002 |
| KR | 20030078118 | A | 10/2003 |
| KR | 20050023239 | A | 3/2005 |
| KR | 20080002313 | A | 1/2008 |
| KR | 20080008769 | A | 1/2008 |
| KR | 100867639 | B1 | 11/2008 |
| KR | 20080097787 | A | 11/2008 |
| KR | 20090114190 | A | 11/2009 |
| KR | 100994148 | B1 | 11/2010 |
| KR | 20110043347 | A | 4/2011 |
| KR | 20110117758 | A | 10/2011 |
| KR | 20110119542 | A | 11/2011 |
| KR | 20110135018 | A | 12/2011 |
| KR | 20120047345 | A | 5/2012 |
| KR | 20120134329 | A | 12/2012 |
| KR | 20120134605 | A | 12/2012 |
| KR | 20130010708 | A | 1/2013 |
| KR | 20130013157 | A | 2/2013 |

(56) References Cited

FOREIGN PATENT DOCUMENTS

KR 20130027822 A 3/2013
KR 20130030907 A 3/2013
KR 101312286 B1 9/2013
KR 20140095767 A 8/2014
KR 20140105941 A 9/2014
KR 101458468 B1 11/2014
KR 20140130579 A 11/2014
KR 20150105043 A 9/2015
KR 20170076494 A 7/2017
KR 101827744 B1 2/2018
KR 20180029147 A 3/2018
KR 101850629 B1 4/2018
KR 20180099263 A 9/2018
KR 101923028 B1 11/2018
KR 101943270 B1 1/2019
KR 20190111448 A 10/2019
KR 102107332 B1 5/2020
KR 102157964 B1 9/2020
KR 20200123022 A 10/2020
KR 102207353 B1 1/2021
KR 102207354 B1 1/2021
KR 102212503 B1 2/2021
KR 102212504 B1 2/2021
KR 102212505 B1 2/2021
KR 20210122720 A 10/2021
PL 440443 A1 8/2023
RU 2582704 C1 4/2016
TW 201204713 A 2/2012
TW 201404805 A 2/2014
WO WO-1991013145 A1 9/1991
WO WO-1998051749 A1 11/1998
WO 03/090780 A1 6/2003
WO 2004090004 A1 10/2004
WO WO-2004096422 A1 11/2004
WO WO-2007060462 A1 5/2007
WO WO-2008005543 A2 1/2008
WO WO-2007078765 A3 4/2008
WO WO-2008050987 A1 5/2008
WO WO-2009038340 A1 3/2009
WO WO-2009088220 A2 7/2009
WO WO-2009103735 A1 8/2009
WO WO-2009125987 A2 10/2009
WO WO-2009127922 A2 10/2009
WO WO-2009134053 A2 11/2009
WO WO-2009134076 A2 11/2009
WO WO-2009141159 A1 11/2009
WO WO-2009142421 A2 11/2009
WO WO-2009151295 A2 12/2009
WO WO-2010008203 A2 1/2010
WO WO-2010008244 A2 1/2010
WO WO-2011025167 A2 3/2011
WO WO-2011025267 A2 3/2011
WO WO-2011025269 A2 3/2011
WO WO-2011025270 A2 3/2011
WO WO-2011025271 A2 3/2011
WO 2011110841 9/2011
WO 2011/154331 A1 12/2011
WO 2012/101235 A1 8/2012
WO WO-2012061719 A3 8/2012
WO WO-2012108631 A2 8/2012
WO WO-2012119997 A1 9/2012
WO WO-2012138013 A1 10/2012
WO WO-2012140415 A1 10/2012
WO WO-2012156058 A1 11/2012
WO WO-2012156059 A1 11/2012
WO WO-2012158610 A1 11/2012
WO 2013003887 A1 1/2013
WO WO-2013135853 A1 9/2013
WO WO-2014109308 A1 7/2014
WO WO-2015089419 A2 6/2015
WO 2015/134787 A2 9/2015
WO WO-2016025747 A1 2/2016
WO WO-2016164762 A1 10/2016
WO WO-2016195153 A1 12/2016
WO 2017/184768 A2 10/2017
WO WO-2017176040 A1 10/2017
WO 2017/210666 A1 12/2017
WO WO-2018112555 A1 6/2018
WO WO-2018190355 A1 10/2018
WO 2019/027767 A1 2/2019
WO WO-2019088662 A1 5/2019
WO WO-2019/126627 A1 6/2019
WO WO-2019/152957 A1 8/2019
WO WO-2019199133 A1 10/2019
WO WO-2019220088 A1 11/2019
WO WO-2020017808 A1 1/2020
WO WO-2020/051507 A1 3/2020
WO WO-2020080875 A1 4/2020
WO WO-2020106916 A1 5/2020
WO 2020243647 A1 12/2020
WO WO-2020247382 A1 12/2020
WO WO-2021007382 A1 1/2021
WO WO-2021076977 A1 4/2021
WO WO-2021091188 A1 5/2021
WO WO-2021125797 A1 6/2021
WO WO-2021194253 A1 9/2021
WO WO-2021255262 A1 12/2021
WO WO-2022091971 A1 5/2022
WO WO-2022120194 A1 6/2022
WO WO-2022129097 A2 6/2022
WO WO-2022139687 A1 6/2022
WO 2022192591 A1 9/2022
WO WO-2022216977 A1 10/2022
WO WO-2022245307 A1 11/2022
WO WO-2022266119 A1 12/2022
WO WO-2023023055 A1 2/2023
WO WO-2023107574 A2 6/2023
WO WO-2023193244 A1 10/2023
WO WO-2023239921 A1 12/2023
WO WO-2023239922 A1 12/2023
WO 2024036356 A1 2/2024

OTHER PUBLICATIONS

Convertine et al. “Development of a novel endosomolytic diblock copolymer for siRNA delivery.” Journal of controlled release : official journal of the Controlled Release Society vol. 133,3 (2009): 221-9. DOI:10.1016/j.jconrel.2008.10.004.

Convertine et al. “pH-responsive polymeric micelle carriers for siRNA drugs.” Biomacromolecules vol. 11,11 (2010): 2904-11. doi:10.1021/bm100652w.

Counsell, John R et al. “Lentiviral vectors can be used for full-length dystrophin gene therapy.” Scientific reports vol. 7,1 79. Mar. 6, 2017, doi:10.1038/s41598-017-00152-5.

Dahlman JE, Kauffman KJ, Xing Y, Shaw TE, Mir FF, Dlott CC, Langer R, Anderson DG, Wang ET. Barcoded nanoparticles for high throughput in vivo discovery of targeted therapeutics. Proc Natl Acad Sci U S A. Feb. 21, 2017;114(8):2060-2065. doi: 10.1073/pnas.1620874114. Epub Feb. 6, 2017. PMID: 28167778; PMCID: PMC5338412.

Grimme et al. “Polycation Architecture Affects Complexation and Delivery of Short Antisense Oligonucleotides: Micelleplexes Outperform Polyplexes.” Biomacromolecules 2022, 23, 8, 3257-3271, doi:10.1021/acs.biomac.2c00338.

Haridharan et al. “Exploration of Novel Pyrene Labeled Amphiphilic Block Copolymers: Synthesis Via ATRP, Characterization and Properties.” Journal of Macromolecular Science, Part A, vol. 47, No. 9, Jul. 2010, pp. 918-926, doi:10.1080/10601325.2010.501681.

Kanth et al. “Recent advances in development of poly (dimethylaminoethyl methacrylate) antimicrobial polymers, European Polymer Journal.” vol. 163, 2022, doi:10.1016/j.eurpolymj.2021.110930.

Lauber et al. “pH- and Thermoresponsive Self-Assembly of Cationic Triblock Copolymers with Controlled Dynamics.” Macromolecules 2017, 50, 1, 416-423. doi:10.1021/acs.macromol.6b02201.

Lucas, Christopher R et al. “DNA Origami Nanostructures Elicit Dose-Dependent Immunogenicity and Are Nontoxic up to High Doses In Vivo.” Small (Weinheim an der Bergstrasse, Germany) vol. 18,26 (2022): e2108063. doi:10.1002/smll.202108063.

(56) References Cited

OTHER PUBLICATIONS

Manganiello et al. "Diblock copolymers with tunable pH transitions for gene delivery." Biomaterials vol. 33,7 (2012): 2301-9. doi:10.1016/j.biomaterials.2011.11.019.
Muehlebach et al. "Synthesis of Well-Defined Macromonomers and Comb Copolymers from Polymers Made by Atom Transfer Radical Polymerization." J Polym Sci Part A: Polym Chem. vol. 41,21 (2003): 3425-3439, doi:10.1002/pola.10940.
Okondo et al., DPP8/9 inhibition induces pro-caspase-1-dependent monocyte and mae:rophage pyroptosis, Nature Chemical Biology, vol. 13, No. 1, pp. 46-53, Jan. 2017.
Okondo et al., Inhibition of Dpp8/9 Activates the Nlrp1 b Inflammasome, Cell Chemical Biology, vol. 25, pp. 262-267, Mar. 15, 2018.
PCT Search Report and Written Opinion for PCT/US2023/024960, mailed Aug. 31, 2023.
PCT Search Report and Written Opinion for PCT/US2023/024961, mailed Oct. 6, 2023, 14 pages.
Pegg et al. "Solubilisation of oils in aqueous solutions of a random cationic copolymer." Journal of colloid and interface science vol. 502 (2017): 210-218. doi:10.1016/j.jcis.2017.04.093.
Ponnuswamy, Oligolysine coating, Nature Comm. p. 1 May (Year: 2017).
Samanta, Anirban, and Igor L Medintz. "Nanoparticles and DNA—a powerful and growing functional combination in bionanotechnology." Nanoscale vol. 8,17 (2016): 9037-95. doi:10.1039/c5nr08465b.
Shimatani et al. Chapter 22 Targeted Base Editing with CRISPR-Deaminase in Tomato. pp. 297-307 in Qi, Y. [eds] Plant Genome Editing with CRISPR Systems. Methods in Molecular Biology, vol. 1917. Humana Press, New York, NY. (Year: 2019).
Sprouse et al. "Tuning Cationic Block Copolymer Micelle Size by pH and Ionic Strength." Biomacromolecules 2016, 17, 9, 2849-2859. DOI:10.1021/acs.biomac.6b00654.
Tapio et al. "The potential of DNA origami to build multifunctional materials." Multifunctional Materials, vol. 3, No. 3, DOI: 10.1088/2399-7532/ab80d5.
The Protein Man, "High Efficiency & Stability Protein Crosslinking with EDC & NHS." The Protein Man's Blog—A Discussion of Protein Research, G-Biosciences, Sep. 26, 2017. Available online at (https://info.gbiosciences.com/blog/2-step-protein-coupling-edc-nhs).
The Protein Man, "Modifying Oligonucleotide 5'-Phosphates By EDC for Improved Coupling." The Protein Man's Blog—A Discussion of Protein Research, G-Biosciences, Aug. 29, 2017. Available online at (https://info.gbiosciences.com/blog/modifying-oligonucleotide-5-phosphates-by-edc-for-improved-coupling).
Zhang, Huan et al. "DNA nanostructures coordinate gene silencing in mature plants." Proceedings of the National Academy of Sciences of the United States of America vol. 116,15 (2019): 7543-7548. doi:10.1073/pnas.1818290116.
U.S. Appl. No. 17/715,784, Allowed.
International Search Report and Written Opinion for PCT/US2023/024960, dated Aug. 31, 2023.
Yamada, Yoji, Nucleic Acid Drugs-Current Status, Issues and Expectations, Cancers, 2021, 13(19), 5002, 1-19. (Year: 2021).
Conesa, Ana et al., "A survey of best practices for RNA-seq data analysis." Genome Biology, Jan. 26, 2016, vol. 17, No. 13; doi:10.1186/s13059-016-0881-8.
PCT Written Opinion for PCT/US22/23902, mailed Sep. 9, 2022.
Cristillo, DNA with Talabostat, Biochem. Biophy. Res. Com. pp. 22-26 (Year: 2008).
GenBank ON170268, Ralsonia phage Y0160_4, 2022, 1-9. Obtained online at: https// www.genome.jpdbget-binwww_bgetgenbank-phgON170268 on Nov. 11, 2024. (Year: 2022).
Geneimprint; *Homo sapiens* KCNK9; 2007, 1-20. Obtained online at: tpswww.geneimprint.comsitegenesHomo_sapiens_KCNK9on Nov. 11, 2024. (Year: 2007).
Walter et al., Characterization of a Bean (*Phaseolus vulgaris* L.) Malic-Enzyme Gene, European Journal of Biochemistry, 1994, 999-1009. (Year: 1994).
Institute Pasture, Allele Information, Leptospira locus/sequence definitions—LIC_RS02325: 95, 2017, 1-2. Obtained online at: https:/ /www.psbigsdb.pasteur.frcgibinbigsdbbigsdb.pldb=pubmlst_leptospira_seqdef&page=alleleInfo&locus=LIC_RS02325&allele_id=95 on Nov. 11, 2024. (Year: 2017).
European Search Report for EP Application No. 21901543.5 dated Nov. 27, 2024, 17 pages.
International Search Report and Written Opinion issued in App. No. PCT/US2024/049026, dated Jan. 2, 2025, 13 pages.
International Search Report and Written Opinion issued in App. No. PCT/US2024/048964 mailed Jan. 7, 2025, 13 pages.
Dalal et al., "Polymer design via SHAP and Bayesian machine learning optimizes pDNA and CRISPR ribonucleoprotein delivery," Chem. Sci., 2024, 15, pp. 7219-7228.
International Search Report and Written Opinion for PCT/US2024/049148, mailed Jan. 28, 2025.
Williams et al., "Glycosylated Reversible Addition-Fragmentation Chain Transfer Polymers with Varying Polyethylene Glycol Linkers Produce Different Short Interfering RNA Uptake, Gene Silencing, and Toxicity Profiles", Biomacromolecules, vol. 18, No. 12, Dec. 11, 2017 (Dec. 11, 2017), pp. 4099-4112, XP055881054, ISSN: 1525-7797, DOI: 10.1021/acs.biomac.7b01168.
Wu Yaoying et al., "Glucose-Containing Diblock Polycations Exhibit Molecular Weight, Charge, and Cell-Type Dependence for pDNA Delivery", Biomacromolecules, vol. 15, No. 5, May 12, 2014 (May 12, 2014), pp. 1716-1726, XP093238175, ISSN: 1525-7797, DOI: 10.1021/bm5001229.
Ahmed et al., "The effect of polymer architecture, composition, and molecular weight on the properties of glycopolymer-based non-viral gene delivery systems", Biomaterials, Elsevier, Amsterdam, NL, vol. 32, No. 22, Mar. 30, 2011 (Mar. 30, 2011), pp. 5279-5290, XP028214661, ISSN: 0142-9612, DOI: 10.1016/J.Biomaterials.2011.03.082.
Alidedeoglu et al., "Bioconjugation of D-glucuronic acid sodium salt to well-defined primary amine-containing homopolymers and block copolymers", Journal of Polymer Science Part A: Polymer Chemistry, vol. 48, No. 14, Jun. 14, 2010 (Jun. 14, 2010), pp. 3052-3061, XP055185110, ISSN: 0887-624x, DOI: 10.1002/pola.24083.
Baines (Macromolecules 1996, 29, 8151-8159) (Year: 1996).
Chattarjee (Polymer 46 (2005) 10699-10708) (Year: 2005).
Craigie et al., HIV DNA Integration, Cold Spring Harbor Perspectives in Medicine, 2012, 2, 1-18. (Year: 2012).
Extended European search report for EP application No. 21901543.5, dated Sep. 4, 2025.
Extended European Search Report for patent application No. 22785473.4, dated Jul. 14, 2025.
Freije et al., Detect and Destroy: CRISPR-Based Technologies for the Response Against Viruses, Cell Host & Microbe, 2021, 29, 689-703. (Year: 2021).
Hindmarsh et al., Retroviral DNA Integration, Microbiology and Molecular Biology Reviews, 1999, 63(4), 836-843. (Year: 1999).
International Search Report and Written Opinion for PCT/US2025/031711, mailed Aug. 26, 2025.
International Search Report and Written Opinion issued for PCT/US2024/059000, mailed Apr. 16, 2025.
Ishihara et al., "Water-Soluble and Cytocompatible Phospholipid Polymers for Molecular Complexation to Enhance Biomolecule Transportation to Cells In Vitro," Polymers, 2020, 12:1762) (Year: 2020) DOI: 10.3390/polym12081762.
Lackington et al. In vitro efficacy of a gene-activated nerve guidance conduit incorporating non-viral PEI-pDNA nanoparticles carrying genes encoding for NGF, GDNF and c-Jun (Acta Bio, 2018, 75:115-128) (Year: 2018).
Markou et al., "miRNA-21 as a novel therapeutic target in lung cancer", Lung Cancer: Targets and Therapy, vol. 7, Jan. 1, 2016 (2-16-01-01), pp. 19-27, XP093298330, ISSN: 1179-2728, DOI: 10.2147/LCTT.S60341.
Muppalla (Wiley Periodicals, Inc., 2012, 1637-1650) (Year: 2012).
Oral (Polymers, 2021, 13, 3675, pp. 1-19) (Year: 2021).

(56) References Cited

OTHER PUBLICATIONS

PCT Search Report for PCT/US2021/061846, mailed Mar. 30, 2022.
Piotrowski-Daspit et al., "Polymeric vehicles for nucleic acid delivery", Advanced Drug Delivery Reviews, Elsevier, Amsterdam, NL, vol. 156, Jan. 1, 2020 (Jan. 1, 2020), pp. 119-132, XP086393830, ISSN: 0169-409X, DOI: 10.1016/J.ADDR.2020.06.014.
Sadeghiyeh et al., "MicroRNA-145 replacement effect on growth and migration inhibition in lung cancer cell line", Biomedicine & Pharmacotherapy, vol. 111, Mar. 1, 2019 (Mar. 1, 2019), pp. 460-467, XP085604347, ISSN: 0753-3322, DOI: 10.1016/J.BIOPHA.2018.12.094.
Tramontano et al., Ribonuclease H, An Unexploited Target for Antiviral Intervention Against HIV and Hepatitis B Virus, Antiviral Research, 2019, 171, 104613, 1-21. (Year: 2019).
Z110-Kick, ssDNA as Scaffolds, acs.nanolett, nano lett, p. 4672 (Year: 2025).
Miteva, M. et al. Tuning PEGylation of mixed micelles to overcome intracellular and systemic siRNA delivery barriers. Biomaterials, 38, (2015), pp. 97-107.
Nelson, C. E. et al. Balancing Cationic and Hydrophobic Content of PEGylated siRNA Polyplexes Enhances Endosome Escape, Stability, Blood Circulation Time, and Bioactivity in Vivo. ACS Nano 2013, 7, 10, pp. 8870-8880.
Sugiyama et al. Thermosensitive Copolymers of N-(2-Hydroxypropyl)methacrylamide. and Alkyl Methacrylates (Chem Letters, 1997, 26(3):219-220) (Year: 1997).
Venkataraman, S. et al. The role of PEG architecture and molecular weight in the gene transfection performance of PEGylated poly(dimethylaminoethyl methacrylate) based cationic polymers. Biomaterials, 32 , (2011), pp. 2369-2378.
Werfel, T. A. et al. Combinatorial optimization of PEG architecture and hydrophobic content improves ternary siRNA polyplex stability, pharmacokinetics, and potency in vivo. Journal of Controlled Release, vol. 255, Jun. 10, 2017, pp. 12-26.
International Search Report and Written Opinion for PCT/US2025/040595, mailed Aug. 4, 2025.
Benoit et al., "Controlling Mesenchymal Stem Cell Gene Expression Using Polymer-Mediated Delivery of siRNA", Biomacromolecules, vol. 13, No. 11, (Oct. 11, 2012), pp. 3841-3849, DOI: 10.1021/bm301294n.

* cited by examiner

The DBTL cycle for non-viral gene delivery development based on three pillars: automated synthesis, high throughput testing, and machine learning design.

RAPID DESIGN, BUILD, TEST, AND LEARN TECHNOLOGIES FOR IDENTIFYING AND USING NON-VIRAL CARRIERS

CROSS-REFERENCE TO RELATED APPLICATIONS

This application is a continuation of U.S. patent application Ser. No. 17/715,784, filed Apr. 7, 2022, which claims priority under 35 U.S.C. § 119(e) to U.S. Provisional Application Ser. No. 63/172,069 filed on Apr. 7, 2021, the entire disclosure of each of which is incorporated herein by reference.

SEQUENCE LISTING

The present application is being filed along with a Sequence Listing in XML format. The Sequence Listing is provided as a file entitled 920006-394895_SL.xml, created Sep. 28, 2023, and is 1,304,483 bytes in size. The information in the electronic format of the sequence listing is incorporated herein by reference in its entirety.

FIELD OF THE DISCLOSURE

The disclosure relates to barcoded polymer nanoparticles for in vivo screening and for in vivo therapeutic delivery, and methods therefor. More particularly, the invention relates to polymer nanoparticles, such as reversible addition-fragmentation chain transfer (RAFT) polymer compositions, associated with polynucleotide barcodes, for therapeutic delivery, and for high throughput in vivo screening of drug delivery nanoparticles.

BACKGROUND

Genetic medicines (including gene therapy, gene silencing, splicing regulators, and nuclease based gene editors) are poised to produce revolutionary treatments, including vaccines, infectious disease treatments, antimicrobial treatments, antiviral treatments, and most notably, genetic disease treatments. However, the in vivo delivery of these genetic medicine payloads to the specific tissues and cells that need to be treated, while avoiding tissues and cells that can reduce the efficacy or safety of the genetic medicine, poses a significant challenge. Additional challenges include the ability to deliver large genetic payloads or multiple payloads. Adeno-associated viruses (AAVs) are the most widely used tool for genetic medicine delivery, but AAVs are not able to deliver large genetic payloads or multiple payloads (such as the clustered regularly interspaced short palindromic repeats (CRISPR)/Cas9 system), and they sometimes trigger unwanted immune responses, including the generation of anti-AAV antibodies, a cell mediated response. Some of the immune responses caused by AAV in patients are potentially fatal immune responses.

Therapeutics based on the CRISPR/Cas9 system have an exceptional potential to treat a number of genetic diseases due to the capability of this system for precise and programmable gene editing. Gene editing and repair using the CRISPR/Cas9 system has two main mechanisms, including non-homologous end joining (NHEJ) which repairs the site of cut by inducing random indel mutation, and homology-directed repair (HDR), which repairs the cut site based on a pre-existing template. Because a pre-designed template can be used for HDR-directed repair, therapies based on this mechanism can be tailored to cure a large number of different genetic diseases. However, the main challenge is that HDR repair requires the delivery of CRISPR/Cas9, small guide RNA (sgRNA) and a donor DNA strand at the same time to a particular location. This requirement becomes particularly limiting for in vivo applications because ensuring co-delivery of multiple large molecules to the same targeted location is currently not feasible. For example, the Cas9 enzyme sequence and guide RNA complex is too large to fit into AAVs.

Thus, there is a need for effective non-viral delivery systems, including gene delivery systems. The current state-of-the-art non-viral gene delivery systems, such as liposomes, have many drawbacks such as poor biocompatibility and the inability to easily engineer or functionalize them. Additional concerns are that such non-viral gene delivery systems are easily degraded by various enzymes as they pass through intracellular or intercellular compartments, and these systems have not been able to package multiple large payloads.

The inventors have designed barcoded polymer nanoparticle (e.g., a polymer derived from a controlled living/radical polymerization such as a RAFT polymer) delivery compositions. These compositions have the advantage of being biocompatible, non-toxic, and can be programmed in many ways. For example, the barcoded polymer nanoparticle delivery compositions can be programmed to have functional groups that enable them to evade early degradation, that enable them to evade immune responses, and that enable intracellular imaging and controlled delivery of therapeutic genes and other therapeutic molecules. Thus, these non-viral delivery compositions can enhance the stability, safety, and/or efficacy of genetic medicine payloads and other payloads by providing immune evasion, tissue-directed intracellular delivery, and the ability to deliver large genetic payloads or multiple payloads.

The present disclosure combines these non-viral delivery compositions with rapid design, build, test, and learn (DBTL) technologies that will vastly accelerate gene delivery and address the disadvantages that exist in limited gene delivery vehicles. In addition to hastening editing therapies of today to transition through clinicals, it is anticipated that these technologies will enable the general delivery of larger more molecularly diverse genetic payloads, and other payloads, which will in turn, continue to improve treatments for genetic diseases and other diseases.

SUMMARY

In some aspects, the disclosure provides for a composition comprising a non-viral delivery vehicle comprising one or more nanoparticle forming polymers, and a nucleic acid construct.

In some aspects, the disclosure provides for a method of in vivo screening for a desired polymer nanoparticle for use as a delivery vehicle, the method comprising (a) preparing a library comprising two or more types of polymer nanoparticles, wherein each polymer nanoparticle is associated with a nucleic acid construct comprising a different polynucleotide barcode, (b) administering the library to an animal, (c) removing cells or tissues from the animal, (d) isolating the nucleic acid constructs from the cells or the tissues of the animal, (e) detecting the nucleic acid constructs in the cells or the tissues of the animal, and (f) identifying the desired polymer nanoparticle for use as a delivery vehicle.

In some aspects, the disclosure provides for a method of treating a patient with a disease, the method comprising administering to the patient the polymer nanoparticle identified in the in vivo screening methods described herein, wherein the polymer nanoparticle further comprises a drug payload, such as a polynucleotide or a protein payload or a small molecule therapeutic payload, and treating the disease in the patient.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the "EXAMPLES" are applicable to any of the following embodiments of the invention described in the numbered clauses below.

1. A composition comprising:
a. a non-viral delivery vehicle comprising one or more nanoparticle forming polymers, and
b. a nucleic acid construct.
2. The composition of clause 1, wherein the non-viral delivery vehicle comprises a polymer nanoparticle.
3. The composition of clause 1 or 2, wherein the nucleic acid construct is associated with the non-viral delivery vehicle via an electrostatic interaction.
4. The composition of any one of clauses 1 to 3, wherein the nucleic acid construct is associated with the non-viral delivery vehicle by an electrostatic interaction of a positively charged polymer segment of the one or more nanoparticle forming polymers and a negatively charged polynucleotide segment of the nucleic acid construct.
5. The composition of any one of clauses 1 to 3, wherein the nucleic acid construct is associated with the non-viral delivery vehicle by a high affinity, non-covalent bond interaction between a biotin molecule on the 5' and/or the 3' end of the nucleic acid construct and a molecule that binds to biotin on the one or more nanoparticle forming polymers.
6. The composition of any one of clauses 1 to 3, wherein the nucleic acid construct is associated with the non-viral delivery vehicle by a covalent bond between a carboxy terminated polymer segment and the nucleic acid construct, wherein the nucleic acid construct comprises a primary amine on the 5' and/or the 3' end.
7. The composition of any one of the preceding clauses, wherein the nucleic acid construct comprises:
a. two primer binding segments; and
b. one or more unique polynucleotide barcodes between the two primer binding segments.
8. The composition of clause 7, wherein the primer binding segments range in length from about 15 base pairs to about 30 base pairs.
9. The composition of clause 7 or 8, wherein the primer binding segments are a universal primer binding set.
10. The composition of any one of clauses 7 to 9, wherein the one or more polynucleotide barcodes comprise unique sequences of 6-20 nucleotides in length.
11. The composition of clause 10, wherein the polynucleotide barcodes further comprise a hamming distance of at least 2-6 bases between any two unique polynucleotide barcode sequences.
12. The composition of any one of the preceding clauses, wherein the nucleic acid construct further comprises from about 6 to about 12 random bases at the 3' end of the polynucleotide barcode.
13. The composition of clause 12, wherein the about 6 to about 12 random bases at the 3' end of the polynucleotide barcode are for bioinformatic removal of PCR duplicates.
14. The composition of any one of the preceding clauses, wherein the nucleic acid construct ranges in length from about 42 nucleotides to about 210 nucleotides.
15. The composition of any one of the preceding clauses, wherein the one or more nanoparticle forming polymers comprise monomer units compatible with a controlled living/radical polymerization.
16. The composition of any one of the preceding clauses, wherein the one or more nanoparticle forming polymers are prepared by reversible-deactivation radical polymerization, atom transfer radical polymerization (ATRP), reversible addition fragmentation chain transfer polymerization (RAFT), iodine-transfer polymerization (ITP), selenium-centered radical-mediated polymerization, telluride-mediated polymerization (TERP), stibine-mediated polymerization, or ring-opening polymerization.
17. The composition of any one of the preceding clauses, wherein the one or more nanoparticle forming polymers are prepared from monomers containing a vinyl group.
18. The composition of any one of the preceding clauses, wherein the one or more nanoparticle forming polymers are prepared using a chain transfer agent such as those used in reversible addition-fragmentation chain transfer (RAFT).
19. The composition of any one of the preceding clauses, wherein the one or more nanoparticle forming polymers are RAFT block copolymers comprising
a. a first terminus comprising a first capping unit derived from a first chain transfer agent in a RAFT copolymerization process;
b. a first block prepared from one or more monomer units covalently attached to the first reactive functional unit, and having a molecular weight ($M_n$) in the range of about 1 kDa to about 500 kDa and a degree of polymerization in the range of about 10 to about 2500;
c. optionally a second block prepared from one or more monomer units covalently attached to the first block, and having a molecular weight ($M_n$) in the range of about 1 kDa to about 500 kDa and a degree of polymerization in the range of about 20 to about 2000; and
d. a second terminus comprising a second capping unit derived from a first or a second chain transfer agent.
20. The composition of clause 19, wherein the non-viral delivery vehicle has one or more of an overall molecular weight ($M_n$) in the range of about 25 kDa to about 60 kDa, an overall degree of polymerization in the range of about 700 to about 900, a target size in the range of about of about 10 to about 60 nm, and a maximum corona-to-core ratio (CCR) of about 1.5 to about 3.5.
21. The composition of clause 19 or 20, wherein the first block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.
22. The composition of clause 19 or 20, wherein the first block is prepared from one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl) methacrylate, or methyl methacrylate.
23. The composition of any one of clauses 19 to 22, wherein the second block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

24. The composition of any one of clauses 19 to 23, wherein the second block is a random copolymer prepared from two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

25. The composition of any one of clauses 19 to 23, wherein the second block is a random copolymer prepared from three different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

26. The composition of any one of clauses 19 to 25, wherein the second block is a random copolymer prepared from 2-dimethylaminoethyl acrylate, butyl methacrylate, and propyl acrylic acid; or 2-dimethylaminoethyl acrylate and butyl methacrylate; or 2-dimethylaminoethyl acrylate, butyl methacrylate, and ethyl acrylic acid.

27. The composition of any one of clauses 19 to 26, wherein each chain transfer agent is independently selected from the group consisting of bis(carboxymethyl)trithiocarbonate, bis(2-amino-2-oxoethyl) trithiocarbonate, bis[4-(2-hydroxyethoxycarbonyl)benzyl] trithiocarbonate, 4-cyano-4-(ethylsulfanylthiocarbonyl) sulfanylvpentanoic acid, 4-cyano-4-((phenylcarbonothioyl)thio)pentanoic acid, and 4-cyano-4-[(dodecylsulfanylthiocarbonyl)sulfanyl] pentanoic acid.

28. The composition of any one of clauses 19 to 27, wherein the first capping unit is of the formula

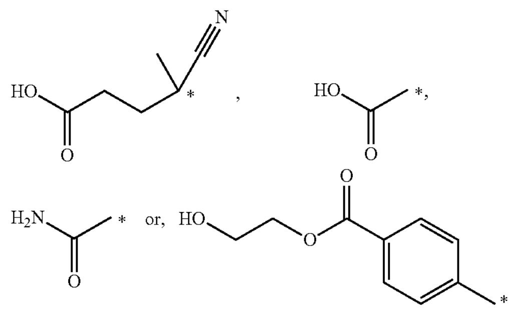

wherein * represents a point of covalent attachment to the first block.

29. The composition of any one of clauses 19 to 28, wherein the second capping unit is of the formula

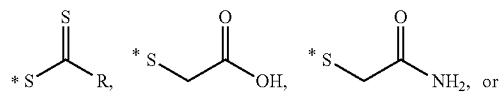

-continued

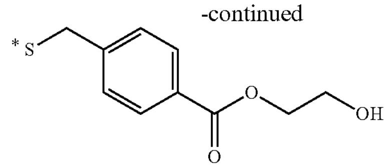

wherein * represents a point of covalent attachment to the second block, and R is —$SC_2$—$C_{12}$ alkyl or $C_6H_5$, 30. A method of in vivo screening for a desired polymer nanoparticle for use as a delivery vehicle, the method comprising (a) preparing a library comprising two or more types of polymer nanoparticles, wherein each polymer nanoparticle is associated with a nucleic acid construct comprising a different polynucleotide barcode, (b) administering the library to an animal, (c) removing cells or tissues from the animal, (d) isolating the nucleic acid constructs from the cells or the tissues of the animal, (e) detecting the nucleic acid constructs in the cells or the tissues of the animal, and (f) identifying the desired polymer nanoparticle for use as a delivery vehicle.

31. The method of clause 30 wherein the polymer nanoparticle associated with the nucleic acid construct is according to any one of clauses 1 to 29.

32. The method of clause 30 or 31 wherein the nucleic acid construct is detected by a method selected from the group consisting of the polymerase chain reaction (PCR), isothermal amplification, sequencing, or a combination thereof, to obtain nucleotide sequence data.

33. The method of any one of clauses 30 to 32, wherein the polymer nanoparticle is loaded with a payload.

34. The method of clause 33, wherein the payload is a luminescent molecule.

35. The method of clause 34, wherein the luminescence is used to track the biodistribution or cell uptake via imaging.

36. The method of any one of clauses 30 to 35, wherein the administration to the animal is via an intramuscular, an intravenous, an intraperitoneal, an oral, or a pulmonary route.

37. The method of any one of clauses 30 to 36, wherein the nucleic acid construct is isolated from the cells and the tissues by mixing with a first organic compound and incubating the organic phase with an aqueous phase of the cell or tissue sample, separating the organic phase from the aqueous phase, mixing the organic phase with a second organic compound, incubating the mixture, precipitating the nucleic acid construct from the mixture, removing the organic phase by evaporation, and resuspending the nucleic acid construct in an aqueous composition.

38. The method of clause 37, wherein the organic phase comprises phenol chloroform.

39. The method of clause 37, wherein the nucleic acid construct is separated from cationic material in the cells or tissues by titrating the aqueous composition of the nucleic acid construct to a pH of greater than 7.4.

40. The method of clause 30, wherein the nucleic acid construct is separated from material in the cells or tissues by binding the nucleic acid construct with a molecule with a binding affinity to the nucleic acid construct greater than the binding affinity to the cell or tissue material.

41. The method of clause 30, wherein the nucleic acid construct is separated from material in the cells or tissues via size exclusion chromatography.
42. The method of clause 30, wherein the nucleic acid construct is separated from material in the cells or tissues via dialysis or diafiltration.
43. The method of clause 30, wherein the nucleic acid construct is separated from material in the cells or tissues via filtration.
44. The method of clause 30, wherein the nucleic acid construct is separated from material in the cells or tissues by digesting proteins using an enzyme.
45. The method of clause 44 wherein the enzyme is Proteinase K.
46. The method of clause 30, wherein the nucleic acid constructs associated with the polymer nanoparticles are detected by first diluting the isolated nucleic acid constructs by a factor of at least 1000 times, and then amplifying the nucleic acid constructs by PCR using primers.
47. The method of clause 46, wherein the primers from the PCR step are enzymatically digested prior to detection of amplicons.
48. The method of clause 32, wherein the nucleotide sequence data is converted to fast Q files; and the fast Q files are mapped to known polynucleotide barcodes and the polynucleotide barcodes are enumerated.
49. A method of treating a patient with a disease, the method comprising administering to the patient the polymer nanoparticle identified in the in vivo screening method of any one of clauses 30 to 48, wherein the polymer nanoparticle further comprises a payload, and treating the disease in the patient.

BRIEF DESCRIPTION OF THE DRAWINGS

FIGS. 5(*a*)-5(*c*) are a schematic drawing of nucleic acid construct labeling reaction methods using electrostatic loading reaction (FIG. 5(*a*)), avidin-streptavidin conjugation (FIG. 5(*b*)), and direct amidification (FIG. 5(*c*)).

In FIG. 11(*a*), the area under the curve denoted by the bar in the graph accounts for 84.17% of the cells.

DETAILED DESCRIPTION OF ILLUSTRATIVE EMBODIMENTS

Figure 1:
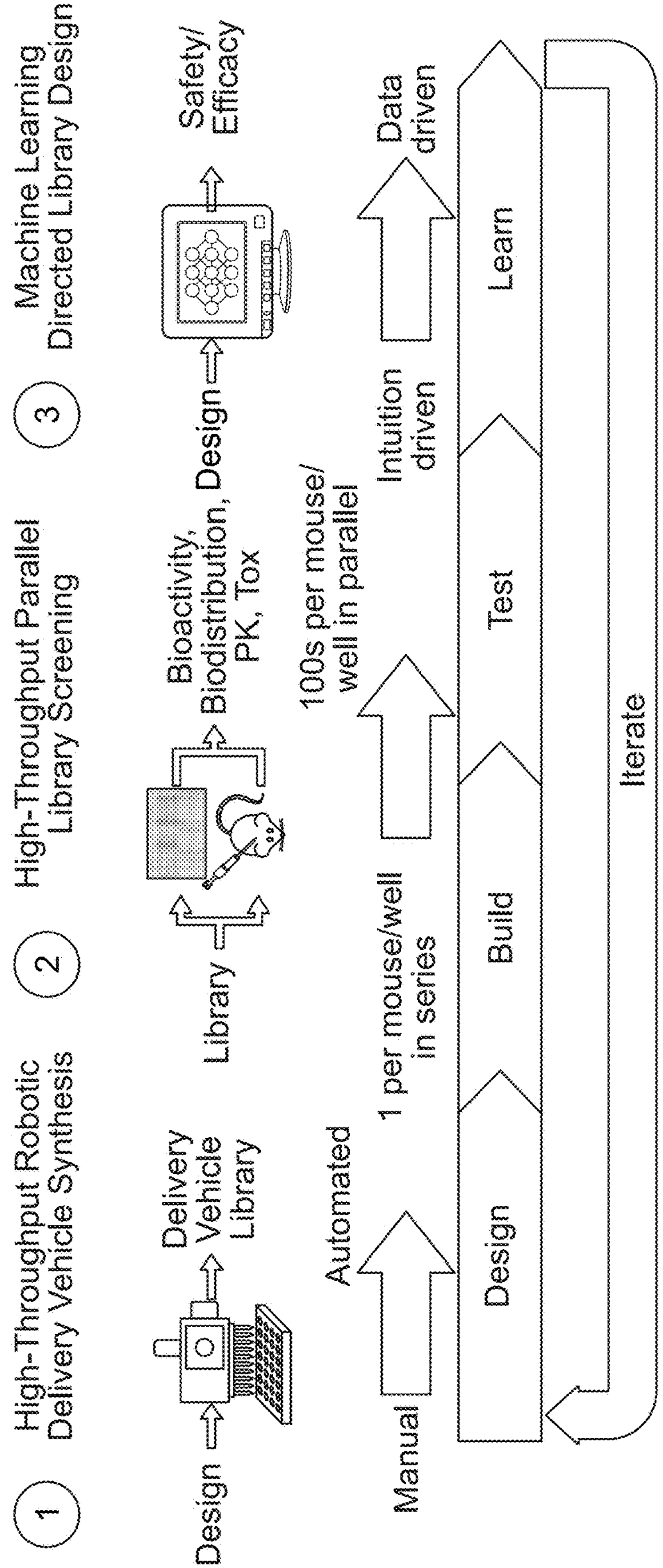
FIG. 1 is a schematic diagram showing a simplified flow diagram illustrating a DBTL cycle for non-viral gene delivery development based on automated synthesis, high throughput testing, and machine learning design.

The invention relates to barcoded polymer nanoparticles for in vivo screening and for in vivo therapeutic delivery, and methods therefor. More particularly, the invention relates to polymer nanoparticles, such as a controlled living/radical polymerization products, such as reversible addition-fragmentation chain transfer (RAFT) polymer compositions, associated with polynucleotide barcodes, for therapeutic delivery, and for high throughput in vivo screening of drug delivery nanoparticles. In one embodiment, the payload can be a nucleic acid of 3 kB or more, or any other suitable payload, such as another polynucleotide or a protein or a small molecule therapeutic or a luminescent molecule.

The invention relates to the use of barcoded polymer nanoparticle compositions (e.g., a polymer nanoparticle derived from a controlled living/radical polymerization process, such as RAFT copolymers) as a platform with a high degree of tunability in structure and function, opportunities to protect payloads from adverse reactions or degradation by the immune system, and passive cell targeting via surface charge, or particle size. These delivery systems also lend themselves to computer-aided design, and they have suitable pathways to robust, commercial scale manufacturing processes with higher yields and fewer purification steps than viral delivery composition manufacturing processes.

In one embodiment a composition comprising a polymer nanoparticle (e.g., a polymer nanoparticle derived from a controlled living/radical polymerization process, such as RAFT polymer) associated with a nucleic acid construct is provided. In another embodiment, a method of in vivo screening to identity a desired polymer nanoparticle (e.g., a polymer nanoparticle derived from a controlled living/radical polymerization process, such as RAFT polymer) associated with a nucleic acid construct for use as a delivery vehicle is provided. In another embodiment, a method of treating a patient with a disease is provided comprising administering to the patient the polymer nanoparticle identified in the screening method.

In one embodiment, the method of in vivo screening for a desired polymer nanoparticle for use as a delivery vehicle comprises, (a) preparing a library comprising two or more types of polymer nanoparticles, wherein each polymer nanoparticle is associated with a nucleic acid construct comprising a different polynucleotide barcode, (b) administering the library to an animal, (c) removing cells or tissues from the animal, (d) isolating the nucleic acid constructs from the cells or tissues of the animal, (e) detecting the nucleic acid constructs in the cells or tissue of the animal, and (f) identifying the desired polymer nanoparticle for use as a delivery vehicle. In various embodiments, the nucleic acid construct can be detected by, for example, the polymerase chain reaction (PCR), isothermal amplification, or sequencing the nucleic acids in the cells or tissues of the animal.

In another embodiment, a method of treating a patient with a disease is provided, comprising administering to the patient the polymer nanoparticle identified in the in vivo screening method, wherein the polymer nanoparticle further comprises a drug payload, such as a polynucleotide or a protein payload, or a small molecule therapeutic or luminescent molecule payload, and treating the disease in the patient.

In various embodiments, any suitable route for administration of the library of polymer nanoparticles associated with nucleic acid constructs for the method of in vivo screening for the polymer nanoparticle associated with a nucleic acid construct, or for the method of treatment can be used including parenteral administration. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. In one embodiment, means for parenteral administration include needle (including microneedle) injectors, needle-free injectors and infusion techniques. In other embodiments, oral or pulmonary routes of administration can be used.

In one aspect, libraries of barcoded polymer nanoparticles can be pooled and concentrated before administration to the animal of the nucleic acid constructs associated with the polymer nanoparticles. Methods for library preparation and for sequencing are described in Green and Sambrook, "Molecular Cloning: A Laboratory Manual", 4th Edition, Cold Spring Harbor Laboratory Press, (2012), incorporated herein by reference.

In various embodiments, cell or tissue samples may be analyzed for the presence of the polymer nanoparticle associated with the nucleic acid constructs described herein. The samples can be any tissue, cell, or fluid sample from an animal, for example, selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, or any tissue or cell sample from an animal Exemplary tissue or cell samples include brain tissue or cells, muscle tissue or cells, skin tissue or cells, heart tissue or cells, kidney tissue or cells, stomach tissue or cells, liver tissue or cells, urinary tract tissue or cells, gastrointestinal tract tissue or cells, head or neck tissue or cells, lung tissue or cells, reproductive tract tissue or cells, pancreatic tissue or cells, or any other tissue or cell type from an animal.

In one illustrative aspect for removing cells or tissues from the animal and isolating the nucleic acid constructs from the cells or tissues of the animal, the nucleic acid constructs are removed from cells or tissues of the animal. In various embodiments, nucleic acid constructs (e.g., DNA or RNA) obtained from the tissues or cells of the animal can be removed by rupturing the cells and isolating the nucleic acid constructs from the lysate. Techniques for rupturing cells and for isolation of nucleic acids are well-known in the art, and removal techniques include homogenization, such as by using a bead-beating technique. In other embodiments, the nucleic acid constructs may be isolated by rupturing cells using a detergent or a solvent, such as phenol-chloroform. In another aspect, the nucleic acid constructs may be separated from the lysate by physical methods including, but not limited to, centrifugation, dialysis, diafiltration, filtration, size exclusion, pressure techniques, digestion of proteins with Proteinase K, or by using a substance with an affinity for nucleic acids such as, for example, beads that bind nucleic acids.

In one illustrative embodiment, the nucleic acid constructs are removed from cells or tissues by treating with a mixture of an organic phase (e.g., phenol chloroform) and an aqueous phase (e.g., water). The organic phase (e.g., phenol chloroform) is isolated and the nucleic acid construct can be precipitated by raising the pH, for example, to pH 7.4. The organic phase (e.g., phenol chloroform) can be evaporated and the nucleic acid constructs can be suspended in water and diluted to appropriate concentrations for PCR and/or sequencing. In one embodiment, the isolated nucleic acid constructs are suspended in either water or a buffer after sufficient washing.

In other embodiments, commercial kits are available for isolation of the nucleic acid constructs, such as Qiagen™, Nuclisensm™, Wizard™ (Promega), QiaAmp 96 DNA Extraction Kit™ and a Qiacube HT™ instrument, and Promegam™. Methods for preparing nucleic acids for PCR and/or sequencing are also described in Green and Sambrook, "Molecular Cloning: A Laboratory Manual", 4th Edition, Cold Spring Harbor Laboratory Press, (2012), incorporated herein by reference.

The polynucleotide barcodes can be detected by using, for example, the polymerase chain reaction (PCR), isothermic amplification, sequencing, and/or imaging. The polymerase chain reaction (PCR) has been developed to analyze nucleic acids in a laboratory. PCR evolved over the last decade into a new generation of devices and methods known as Next Generation Sequencing (NGS). NGS provides faster detection and amplification of nucleic acids at a cheaper price. The NGS devices and methods allow for rapid sequencing as the nucleic acids are amplified in massively parallel, high-throughput platforms.

In one illustrative aspect, the nucleic acid constructs can be sequenced, to detect the polynucleotide barcodes using any suitable sequencing method including Next Generation Sequencing (e.g., using Illumina, ThermoFisher, or PacBio or Oxford Nanopore Technologies sequencing platforms), sequencing by synthesis, pyrosequencing, nanopore sequencing, or modifications or combinations thereof can be used. In one embodiment, the sequencing can be amplicon sequencing. In another embodiment, the sequencing can be whole genome sequencing. In another embodiment, the sequencing can be exome/targeted hybridization sequencing. Methods for sequencing nucleic acids are also well-known in the art and are described in Sambrook et al., "Molecular Cloning: A Laboratory Manual", Cold Spring Harbor Laboratory Press, incorporated herein by reference.

In one aspect, the nucleic acid construct can comprise a polynucleotide barcode and the barcode comprises a unique sequence not present in any known genome for identification of the polynucleotide barcode. In another embodiment, a set of different nucleic acid constructs with different polynucleotide barcodes (e.g., 88 or 96 different polynucleotide barcodes) can be used to allow for multiplexing of samples on one sequencing run.

In various embodiments, the polynucleotide barcodes can be from about 5 to about 35 base pairs in length, about 5 to about 34 base pairs in length, about 5 to about 33 base pairs in length, about 5 to about 32 base pairs in length, about 5 to about 31 base pairs in length, about 5 to about 30 base pairs in length, about 5 to about 29 base pairs in length, about 5 to about 28 base pairs in length, about 5 to about 27 base pairs in length, about 5 to about 26 base pairs in length, about 5 to about 25 base pairs in length, about 5 to about 24 base pairs in length, about 5 to about 23 base pairs in length, about 5 to about 22 base pairs in length, about 5 to about 21 base pairs in length, about 5 to about 20 base pairs in length, about 5 to about 19 base pairs in length, about 5 to about 18 base pairs in length, about 5 to about 17 base pairs in length, about 5 to about 16 base pairs in length, about 5 to about 15 base pairs in length, about 5 to 14 base pairs in length, about 5 to 13 base pairs in length, about 5 to 12 base pairs in length, about 5 to 11 base pairs in length, about 5 to 10 base pairs in length, about 5 to 9 base pairs in length, about 5 to 8 base pairs in length, about 6 to 10 base pairs in length, about 7 to 10 base pairs in length, about 8 to 10 base pairs in length, or about 6 to about 20 base pairs in length.

Various embodiments of polynucleotide barcodes are shown below in Table 1 (labeled "Polynucleotide Barcodes"). These polynucleotide barcodes can be used in the nucleic acid constructs alone or in combinations of, for example, two or more polynucleotide barcodes, three or more polynucleotide barcodes, four or more polynucleotide barcodes, etc. In the embodiment where more than one polynucleotide barcode is used, the hamming distance between the polynucleotide barcodes can be about 2 to about 6 nucleotides, or any suitable number of nucleotides can form a hamming distance, or no nucleotides are present between the polynucleotide barcodes.

TABLE 1

| Polynucleotide Barcodes | SEQ ID NO: |
|---|---|
| GCTACATAAT | 1 |
| ATGTTACACA | 2 |
| TGGGGCCCAA | 3 |
| TAGTTTATCC | 4 |
| ACCCCGTCTT | 5 |
| CCGGCCATCA | 6 |
| GAGCTTGCTC | 7 |
| ACGTTCTATA | 8 |
| TACAGCAAAA | 9 |
| GTTAGGTGGT | 10 |
| GGAGACCGAC | 11 |
| TGGCCCCTTG | 12 |
| TGGCCGTAAG | 13 |
| CGTTCGTCAA | 14 |
| CGGACGTGGA | 15 |
| AGAGGGGGCA | 16 |
| GTTCAGGTCG | 17 |
| CTCGCAAGAG | 18 |
| GCAACGACTT | 19 |
| GCCATCCATC | 20 |
| TTCCGAGCAG | 21 |
| CTTCTGGACA | 22 |
| AACATTAGAC | 23 |
| AAGCAATAGT | 24 |
| AGGGTAAGAC | 25 |
| CGTTGTCTTG | 26 |
| TTTCCCCGCC | 27 |
| CGAATGGATC | 28 |
| CATCACTTGC | 29 |
| CTCTCGCACT | 30 |
| GTTCACGTGC | 31 |
| AATAAGCCTG | 32 |
| GTTAACAATT | 33 |
| ATTCAGATCC | 34 |
| CCTGCTGATT | 35 |
| CTTGGTCATA | 36 |
| TCTTCCTGTT | 37 |
| ACTGCCATGG | 38 |
| CATGTATAGT | 39 |

TABLE 1-continued

| Polynucleotide Barcodes | SEQ ID NO: |
|---|---|
| GGTAGCGGCA | 40 |
| TCACTCTAAC | 41 |
| AAGGTGCACC | 42 |
| AATGCTCGTT | 43 |
| TGTCTAGAAA | 44 |
| CTGCCTGCCT | 45 |
| ACTATAAAAG | 46 |
| TAGTATCGAG | 47 |
| ATCGCAGTCC | 48 |
| TCATCAGAAC | 49 |
| TCCTAGACGC | 50 |
| GCCGGGCGGG | 51 |
| GCCCAGAAGA | 52 |
| CTTAGAGCTG | 53 |
| GTCTGCGCTT | 54 |
| CGCCGTCCTT | 55 |
| TTTATCTGCT | 56 |
| TGCTTCGGAG | 57 |
| GGGGAGAATG | 58 |
| GTGGTAAGTG | 59 |
| GAAATTAGTA | 60 |
| GCTATCCTAA | 61 |
| ATCTGTACGA | 62 |
| AGTTCGGGGC | 63 |
| CGAGTCTGTC | 64 |
| ATCCTACGCA | 65 |
| ATGGTGGATA | 66 |
| CCTCTAACTA | 67 |
| ATAGCTGCAC | 68 |
| GACAGAATTT | 69 |
| CAATTGGCAT | 70 |
| TCTAGTAGAC | 71 |
| TTATTCATGG | 72 |
| TTGGCAACCG | 73 |
| CATAATACAT | 74 |
| ACAGACTCAC | 75 |
| GCGATGCTGC | 76 |
| CATCTTTGCC | 77 |

TABLE 1-continued

| Polynucleotide Barcodes | SEQ ID NO: |
|---|---|
| GTGACTCCAG | 78 |
| GGACGAGTCT | 79 |
| TAGTGGCGTG | 80 |
| AACGCAGCTT | 81 |
| AGAACAGGTG | 82 |
| AGGCTATGTT | 83 |
| CCTGGATCTT | 84 |
| CTAGCCGGCC | 85 |
| ACCAGTTATC | 86 |
| ACGTTATAGC | 87 |
| TCGAGTTTGA | 88 |
| TGAAGCGAGC | 89 |
| GACTGGCGAA | 90 |
| GATGGACCTA | 91 |
| GTCCACAACG | 92 |
| CCTCCCCAGA | 93 |
| TTATGACGCC | 94 |
| CTTGATCCGT | 95 |
| AATGCGCAAT | 96 |
| GTACCCCTCA | 97 |
| CGACAGCTCG | 98 |
| TGACCTGGCT | 99 |
| TTCATAGCCC | 100 |
| CCCAAGAGAA | 101 |
| AAACGAAGTA | 102 |
| GACGTTTACA | 103 |
| GATCGATTTG | 104 |
| CACTGTCACC | 105 |
| TGTGAGAGTT | 106 |
| GACGTAACCT | 107 |
| CAGACTCTGC | 108 |
| TATGCCAATA | 109 |
| ACAGGTGATG | 110 |
| GTCATCGCGT | 111 |
| TCTTATAAAC | 112 |
| GTGTAGACTG | 113 |
| AAACAACCGG | 114 |
| ATCCTGTACC | 115 |
| TTATAAGAAT | 116 |

TABLE 1-continued

| Polynucleotide Barcodes | SEQ ID NO: |
|---|---|
| ATAAGTAGGC | 117 |
| TCTCGTAAGG | 118 |
| GATCCGCCGC | 119 |
| TGTCAGGTTT | 120 |
| TCCGAAGCCC | 121 |
| TCCATGTCCA | 122 |
| GTGATGGTAC | 123 |
| CTCCACATAC | 124 |
| TTCGGATGAG | 125 |
| ACGACATCGC | 126 |
| GAGATGCACA | 127 |
| TTTGTATGGC | 128 |
| CTTTTCTAGA | 129 |
| AGTCTAATCA | 130 |
| GACTTAGCCA | 131 |
| TATCACAGTA | 132 |
| AAGCTCGAGT | 133 |
| TGTTACGACA | 134 |
| AAGGATAGTC | 135 |
| GCACTTAGCC | 136 |
| GAGGGATCCG | 137 |
| ATTCTAGAAG | 138 |
| GATAACTGAT | 139 |
| ATCTGACTGT | 140 |
| CAAAGCGAAC | 141 |
| GAAATTGCGA | 142 |
| GGGTCCAGTC | 143 |
| ATCAGGTAGC | 144 |
| GAAAGGTCCT | 145 |
| GGCTACCACA | 146 |
| TTATTGCTGA | 147 |
| CGCCGCGTTT | 148 |
| TTTTCAAAAG | 149 |
| CTGGGCTAAA | 150 |
| CCCGATGAGA | 151 |
| TGGGAAATAT | 152 |
| GTACGAGCGG | 153 |
| GCGTGCAGCT | 154 |

TABLE 1-continued

| Polynucleotide Barcodes | SEQ ID NO: |
|---|---|
| AGTCTGCGGA | 155 |
| TAACTATTTA | 156 |
| GAGTTGCCGG | 157 |
| CAGCCCGGCG | 158 |
| TCACCTACAT | 159 |
| AGTGGCTAAC | 160 |
| AGAATGTGAG | 161 |
| TAGTTTCGCA | 162 |
| CTTCATTTCT | 163 |
| GCCATGATAT | 164 |
| ACGGCAAATC | 165 |
| ATCGATAGTA | 166 |
| CCTAAAGGCA | 167 |
| TACGAGCGGT | 168 |
| TTTGTCGTCG | 169 |
| TACAAGCTTG | 170 |
| GACCAACACG | 171 |
| GAACGACGAA | 172 |
| TCGGAACGCA | 173 |
| ATCCGGTGGT | 174 |
| TAAAACGTAG | 175 |
| TATGTGAGCC | 176 |
| GAGGCATCGA | 177 |
| GAATGGGTGG | 178 |
| AACGACACAA | 179 |
| GTACGATGCA | 180 |
| AGAAGGCGCC | 181 |
| CCGCAATGGA | 182 |
| TACGGATTTT | 183 |
| GTCGTTAGCT | 184 |
| GGACTAGGGC | 185 |
| ATTGGTATTC | 186 |
| ATCCCAGAGA | 187 |
| GTCCCAGCTC | 188 |
| CACGAGGAAT | 189 |
| TACAATTGCA | 190 |
| ATTCCTGAAT | 191 |
| TAGCGAGGCG | 192 |
| CTGGATGGGC | 193 |

TABLE 1-continued

| Polynucleotide Barcodes | SEQ ID NO: |
|---|---|
| GCGACGGCCA | 194 |
| ACCTGCACAA | 195 |
| CATGACAGAC | 196 |
| TTACCAACGT | 197 |
| CAGGTGTGTG | 198 |
| CGAGGGACGG | 199 |
| CGTCTCGGTA | 200 |
| TAAGCTATCT | 201 |
| TACTCCCCTA | 202 |
| TTATATTCAT | 203 |
| AGCGATCTGC | 204 |
| TCTTCTGATC | 205 |
| ATAGTTCCCA | 206 |
| TTTACGGGTG | 207 |
| GTGTCCCCTG | 208 |
| GCGGGGGTCG | 209 |
| CATTGATCTA | 210 |
| AGGGACGGTG | 211 |
| CAGTTACTTT | 212 |
| CCATACTTCC | 213 |
| ATCAGAATTA | 214 |
| AAACTAGGCA | 215 |
| AATGTCGTTG | 216 |
| CACATGGGTC | 217 |
| GGTCGCTGGT | 218 |
| ACTGTATTAC | 219 |
| CCGAGACGCG | 220 |
| ACTCCAACCC | 221 |
| ATATTACAAG | 222 |
| CCATGGATAG | 223 |
| CCGTCTCAAT | 224 |
| GATCGTCGGG | 225 |
| TCTTGTTTTG | 226 |
| AATATTGCTC | 227 |
| AACGTCGTCT | 228 |
| AATATTTTTG | 229 |
| CGTAACGTGC | 230 |
| GCGTGGTTAT | 231 |

TABLE 1-continued

| Polynucleotide Barcodes | SEQ ID NO: |
|---|---|
| CAAAACATTA | 232 |
| CGTATCCTGA | 233 |
| TCGCTTACAA | 234 |
| TCCATTGTGT | 235 |
| GCCCCCATTC | 236 |
| TGACGTCTAT | 237 |
| TGGGCCGAGG | 238 |
| AAGTGTCAAG | 239 |
| GACAGTAGAG | 240 |
| CGCAGCCATC | 241 |
| GAGGCAGAAC | 242 |
| GTTGAAATTG | 243 |
| ATCTGATAAA | 244 |
| AGCTGTCTCT | 245 |
| TTTTAGGTTA | 246 |
| TATCTGTCCG | 247 |
| AAAACATATG | 248 |
| GTAAAGAAGA | 249 |
| TCGACGTGCA | 250 |
| TAGATCTTAA | 251 |
| CACTGGTCAC | 252 |
| ATTCTGATGT | 253 |
| ATGGCCCTGA | 254 |
| GGTGATGAGA | 255 |
| CACCGTGGGG | 256 |
| GCTTGCTCGG | 257 |
| CCAGTTGAAC | 258 |
| CGTCTGTACC | 259 |
| CCAACGCGGC | 260 |
| ACGTGATCGA | 261 |
| CCATCGAATC | 262 |
| CGGTGTCTGC | 263 |
| AAACCACCTC | 264 |
| TCAATGTTCC | 265 |
| TTCGACATGT | 266 |
| AGGCACGATA | 267 |
| CACGAGATCA | 268 |
| CATGCTGGGG | 269 |
| TACCATGGTT | 270 |

TABLE 1-continued

| Polynucleotide Barcodes | SEQ ID NO: |
|---|---|
| TTGCCCATAT | 271 |
| TGCACATTCG | 272 |
| GTTATGTTGG | 273 |
| TGAGTTATGA | 274 |
| GATGGCCCCC | 275 |
| GATGGGTTAC | 276 |
| AGCTACGTTG | 277 |
| ACCCCATGCA | 278 |
| TACTACCGTT | 279 |
| TCGCTTCTAC | 280 |
| CTGGCAGTGC | 281 |
| TCTATATATA | 282 |
| GGATTAGTTC | 283 |
| GTGTTACGCT | 284 |
| TCGACTCCGT | 285 |
| GGTAGCAGGC | 286 |
| TATTGGATTC | 287 |
| GTTCGATCGA | 288 |
| ATATTAATAT | 289 |
| AGAACGATTG | 290 |
| GTAAAGTGTA | 291 |
| CCCATGTGCC | 292 |
| GTGGCCTCGC | 293 |
| GACACTAGGA | 294 |
| ATATTCTGAC | 295 |
| TAAGTAGACG | 296 |
| TAACGGTCTA | 297 |
| TAGTTTCATT | 298 |
| TTGGATCCGA | 299 |
| CGTGACAACC | 300 |
| CGCGCTCAGA | 301 |
| CGTTCTTAAT | 302 |
| ACAAGAGTTT | 303 |
| AGGGTTATAG | 304 |
| ACCACGACTC | 305 |
| GTACTCGGGG | 306 |
| ACAAATATCT | 307 |
| GATCGGGGTG | 308 |

TABLE 1-continued

| Polynucleotide Barcodes | SEQ ID NO: |
|---|---|
| ATGTAACTCC | 309 |
| ATGAAGAAGC | 310 |
| ATGTATTGTC | 311 |
| TGCATTGGAA | 312 |
| GCGGACGATC | 313 |
| CCGTACTTGA | 314 |
| TTTGCCCCCG | 315 |
| ACCTCACGCG | 316 |
| ATTAAGGGGC | 317 |
| CGTGGACATG | 318 |
| TTAGCCCTTC | 319 |
| CGAGAGTTTG | 320 |
| TGCATCCTCT | 321 |
| TGCGATTCCG | 322 |
| TTATTACGTT | 323 |
| TGATGTGGTT | 324 |
| GGGCGTCAAT | 325 |
| CCCTTGAAAT | 326 |
| TCTTTGGGGC | 327 |
| ACCGGCAGGC | 328 |
| GCTAAAATCT | 329 |
| GCCGTTGACG | 330 |
| GGAGTTGTTG | 331 |
| TACTTGAGAA | 332 |
| CGGGTGCGCT | 333 |
| AAAAGCGTCT | 334 |
| GTAAAGATAG | 335 |
| GCCTGGTCAG | 336 |
| GGCAAAAAGG | 337 |
| ACCCTTCTCT | 338 |
| TCACATAGTG | 339 |
| TCGTCTGTGC | 340 |
| TGCTCGGATC | 341 |
| AGCAGTCCCG | 342 |
| TTTGGGCTGT | 343 |
| CTCACGATCT | 344 |
| TGGCGCATAC | 345 |
| GCAATTGAAA | 346 |
| TCGGGAGACG | 347 |

TABLE 1-continued

| Polynucleotide Barcodes | SEQ ID NO: |
|---|---|
| CCCGGCGAAA | 348 |
| TGATGCGGAA | 349 |
| AACTGAGGCG | 350 |
| CATATTATTT | 351 |
| AAAAGTCATT | 352 |
| AAGCGGTGAG | 353 |
| AAGGTAATCA | 354 |
| CTGACACTTA | 355 |
| CTGTTTTCTA | 356 |
| CACATGGCAG | 357 |
| TTCAATCCGG | 358 |
| TGTCCGGCAT | 359 |
| TGGTACCGTG | 360 |
| AAGAGATATT | 361 |
| GATGTACTAC | 362 |
| GAAATGGAAT | 363 |
| TTAAAATACT | 364 |
| TGACCGGAAC | 365 |
| GTCGCCGCAA | 366 |
| TAGGATACCG | 367 |
| AGTCCAATTG | 368 |
| GGGGGCTATA | 369 |
| ACCTTCAGTT | 370 |
| ATGGCAAGTA | 371 |
| AGAATGTTTT | 372 |
| AGTTCGTTTG | 373 |
| CACTACTGAC | 374 |
| GATCAAGAGC | 375 |
| ATTTATCGAG | 376 |
| CCTTTTTCCA | 377 |
| GCACAGAGGT | 378 |
| TGATCTGAAT | 379 |
| GTTGGAGGGA | 380 |
| TTTTGAAGGT | 381 |
| TAAGTCCTAA | 382 |
| GGTGTTAGGG | 383 |
| TGTATGCACC | 384 |
| CCGTGCCATT | 385 |

TABLE 1-continued

| Polynucleotide Barcodes | SEQ ID NO: |
|---|---|
| GAAATCACCC | 386 |
| TTTGCACGTG | 387 |
| CGTCTGTTTT | 388 |
| CTACACCACA | 389 |
| TGCTACAGGG | 390 |
| GGGAATATAT | 391 |
| TCATGTATTT | 392 |
| TCTCCGTTTA | 393 |
| TACCTCTCGC | 394 |
| GCTTCAACCG | 395 |
| ATGAAGCTAC | 396 |
| CGGTACAACT | 397 |
| GTGTGGTCGT | 398 |
| GGGGTCATGT | 399 |
| AGGCAGCCCA | 400 |
| CAAGCACGAT | 401 |
| TCAAATGGAT | 402 |
| GGACTGAATA | 403 |
| CCGTAGACGT | 404 |
| CGGCGTACCG | 405 |
| GGCGGCGCCC | 406 |
| AGACTTGATC | 407 |
| ACCTTGCACA | 408 |
| TAAGGTGAGT | 409 |
| TTGTTGTTTC | 410 |
| GAGGGAATAC | 411 |
| CTCGTACGCG | 412 |
| CCGCGGTTTA | 413 |
| TTAAAGTTAA | 414 |
| GCATATGGGT | 415 |
| AGTCTGAGCC | 416 |
| TGTCGGTTCG | 417 |
| GGTCTCAACC | 418 |
| GTAACGGCAT | 419 |
| ACACTGAGAA | 420 |
| CCCAACGTCG | 421 |
| AAGAAACTGC | 422 |
| ACCAGCCCAC | 423 |
| TGTAGTTACT | 424 |

TABLE 1-continued

| Polynucleotide Barcodes | SEQ ID NO: |
|---|---|
| GGCTAGAGGC | 425 |
| GTTCGGCAGA | 426 |
| CCAAAATAGA | 427 |
| CCCATATAAC | 428 |
| GTCACTACCG | 429 |
| GTAGTGTGGC | 430 |
| CAATCTCATA | 431 |
| CCATGTTATA | 432 |
| TAAGCAGTGG | 433 |
| TCGGCGGCTA | 434 |
| TATTAAATGC | 435 |
| GTCGCCATTA | 436 |
| GGCGTCGTTC | 437 |
| CTAGTAGATA | 438 |
| TCGTCAGTAT | 439 |
| GGGGTATCGG | 440 |
| TGCTCTGCCA | 441 |
| TGCCGTAACT | 442 |
| CGGTACAGGC | 443 |
| TCCTAATTTG | 444 |
| TCTTTCTGGA | 445 |
| CCGCGACTTG | 446 |
| ACCTATAGCG | 447 |
| GCCGGCACCT | 448 |
| TTTGATAGGC | 449 |
| ACTGTGAGCT | 450 |
| TTATCGTTCA | 451 |
| ACTAGTGGCC | 452 |
| CCTCCGTGGT | 453 |
| TTAGGGTATG | 454 |
| GAATCAGGCG | 455 |
| GGCTGACCAA | 456 |
| TGCCAGACCG | 457 |
| TCCCTACGCG | 458 |
| TCCGCTGGAG | 459 |
| GGATCAAAAC | 460 |
| TTCACCTCAC | 461 |
| GACACACGGC | 462 |

TABLE 1-continued

| Polynucleotide Barcodes | SEQ ID NO: |
|---|---|
| TGGGCGATTA | 463 |
| TAAGATCTTC | 464 |
| CTCCGACTAC | 465 |
| GGGCCATCAT | 466 |
| TCAGGCCAGA | 467 |
| CTTGTGGGGC | 468 |
| AGATAGTCTG | 469 |
| GCGTCAAAGT | 470 |
| ACGAAAATTT | 471 |
| GAGTCTGGTG | 472 |
| ATCGAGCGAC | 473 |
| GGTCCTCAGA | 474 |
| TGATTTTGTC | 475 |
| GCATTTCTCA | 476 |
| GCATGCCAGT | 477 |
| ATTAGACGAC | 478 |
| AAAGCCCATA | 479 |
| CACTACATTC | 480 |
| CACGGTTTCT | 481 |
| CCCACCAGTG | 482 |
| CTCACTTGTC | 483 |
| GATAGACTCT | 484 |
| ATTTCCATTT | 485 |
| ATATGTGGCC | 486 |
| CGGGACGAAC | 487 |
| AGAACCGTGA | 488 |
| TAGTGTACTG | 489 |
| AACTAATCGA | 490 |
| CGAAGTGACG | 491 |
| CGGAGCCTCG | 492 |
| ATCACACGAG | 493 |
| CGACGAGTTC | 494 |
| GCTTCCCGTG | 495 |
| GATTCATACC | 496 |
| GAGAGAAGCG | 497 |
| GAAGTGGCCT | 498 |
| GGACGACGCC | 499 |
| TAGGGTCTCA | 500 |
| AACTACAGGT | 501 |

TABLE 1-continued

| Polynucleotide Barcodes | SEQ ID NO: |
|---|---|
| GTGGCCTGTG | 502 |
| CTTTACCAGC | 503 |
| CGCGTTACTG | 504 |
| TTGCTCCCGT | 505 |
| CATCAAACAA | 506 |
| GCTTTATGAT | 507 |
| CTGCATACTG | 508 |
| GGTGGCTCAG | 509 |
| GGACGATCAA | 510 |
| CCGACTGGTG | 511 |
| GGAACAACCG | 512 |
| GAACGAGACC | 513 |
| CACCAAGAAA | 514 |
| ATGCATTACC | 515 |
| GTATCATGCC | 516 |
| AGTAGATGTT | 517 |
| CTCTAGATGT | 518 |
| GCTACTTGTG | 519 |
| TATGAAACGT | 520 |
| CCTCGTTGAT | 521 |
| CTAGAGCCAT | 522 |
| TAGAGTTATA | 523 |
| AACGAGAGGC | 524 |
| GGTCTACCGT | 525 |
| GCCCCCTCAC | 526 |
| CATAGGAATT | 527 |
| TCCGGCTCGT | 528 |
| TGAGAGTCGG | 529 |
| CGTAGAAATA | 530 |
| CTTTACATGA | 531 |
| GAGCGCCGTC | 532 |
| GGCTCTCGGC | 533 |
| AGAGCTTGTT | 534 |
| AATCAGCCAC | 535 |
| AGAAGAGCCA | 536 |
| TCGTATGAGT | 537 |
| TTCTTCCTCG | 538 |
| ACACAAAAGC | 539 |

TABLE 1-continued

| Polynucleotide Barcodes | SEQ ID NO: |
|---|---|
| CGCGGGACCC | 540 |
| GTCGCGACAC | 541 |
| CCGGAGGAAA | 542 |
| CGGCGTATGA | 543 |
| TAGGCATTCT | 544 |
| AAAGGAGGGA | 545 |
| ACCTTTACGG | 546 |
| CTACCGTTAA | 547 |
| GAGCTTCGCC | 548 |
| GCCATAGAAG | 549 |
| TTTAGCGTAT | 550 |
| GCAAACAGAT | 551 |
| TAGGTCATGG | 552 |
| CTCTAACAGA | 553 |
| GGCTCATGAA | 554 |
| CAATGTCTCA | 555 |
| TGATCGTATT | 556 |
| GCGCTTTTCA | 557 |
| AAGATTATAT | 558 |
| ACTAGCTGAC | 559 |
| GGTGAGCTCA | 560 |
| CGCTTTCGCT | 561 |
| TGATTCAAAA | 562 |
| ACTGAACAGG | 563 |
| ATTCGAGCTA | 564 |
| TGTAGGCTAA | 565 |
| ACAAAGCTTT | 566 |
| GCCCGAGGGA | 567 |
| GCCCGCTGGG | 568 |
| ACCCCGCTGA | 569 |
| CTTATGCCCT | 570 |
| CCGCCATAGC | 571 |
| CTTAATGATT | 572 |
| CAGTCCACAA | 573 |
| ATGGACGGAC | 574 |
| CGGCCTCTCG | 575 |
| TAGTCGCCAT | 576 |
| GTTGATCTTC | 577 |
| ACTTGCCAAG | 578 |

TABLE 1-continued

| Polynucleotide Barcodes | SEQ ID NO: |
|---|---|
| ATGACTGGTT | 579 |
| TGTCGTAGGA | 580 |
| AGCAAACACG | 581 |
| TACTGATGAA | 582 |
| GTATCCCATA | 583 |
| TAGCCAGGTT | 584 |
| CGTGTGGCGA | 585 |
| ATCGAATTGC | 586 |
| CCCCAATATT | 587 |
| CCCGTTTCTC | 588 |
| TCCGCATCTA | 589 |
| CAAGCCTCAT | 590 |
| TTTCAATCCC | 591 |
| CCTTCCCATC | 592 |
| AGGTACAAGA | 593 |
| GTGTAATGGA | 594 |
| AAACTGAGCT | 595 |
| ATCTCTGCCC | 596 |
| CGACATTTGC | 597 |
| TGTGAACCCG | 598 |
| TGACACCCCA | 599 |
| TAGGCCAAAG | 600 |
| GAAATTGTAG | 601 |
| GCGTCTGATT | 602 |
| TCTCATTGTT | 603 |
| CTGACATCTC | 604 |
| GTATCCAGTG | 605 |
| GATGGCCGTT | 606 |
| TCACCCTCTC | 607 |
| GGCACTATTC | 608 |
| AAATAACTGT | 609 |
| CAGCTCCATT | 610 |
| CTCTTGACTC | 611 |
| TTTCCTATAC | 612 |
| CCATACCCGA | 613 |
| TCGCCGAGCG | 614 |
| CGCTGAAGCC | 615 |
| TCTGGCCCCA | 616 |

TABLE 1-continued

| Polynucleotide Barcodes | SEQ ID NO: |
|---|---|
| GCTACATTGA | 617 |
| CGCATCATAA | 618 |
| GCAAAGGGCC | 619 |
| AACGGCGCAG | 620 |
| CGACTGACAT | 621 |
| ATGACAGGGC | 622 |
| CAAGTTCTCC | 623 |
| TCGCCGCTTT | 624 |
| ATGCCGGAAA | 625 |
| GCGGTTACTA | 626 |
| GACATTACAA | 627 |
| CAGAGAGGGC | 628 |
| GCACCGCCTC | 629 |
| CGGTCCGAGC | 630 |
| TGTCCGGTGC | 631 |
| GGTCGGTTGC | 632 |
| GCTCAGCTAA | 633 |
| AGCAGTTCGT | 634 |
| AAATCGATGA | 635 |
| GCTCGGTATG | 636 |
| CCCGCCGCGG | 637 |
| GTGTGATAGG | 638 |
| TTGGACTCCA | 639 |
| TGCTTATCTA | 640 |
| CAAAAGGCGT | 641 |
| TAGGGGGCCT | 642 |
| AAGTATTAAT | 643 |
| GTTTAGCCCG | 644 |
| CGCTAATATG | 645 |
| ACAACACGTT | 646 |
| AGAGATGCTC | 647 |
| TGCCTGATAT | 648 |
| CTTGTAAGTA | 649 |
| CATATTGCCG | 650 |
| CTTAGAAAGT | 651 |
| ATGTTGTATT | 652 |
| CGCATTGAAG | 653 |
| TTATGTTGGT | 654 |
| TCGCCTCAGA | 655 |

TABLE 1-continued

| Polynucleotide Barcodes | SEQ ID NO: |
|---|---|
| TTCGTTGAGG | 656 |
| GGTGCCGGGC | 657 |
| ACCATTGTAA | 658 |
| TTGATTGTCA | 659 |
| CGGCTCACCT | 660 |
| CTATCACATG | 661 |
| GTAGACAGAA | 662 |
| CCTTTACCAA | 663 |
| GCACATCGAC | 664 |
| TCTCACTTTC | 665 |
| TTCGAGTACT | 666 |
| TAGAAGAGCA | 667 |
| AACCCCACCA | 668 |
| CTGTATCAGT | 669 |
| ACATAATGAG | 670 |
| AGCCTTCCGC | 671 |
| CAGTGCTTTT | 672 |
| TAGTCCGTGT | 673 |
| CGGAATCGGT | 674 |
| CTTGCGGAGA | 675 |
| AAAAATTTGG | 676 |
| TGTTTTCCGC | 677 |
| ATGCTAGGCG | 678 |
| GACTAATTTC | 679 |
| CTGTAGTAAC | 680 |
| CGGATGACTT | 681 |
| TCAGAGTGGA | 682 |
| CAAAATAGCG | 683 |
| GAAGAAGAAG | 684 |
| CACCCGCACG | 685 |
| ACGATGCCCG | 686 |
| CCTACTACAC | 687 |
| ATTGAAACAA | 688 |
| GACCGAAGAT | 689 |
| ACGGCCTGAA | 690 |
| AGGGGAGGTC | 691 |
| CAATCAACTT | 692 |
| GGACAACCGA | 693 |

TABLE 1-continued

| Polynucleotide Barcodes | SEQ ID NO: |
|---|---|
| TCCCTAAGGC | 694 |
| GTTCTACACG | 695 |
| ACTAACCAGT | 696 |
| GAAGCTGGAT | 697 |
| GGAACCATGG | 698 |
| CTCTACCTGG | 699 |
| TAATGCCTGC | 700 |
| TAAAGGCAAT | 701 |
| CGCCTGGGAA | 702 |
| TCTTGGGGAA | 703 |
| AGAGAGAGAG | 704 |
| GCGTTGGCGC | 705 |
| TTACGACAGA | 706 |
| GGAACTCTTA | 707 |
| GATTGTGGAG | 708 |
| GGGCACTGAT | 709 |
| AGACGCACCA | 710 |
| CCAATTATAA | 711 |
| TAGAGACGCA | 712 |
| CCTCTTGTCG | 713 |
| GAGGAAGCTC | 714 |
| AGTCCCGAGT | 715 |
| TGCTTGCAGT | 716 |
| CCCACTTCCC | 717 |
| CGTTGCCGCG | 718 |
| CCCCTGGTTC | 719 |
| ACGACCAATA | 720 |
| CTTAGGGTTC | 721 |
| AAACATATCA | 722 |
| GGGTCGTAGA | 723 |
| CTCCGTAGCG | 724 |
| CTGGTCATAA | 725 |
| TTGACAGATC | 726 |
| GAGTAAAGTC | 727 |
| ATATGGGCTT | 728 |
| TACAACTACT | 729 |
| AATTCAGCCG | 730 |
| GATTGTACTA | 731 |
| TCGTAATGCG | 732 |

TABLE 1-continued

| Polynucleotide Barcodes | SEQ ID NO: |
|---|---|
| CGATAACTGC | 733 |
| AACTTGGCGG | 734 |
| CGTGGATGTA | 735 |
| CCTTCCCGAA | 736 |
| CTAAACCCGT | 737 |
| CAACATTCCC | 738 |
| CTTACCCTCT | 739 |
| GGAAAGTTCT | 740 |
| CGGATTGGCT | 741 |
| AATGTAGGGC | 742 |
| AATGAATCGC | 743 |
| ATCATACACC | 744 |
| AGTTGGGCAG | 745 |
| AGAAGAAGGG | 746 |
| GCGTGCGCTA | 747 |
| CCCCGATAAA | 748 |
| TACCAAGTGC | 749 |
| TGTGTTTTCG | 750 |
| CCCAGATGTC | 751 |
| GCGAGCTTCC | 752 |
| GTGTCACGTA | 753 |
| ATAGGCCGAG | 754 |
| GAGCTACCAG | 755 |
| CGCGGCGGAG | 756 |
| TCTTGCACGA | 757 |
| TGCCCTAAAG | 758 |
| TTGCGCTTTG | 759 |
| CATATAAAGG | 760 |
| AATAGCGAAT | 761 |
| TACGCTAAGG | 762 |
| ACTTAGTTCG | 763 |
| CGTGCGGAAC | 764 |
| ACCCGATTCG | 765 |
| TGCAGAGTTT | 766 |
| GAATCATTAG | 767 |
| AGTACACTGG | 768 |
| TTGTGCGGTT | 769 |
| ATGACATGCA | 770 |

TABLE 1-continued

| Polynucleotide Barcodes | SEQ ID NO: |
|---|---|
| TTCTCGGACG | 771 |
| AGATTGAAGA | 772 |
| GGCGGACTGT | 773 |
| TTTATGGTAA | 774 |
| CAGTAGGGTG | 775 |
| GACAGGCAAG | 776 |
| GATGTGTCGT | 777 |
| ACTTGACGGA | 778 |
| AAGTCCGAAA | 779 |
| TGGGTGTAGG | 780 |
| ACTTACCGCG | 781 |
| CTGTGCACCC | 782 |
| ATTGCTCTCT | 783 |
| CAGAAGACAA | 784 |
| TTACGCTATA | 785 |
| ACGTGGAAAT | 786 |
| TGAGGCTGGT | 787 |
| ATTATGAGAT | 788 |
| GACTTGTAGT | 789 |
| TCGCTGAGGA | 790 |
| CCCAACTCTA | 791 |
| GATAGGGAGG | 792 |
| TAGAAATCAG | 793 |
| GTCGCTAGAA | 794 |
| AAAATAGAAA | 795 |
| GCTCCTGGGT | 796 |
| CGCGCTCGCG | 797 |
| GGCAAACGCA | 798 |
| TTTACTACCT | 799 |
| ATCCTAAACT | 800 |
| CTCCGTATGT | 801 |
| TATCGTCCAG | 802 |
| GCCGGCGGTA | 803 |
| TGCTCCATTT | 804 |
| TGGCTGTTGT | 805 |
| TACTGCGCAA | 806 |
| TATACGGCTT | 807 |
| GGTTATTACC | 808 |
| ATCAGGAGGA | 809 |

TABLE 1-continued

| Polynucleotide Barcodes | SEQ ID NO: |
|---|---|
| CTATTGCCAG | 810 |
| ACGTACACAC | 811 |
| CAGCCTAGCT | 812 |
| GAAAAACAAC | 813 |
| CGTTCAGTTA | 814 |
| CAATCAGAAT | 815 |
| GGGCTACTCT | 816 |
| CCCCATTGGG | 817 |
| TAGGGAACGG | 818 |
| CAGCTGATAC | 819 |
| ATTCCTGTGA | 820 |
| TCAGAGCCGT | 821 |
| CATGAAAAGC | 822 |
| TGACCTGTGA | 823 |
| GCATTAGCAG | 824 |
| GACAGAACCA | 825 |
| TCCAGTATAT | 826 |
| TGTTCCGCTA | 827 |
| GATATCCATT | 828 |
| CATATGGACC | 829 |
| GATATAGTAA | 830 |
| CACCTTTTTT | 831 |
| AGCTTGCGGG | 832 |
| CGCACAGGGA | 833 |
| TCTGGGTGCT | 834 |
| TGAGTCGTTT | 835 |
| TTACAATGTG | 836 |
| CTTGCAAACA | 837 |
| TGTCGAGCTG | 838 |
| ACTTTAACCT | 839 |
| ATATAAGTGC | 840 |
| GGAAGGGCGT | 841 |
| TTTGACTTGA | 842 |
| GTATAAACGG | 843 |
| TAACCGGATG | 844 |
| TTCTCATCAG | 845 |
| CTCGGTTACG | 846 |
| ATATGGTTCT | 847 |

TABLE 1-continued

| Polynucleotide Barcodes | SEQ ID NO: |
|---|---|
| CGCCCCCGAA | 848 |
| ACCTCGATCG | 849 |
| CTCGAATAAT | 850 |
| GCCCGAGCTT | 851 |
| AACAGTCAAC | 852 |
| CTGGAACCTC | 853 |
| AATAACGGGG | 854 |
| ACGCCCCACT | 855 |
| GGCAACATGA | 856 |
| GCTATTTCGC | 857 |
| TTCCACTTTA | 858 |
| GCCGATGGAT | 859 |
| AAGTTGGTAA | 860 |
| CACTAGCTAG | 861 |
| ACATGCCCCT | 862 |
| TTCATTACTC | 863 |
| GGTTTAATAT | 864 |
| CCTGCAGTGA | 865 |
| TCTTTAAGTT | 866 |
| TGGCGATCGA | 867 |
| CTTTTTAGCT | 868 |
| CCCAGTCTCT | 869 |
| AAATGTTTCG | 870 |
| ATATAAGACG | 871 |
| TCACTTTACA | 872 |
| CCTGGCGCCC | 873 |
| GGATTACTGG | 874 |
| GAATGATCTT | 875 |
| GCTCGGATCG | 876 |
| CAGCTGCGAG | 877 |
| ACCCTTACTA | 878 |
| AGGTGAAACT | 879 |
| CGAATTTGAT | 880 |
| CGCTGTGCGG | 881 |
| TTACCGCACC | 882 |
| GGAATCTTAA | 883 |
| CTCAACACCC | 884 |
| CGTGCCCTTG | 885 |
| GCAGGCTCGA | 886 |

TABLE 1-continued

| Polynucleotide Barcodes | SEQ ID NO: |
|---|---|
| ACCAACGAAG | 887 |
| CCTGTAATTT | 888 |
| GGGTGGGATG | 889 |
| TTGCTCACCG | 890 |
| TTACGACCAC | 891 |
| TTTTCTAACC | 892 |
| GCTTTAGATA | 893 |
| CACGTATTGG | 894 |
| AAATATCTCC | 895 |
| GCTGGAAAAC | 896 |
| GAGCGCATTA | 897 |
| GTGGAGGGGT | 898 |
| TCCACTGGGA | 899 |
| CAATAGCGGA | 900 |
| CATCTAGTTT | 901 |
| GAAGTTCCGG | 902 |
| AGCGAGATTC | 903 |
| TTAAGGTCGG | 904 |
| AATGGTTAGG | 905 |
| CGTTATTATA | 906 |
| ACGGAAAGGA | 907 |
| CCTTGTCCCG | 908 |
| ATACTTTTTT | 909 |
| CTGGGTCTGG | 910 |
| AACCATTGCG | 911 |
| AGACCGGGCC | 912 |
| TGGGACACAC | 913 |
| TGCGCAGTTG | 914 |
| CGTTCGCCTT | 915 |
| TCTCACTCGT | 916 |
| ACACCGACGT | 917 |
| TTCAGCCCCT | 918 |
| AGGCGACTAA | 919 |
| TGCTATCAAG | 920 |
| GTCCAGTAGC | 921 |
| CGTGTGGGCG | 922 |
| GTGGTTCTCC | 923 |
| GCAGCCGACG | 924 |

TABLE 1-continued

| Polynucleotide Barcodes | SEQ ID NO: |
|---|---|
| GCTGTCCACG | 925 |
| CGACACTCAT | 926 |
| CATGGCACCT | 927 |
| TGTGACGTGT | 928 |
| TTTGGACTAA | 929 |
| TTCATGCCCG | 930 |
| TTGATCGTGG | 931 |
| TAGCATAGGA | 932 |
| GTAGTTGCAA | 933 |
| GGGACAGCTA | 934 |
| AAACCCCCAA | 935 |
| ACTCTCACAA | 936 |
| ATCATTGCCA | 937 |
| CCAGTTTGCG | 938 |
| ACATTAGTCA | 939 |
| CTCCAGGGTA | 940 |
| GAAGGGCCAA | 941 |
| CAGTCTCCCC | 942 |
| GAGACATTCC | 943 |
| AACGGTGTTG | 944 |
| AGCATTATCA | 945 |
| CTATACCGAG | 946 |
| AACTGGATCA | 947 |
| GTCTTGTCGG | 948 |
| GACGAGCCGC | 949 |
| GGAACACTGT | 950 |
| TAAATGCGTT | 951 |
| GCGAACACAG | 952 |
| TTCTCTCAAC | 953 |
| GTCGTACTGA | 954 |
| TGTGGCGTAA | 955 |
| TGAGCGGCGT | 956 |
| CCTCGTGAAC | 957 |
| GAGCAATGAA | 958 |
| CGAGACCTAA | 959 |
| AACTGAGCGC | 960 |
| TAAAGCTCGT | 961 |
| CTCTTTACGT | 962 |
| CCCCGTGGAA | 963 |

TABLE 1-continued

| Polynucleotide Barcodes | SEQ ID NO: |
|---|---|
| TCGGTTCGTC | 964 |
| CTGCTTACAC | 965 |
| ACACCGTAAT | 966 |
| CCTGGTCGGC | 967 |
| GGTTATTTGG | 968 |
| GCAACTGAGT | 969 |
| ATAAGGCCTC | 970 |
| CGTGCGAAGG | 971 |
| GTCACACACT | 972 |
| CATACGGCAA | 973 |
| GAACTGCCCA | 974 |
| AATATGTGAA | 975 |
| CCGATCCTGT | 976 |
| CAAAGAGCCT | 977 |
| TAACTTAGAG | 978 |
| CAGCATGTAG | 979 |
| CCCCATGCAG | 980 |
| TCTGAACCAC | 981 |
| GCGTGCAAAA | 982 |
| GCTAGTACCG | 983 |
| TTTCCCGCGC | 984 |
| CCTTAGTAGG | 985 |
| TTGTGTCTTG | 986 |
| GCAACGAAGC | 987 |
| TGAAACCCTT | 988 |
| TTCTACGATC | 989 |
| ATTAAAGGTG | 990 |
| TATCTAACGG | 991 |
| AGTGCTCCTG | 992 |
| CCGTCCCTCT | 993 |
| CTAACGAGCG | 994 |
| AAGTCCGGCT | 995 |
| GGCGTATAAG | 996 |
| AGATATTAGG | 997 |
| TCCTAACAGC | 998 |
| GAGGATACGC | 999 |
| CGCTCTTTAA | 1000 |
| ACCGGCAGGC | 328 |

TABLE 1-continued

| Polynucleotide Barcodes | SEQ ID NO: |
|---|---|
| GCTAAAATCT | 329 |
| GCCGTTGACG | 330 |
| GGAGTTGTTG | 331 |
| TACTTGAGAA | 332 |
| CGGGTGCGCT | 333 |
| AAAAGCGTCT | 334 |
| GTAAAGATAG | 335 |
| GCCTGGTCAG | 336 |
| GGCAAAAAGG | 337 |
| ACCCTTCTCT | 338 |
| TCACATAGTG | 339 |
| TCGTCTGTGC | 340 |
| TGCTCGGATC | 341 |
| GGCGTATAAG | 996 |
| AGATATTAGG | 997 |
| TCCTAACAGC | 998 |
| GAGGATACGC | 999 |
| CGCTCTTTAA | 1000 |
| GGCGTATAAG | 996 |
| AGATATTAGG | 997 |
| TCCTAACAGC | 998 |
| GAGGATACGC | 999 |

In another embodiment, a random sequence fragment can be linked to the 5' and/or the 3' end of the polynucleotide barcode and the random sequence fragment can, for example, be used for bioinformatic removal of PCR duplicates. The random sequence fragment can also be used to add length to the nucleic acid construct and can serve as a marker for bioinformatic analysis to identify the beginning or the end of the polynucleotide barcode after sequencing. In another embodiment, the nucleic acid construct comprises at least a first and a second random sequence fragment, and the first random sequence fragment can be linked to the 5' end of the polynucleotide barcode and the second random sequence fragment can be linked to the 3' end of the polynucleotide barcode. In another embodiment, one or at least one random sequence fragment is linked to the 5' and/or the 3' end of the polynucleotide barcode. In one aspect, the random sequence fragments can be extended as needed to make the nucleic acid construct longer for different applications such as whole genome sequencing where short inserts may be lost.

In various embodiments, the random sequence fragments can be from about 5 to about 20 base pairs in length, about 5 to about 19 base pairs in length, about 5 to about 18 base pairs in length, about 5 to about 17 base pairs in length, about 5 to about 16 base pairs in length, about 5 to about 15 base pairs in length, about 5 to about 14 base pairs in length, about 5 to about 13 base pairs in length, about 5 to about 12 base pairs in length, about 5 to about 11 base pairs in length, about 5 to about 10 base pairs in length, about 5 to about 9 base pairs in length, about 5 to about 8 base pairs in length, about 6 to about 10 base pairs in length, about 7 to about 10 base pairs in length, or about 8 to about 10 base pairs in length.

In another illustrative aspect, the polynucleotide barcode may be flanked by primer binding segments (i.e., directly or indirectly linked to the polynucleotide barcode) so that the nucleic acid construct comprising the polynucleotide barcode can be amplified during a polymerase chain reaction (PCR) and/or sequencing protocol. In one aspect, the primer binding segments can be useful for binding to one or more universal primers or a universal primer set. In one illustrative embodiment, the universal primers can contain overhang sequences that enable attachment of index adapters for sequencing. In this aspect, the primers can be any primers of interest. In this embodiment, the first primer binding segment can be linked at its 3' end to the 5' end of a first random sequence fragment and the second primer binding segment can be linked at its 5' end to the 3' end of a second random sequence fragment with the polynucleotide barcode between the random sequence fragments. In another embodiment, the first primer binding segment can be linked at its 3' end to the 5' end of the polynucleotide barcode and the second primer binding segment can be linked at its 5' end to the 3' end of a random sequence fragment (see FIG. 1 for an example) linked to the 3' end of the polynucleotide barcode. In another embodiment, the first primer binding segment can be linked at its 3' end to the 5' end of a random sequence fragment and the second primer binding segment can be linked at its 5' end to the 3' end of the polynucleotide barcode where the polynucleotide barcode is linked at its 5' end to the 3' end of the random sequence fragment. In yet another embodiment, the first primer binding segment can be linked at its 3' end to the 5' end of the polynucleotide barcode and the second primer binding segment can be linked at its 5' end to the 3' end of the polynucleotide barcode.

In embodiments where primer binding segments are included in the nucleic acid construct, the primer binding segments can range in length from about 15 base pairs to about 30, from about 15 base pairs to about 29 base pairs, from about 15 base pairs to about 28 base pairs, from about 15 base pairs to about 26 base pairs, from about 15 base pairs to about 24 base pairs, from about 15 base pairs to about 22 base pairs, from about 15 base pairs to about 20 base pairs, 16 base pairs to about 28 base pairs, from about 16 base pairs to about 26 base pairs, from about 16 base pairs to about 24 base pairs, from about 16 base pairs to about 22 base pairs, from about 16 base pairs to about 20 base pairs, 17 base pairs to about 28 base pairs, from about 17 base pairs to about 26 base pairs, from about 17 base pairs to about 24 base pairs, from about 17 base pairs to about 22 base pairs, from about 17 base pairs to about 20 base pairs, 18 base pairs to about 28 base pairs, from about 18 base pairs to about 26 base pairs, from about 18 base pairs to about 24 base pairs, from about 18 base pairs to about 22 base pairs, or from about 18 base pairs to about 20 base pairs.

An exemplary sequence of a nucleic acid construct is shown below. The /5AmMC6/ is a 5' amine modification for attachment to the polymer nanoparticle. The *'s are phosphorothioate bond modifications for stability. The A*G*A*CGTGTGCTCTTCCGATCT (SEQ ID NO: 1001) sequence is the 5' primer binding segment sequence. The GCTACATAAT (SEQ ID NO: 1) is an exemplary barcode polynucleotide sequence. The N's represent the random sequence fragment. The AGATCGGAAGAGCGTCG*T*G*T (SEQ ID NO: 1002) is the 3' primer binding segment sequence.

```
                                    (SEQ ID NO: 1003)
/5AmMC6/A*G*A*CGTGTGCTCTTCCGATCTGCTACA

TAATNNNNNNNNNNNAGATCGGAAGAGCGTCG*T*G*T
```

In all of the various embodiments described above, the entire nucleic acid construct can range in length from about 30 base pairs to about 240 base pairs, about 30 base pairs to about 230 base pairs, about 30 base pairs to about 220 base pairs, about 30 base pairs to about 210 base pairs, about 30 base pairs to about 200 base pairs, about 30 base pairs to about 190 base pairs, about 30 base pairs to about 180 base pairs, about 30 base pairs to about 170 base pairs, about 30 base pairs to about 160 base pairs, about 30 base pairs to about 150 base pairs, about 30 base pairs to about 140 base pairs, about 30 base pairs to about 130 base pairs, about 30 base pairs to about 120 base pairs, from about 30 base pairs to about 110 base pairs, from about 30 base pairs to about 100 base pairs, from about 30 base pairs to about 90 base pairs, from about 30 base pairs to about 80 base pairs, from about 30 base pairs to about 70 base pairs, from about 30 base pairs to about 60 base pairs, from about 30 base pairs to about 50 base pairs, from about 30 base pairs to about 40 base pairs, 40 base pairs to about 120 base pairs, from about 40 base pairs to about 110 base pairs, from about 40 base pairs to about 100 base pairs, from about 40 base pairs to about 90 base pairs, from about 40 base pairs to about 80 base pairs, from about 40 base pairs to about 70 base pairs, from about 40 base pairs to about 60 base pairs, from about 40 base pairs to about 50 base pairs, 50 base pairs to about 120 base pairs, from about 50 base pairs to about 110 base pairs, from about 50 base pairs to about 100 base pairs, from about 50 base pairs to about 90 base pairs, from about 50 base pairs to about 80 base pairs, from about 50 base pairs to about 70 base pairs, from about 50 base pairs to about 60 base pairs, or about 42 base pairs to about 210 base pairs.

The nucleic acid constructs are associated with the polymer nanoparticles, and exemplary polymer nanoparticle to nucleic acid construct ratio ranges are about 20:1 to about 10000:1, about 20:1 to about 9000:1, about 20:1 to about 8000:1, about 20:1 to about 7000:1, about 20:1 to about 6000:1, about 20:1 to about 5000:1, about 20:1 to about 4000:1, about 20:1 to about 3000:1, about 20:1 to about 2000:1, about 20:1 to about 1000:1, about 20:1 to about 900:1, about 20:1 to about 800:1, about 20:1 to about 700:1, about 20:1 to about 600:1, about 20:1 to about 500:1, about 20:1 to about 400:1, about 20:1 to about 300:1, about 20:1 to about 200:1, or about 20:1 to about 100:1.

In one illustrative aspect, the barcoded polymer nanoparticles may be used as delivery vehicles according to the present disclosure. In some embodiments, the non-viral delivery vehicle comprises one or more nanoparticle forming polymers. In some embodiments, the non-viral delivery vehicle comprises polymer nanoparticles. In some embodiments, the non-viral delivery vehicle is not a lipid based system. In some embodiments, the non-viral delivery vehicle comprises polymer nanoparticles made from controlled living/radical polymerization processes. It will be appreciated that the identity of the monomer units is not particularly limited so long as the monomer units being used are compatible with a controlled living/radical polymerization, such as reversible-deactivation radical polymerization, atom transfer radical polymerization (ATRP), reversible addition fragmentation chain transfer polymerization (RAFT), iodine-transfer polymerization (ITP), selenium-centered radical-mediated polymerization, telluride-mediated polymerization (TERP), stibine-mediated polymerization, ring-opening polymerization, or like polymerization processes. In some embodiments, the polymer nanoparticles may be made by RAFT copolymerization to synthesize a diverse set of block copolymers, and to screen their ability to form complexes with a payload. In one aspect, polymer nanoparticles (e.g., RAFT copolymers) may be produced by chemically bonding a payload to a constituent polymer, such as by the grafting of the payload onto RAFT copolymers using chain transfer agents, and subsequently assembling the polymers into a delivery vehicle.

In various embodiments, payloads may be combined with the polymer nanoparticles compositions using any or all of covalent bonds, electrostatic interactions, and ligand affinity interactions. In one aspect, covalent bonding methods include the use of EDC/NHS to form stable amide bonds between the payload and the polymer nanoparticles for improved stability (both "on the shelf" and in vivo), ease of separation and extraction, and sensitive detection. In another illustrative aspect, electrostatic bonding methods include the use of cationic polymer nanoparticles that electrostatically complex with the payload. In another embodiment, ligand affinity bonding includes the use of ligands such as avidin and biotin, both covalently bonded to the polymer nanoparticles and the payload via EDC/NHS chemistry to yield the stable combination of the payload and the polymer nanoparticles.

It will be appreciated that RAFT polymerization is generally known in the art. Suitable reagents, monomers, and conditions for RAFT polymerization previously investigated can be used in the copolymers, methods, and compositions described herein, such as those described in U.S. Pat. Nos. 9,006,193, 9,464,300, and 9,476,063, the disclosures of each of which are incorporated by reference in their entirety.

Chain transfer agents (CTAs) useful in connection with the present disclosure are known in the art. The identity of the CTA is not particularly limited. It will be appreciated that chain transfers steps that form the basis of RAFT polymerization involve a reversible transfer of a functional chain end-group (typically a thiocarbonylthio group, Z—C(═S)S—R) between chains and the propagating radicals. The overall process is comprised of the insertion of monomers between the R— and Z—C(═S)S— groups of a RAFT agent (CTA), which form the α and ω end-group of the majority of the resulting polymeric chains. Suitable CTAs for use in connection with the present disclosure include but are not limited to trithiocarbonates (Z═S-alkyl), dithiobenzoates (Z═Ph), dithiocarbamate (Z═N-alkyl), xanthates (Z═O-alkyl), and the like. (See, Sebastien Perrier, *Macromolecules* 2017 50 (19), 7433-7447) In some embodiments, RAFT copolymerization may be achieved using chain transfer agents (CTAs) containing one or more terminal carboxyl groups in order to obtain carboxy terminated polymers with ends available for bonding to the payload via the methods described above. In this embodiment, when the resulting mono or di-carboxy terminated polymer is dispersed in a low pH (e.g., a pH of less than 6) buffer, both ends of the polymer are exposed and available for labeling via EDC/NHS chemistry. In this embodiment, when the polymer is transferred to a physiological pH (~pH 7), the core blocks self-assemble, encapsulating the payload in the hydrophobic core, to be released and exposed upon acidification in the endosomal compartment of a cell. In some embodiments, the first or second chain transfer agent can be selected from the group consisting of bis(carboxymethyl)trithiocarbonate, bis(2-amino-2-oxoethyl) trithiocarbonate, bis[4-(2-hydroxyethoxycarbonyl)benzyl] trithiocarbonate, 4-cyano-4-(ethylsulfanyithiocarbonyl) sulfanyhmentanoic acid, 4-cyano-4-((phenylcarbonothioyl)thio)pentanoic acid, and 4-cyano-4-[(dodecylsulfanylthiocarbonyl)sulfanyl] pentanoic acid, 4-cyano-4-(thiobenzoylthio)pentanoic acid, 2-cyano-2-propyl benzodithioate, cyanomethyl methyl(phenyl)carbamodithioate, 2-cyano-2-propyl dodecyl trithiocarbonate, 2-(dodecylthiocarbonothioylthio)-2-methylpropionic acid, cyanomethyl dodecyl trithiocarbonate, 2-cyano-2-propyl 4-cyanobenzodithioate, and the like.

It will be appreciated that RAFT useful in connection with the present disclosure can be of a variety of polymer compositions. For example, RAFT polymers useful in connection with the present disclosure can be a randon block polymer comprising a single polymer block, or a diblock RAFT copolymer comprising two polymer blocks, or a triblock RAFT copolymer comprising three polymer blocks, or further numbers of blocks can be used. The skilled person will readily appreciate that the the preparation of block polymers by RAFT polymerization is known in the art and that such polymerization processes can be applied to the present disclosure. (See, Goby, et. al., Nat. Commun. 4:2505 doi: 10.1038/ncomms3505 (2013))

In some embodiments, RAFT copolymers as prepared herein can be described by the following structure:

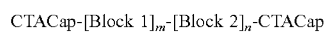

CTACap-[Block 1]$_m$-[Block 2]$_n$-CTACap where each CTACap is a capping unit derived from the chain transfer agent(s) used in the process for preparing the RAFT copolymer. The CTA used for preparing each of Block 1 and Block 2 can be the same or different. In some embodiments, the CTA used to prepare each of Block 1 and Block 2 is the same (e.g. macroCTA). In some embodiments, the CTA used to prepare each of Block 1 and Block 2 is different. In some embodiments, the CTA used to prepare one or both of Block 1 and Block 2 comprises a functional group for the covalent attachment of a biomolecule, drug, or label to the RAFT copolymer. In some embodiments, the covalent attachment can be via an ester or an amide bond. In some embodiments, the covalent attachment can be via EDC-NHS chemistry. In some embodiments, the first capping unit is of the formula

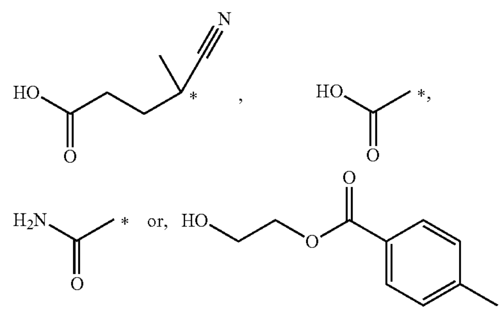

wherein * represents a point of covalent attachment to the first block. In some embodiments, the second capping unit is of the formula

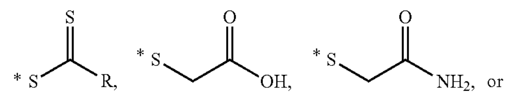

-continued

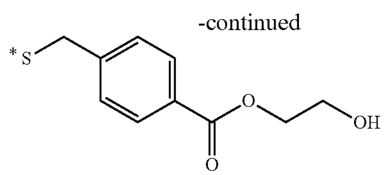

wherein * represents a point of covalent attachment to the second block, and R is —$SC_2$—$C_{12}$ alkyl or $C_6H_5$, In some embodiments, the RAFT copolymer can be associated with a DNA molecule, in particular a nucleic acid construct of the present disclosure, via several methods including, electrostatic interaction, high affinity, non-covalent bond, avidin-streptavidin conjugation, or by direct covalent attachment through, for example, an amide bond. In some embodiments, the RAFT copolymer can be associated with a DNA molecule, in particular a nucleic acid construct of the present disclosure, via electrostatic interaction complexed with a biological molecule. In some embodiments, the RAFT copolymer can be associated with a DNA molecule, in particular a nucleic acid construct of the present disclosure, via electrostatic interaction complexed with a biological molecule. In some embodiments, the RAFT copolymer can be associated with a DNA molecule, in particular a nucleic acid construct of the present disclosure, via a high affinity, non-covalent bond, avidin-streptavidin conjugation. In some embodiments, the RAFT copolymer can be associated with a DNA molecule, in particular a nucleic acid construct of the present disclosure, by direct covalent attachment through, for example, an amide bond.

As shown in FIGS. 5(*a*)-5(*e*), the PNPs described herein can be associated with a nucleic acid construct of the present disclosure via electrostatic interaction, avidin-streptavidin conjugation, or by direct covalent attachment. Briefly, as shown in FIGS. 5(*a*)-5(*e*), the labels provided in the figure are as follows: 001. Polymer nanoparticle (PNP) with positively charged corona in the case of electrostatic loading. 002. Nucleic acid constructs with negative charges due to the phosphate groups. 003. Electrostatically loaded PNP-nucleic acid construct complex. 004. Carboxylate group on the terminal end of the polymer chains in the corona of the PNP. 005. Primary amine group on the 5' end of the amine terminated nucleic acid construct. 006. Phosphate group on the 3' end of the nucleic acid construct. 007. Amide bond formed in the direct amidification reaction between the amine terminal nucleic acid construct and the carboxylate terminated PNP. 008. Primary amine on the biotin bonding protein such as avidin. 010. Amide bond formed between the carboxylate group on the terminal end of the polymer chains in the corona of the PNP and the primary amine on the biotin bonding protein such as avidin. 011. Nucleic acid construct with a biotin functional group on the 5' terminus. 012. Electrostatic coupling reaction that occurs when positively charged PNPs are mixed with negatively charged nucleic acid constructs. 013. Direct amidification reaction that is carried out via an EDA-NHC reaction between the carboxylate group on the terminal end of the polymer chains in the corona of the PNP and the primary amine on the amine terminated nucleic acid constructs. 014 Direct amidification reaction that is carried out via an EDA-NHC reaction between the carboxylate group on the terminal end of the polymer chains in the corona of the PNP and the primary amine on the biotin bonding protein such as avidin. 015. Coupling of the biotin on the 5' end of the nucleic acid construct and the avidin conjugated to the carboxylate terminus on the corona of the PNPs.

In some embodiments, each of Block 1 and Block 2 can comprise one or more monomer units polymerized using a RAFT polymerization process. It will be appreciated that the identity of the monomer units is not particularly limited so long as the monomer units being used are compatible with a controlled living/radical polymerization, such as reversible-deactivation radical polymerization, atom transfer radical polymerization (ATRP), reversible addition fragmentation chain transfer polymerization (RAFT), iodine-transfer polymerization (ITP), selenium-centered radical-mediated polymerization, telluride-mediated polymerization (TERP), stibine-mediated polymerization, ring-opening polymerization, or like polymerization processes. Suitable monomer units include but are not limited to 2-dimethylaminoethyl acrylate (DMAEMA), 2-(diethylamino) ethyl methacrylate (DEAEMA), 2-(diisopropylamino) ethyl methacrylate (DPAEMA), butyl methacrylate (BMA), ethyl acrylic acid (EAA), propyl acrylic acid (PAA), (hydroxyethyl)methacrylate (HEMA), methyl methacrylate (MMA), Acrylic acid (AA), Acetoacetanilide (AAA), 4-Aminobenzonitrile (ABN), 9-Anthracenylmethyl acrylate (ACMA), 9-Anthracenylmethyl methacrylate (ACMMA), Aminoethyl methacrylate (AEM), 2-(2-aminoethylamino) ethyl methacrylate (AEAEMA), 4-(2-Acryloxyethoxy)-2-hydroxybenzophenone (AEHBP), 2-Aminoethyl methacrylate (AEMA), N-(2-Aminoethyl) methacrylamide (AEMAA), 3-amino-2-hydroxypropyl methacrylate (AEAHPMA), 3-aminopropyl methacrylamide (AHPMA), Allyl methacrylate (ALMA), Acrylamide (AM), Amidoamine (AMA), 3-Methacryl amido-3-methylbutanoic acid (AMBA), 2-Allyloxybenzaldehyde (AOBA), [2-(Acryloyloxy)ethyl]trimethylammonium chloride (AOETMA), 3-(Acryloyloxy)-2-hydroxypropyl methacrylate (AOHOPMA), 4-Aminophenethyl alcohol (APA), N-(3-Aminopropyl)methacrylamide (APMA), 5-(3-(Amino)-propoxy)-2-nitrobenzyl methacrylate (APNBMA), N—[N'-(2-aminoethyl)-2-aminoethyl]aspartamide (Asp (DET)), 2-Azidoethyl Methacrylate (AzEMA), 2,2'-Bithiophene (2-2-BTP), tert-Butyl acrylate (BA), Bromoacetaldehyde diethyl acetal (BAADA), N-(t-BOC-aminopropyl) methacrylamide (BAPMAA), tert-Butyl 2-bromoacrylate (BBA), 4-Butylbenzoyl chloride (BBC), 1,3-Butadiene (BD), 2-Butyl-2-ethyl-1,3-propanediol (BEPD), Di-tert-butyl iminodiacetate (BIDA), 3-(Bromomethyl)-5-((trimethylsilyl)ethynyl)benzenesulfonyl fluoride (BMTMSEBS), 2-(Benzyloxy)ethanol (BOE), 4-tert-Butoxystyrene (BOS), Branched polyethyleneimine (BPEI), 3-Bromo-5-((trimethylsilyl)ethynyl)benzenesulfonyl fluoride (BTMSEBS), ε-Caprolactone (CAP), Carboxybetaine methacrylate (CBMA), 2-Cyanoethyl N,N-diisopropylchlorophosphoramidite (CEDPCPP), N-Cyclohexylmaleimide (CHMI), 3-Chloro-2-hydroxypropyl methacrylate (CHPMA), Dodecyl acrylate (DA), N,N-Diallylacrylamide (DAA), Diallylmethylamine (DAMA), Diallyldimethylammonium chloride (DADMAC), 2,5-Diaminopyridine (DAP), 5,5'-Dibromo-4,4'-didodecyl-2,2'-bithiophene (DBDDBT), 5,5'-Dibromo-4,4'-ditetradecyl-2,2'-bithiophene (DBDTBT), 2,5-Dibromo-3-hexylthiophene (DBHTP), Dichloromethylvinylsilane (DCMVS), 2-(Diethylamino)ethanethiol hydrochloride (DEAET), 2-(Diethylamino)ethyl methacrylate (DEAEMA), Diethyl oxalpropionate (DEOP), DL-Lactide (DLL), N,N-dimethylamino-2-ethylmethacrylate) (DMA), N-[3-(N,N-dimethylamino)propyl]-methacrylamide (DMAPMA), [2-(Methacryloyloxy)ethyl]dimethyl-(3-sulfopropyl)ammonium hydroxide (DMAPS), N,N'-dimethylbutylamine (DMBA), N,N'-dimethylethanolamine (DMEA), N,N-dimethylamino-2-ethylacrylate or 2-(dimethylamino)ethyl acrylate (DMAEA), 1-(Dimethylamino)pyrrole (DMAP), 4,5-Dimethoxy-2-nitrobenzyl alcohol (DMONBA),3,4-Dimethoxythiophene (DMOT), 1,2-Dimyristoyl-sn-glycero-3-phosphocholine (DMPC), 2-deoxy-2-methacrylamido glucopyranose (DOMAAG), 1,2-Dioleoyl-sn-glycero-3-phosphocholine (DOPC), 1,2-Dioleoyl-sn-glycero-3-phosphoethanolamine (DOPE), 1,4,7,10-Tetraazacyclododecane-1,4,7,10-tetraacetic acid (DOTA), 1,2-Dioleoyl-3-trimethylammonium Propane (DOTAP), 1,2-Diphytanoyl-sn-glycero-3-phosphoethanolamine (DPyPE), 3-Dodecylthiophene (3-DT), N42-(2-pyridyldithio)lethyl methacrylamide (DTEMA), Ethyl acrylic acid (EAA), Ethyl 2-(bromomethyl)acrylate (EBMA), Ethyl 1-cyano-1-cyclopropanecarboxylate (ECCPC), 3,4-Ethylenedioxythiophene (EDOT), Ethylene glycol dimethacrylate (EGDMA), Ethylene glycol phenyl ether acrylate (EGPEA), Ethyl methacrylate (EMA), 3-(Fluorosulfonyl)-5-((trimethylsilyl)ethynyl)benzoic acid (3FTMSEBA), 3-Formyl-5-((trimethylsilyl)ethynyl)benzenesulfonyl fluoride (3FTMSEBS), 4-Formyl-2-((trimethylsilyl)ethynyl)benzenesulfonyl fluoride (4FTMSEBS), 5-Fluoro-2,3-thiophenedicarboxaldehyde (SFTPDCA), N-acetyl-D-galactose (GalNAc), N-acetyl-D-glucose (GlcNAc), Glycidyl methacrylate (GMA), Glycosylphosphatidylinositol (GPI), 5,7-Hexadecadiynoic acid (HDDA), 2-Hydroxyethyl methacrylate (HEMA), 1,1,1,3,3,3-Hexafluoroisopropyl acrylate (HFIPA), 1,1,4,7,10,10-Hexamethyltriethylenetetramine (HMTETA), 4-Hydroxybutyl acrylate (HOBA), 2-(4-Hydroxyphenylazo)benzoic acid (HPABA), 2,2,3,3,4,4,4-Heptafluorobutyl acrylate (HPFBA), N-(2-Hydroxypropyl)-Methacrylamide (HPMA), 2,2,3,4,4,4-Hexafluorobutyl acrylate (HXFBA), Isobornyl acrylate (IBA), 4-Iodobenzoyl chloride (IBC), Isobornyl methacrylate (IBMA), N-(Isobutoxymethyl)acrylamide (IBMAA), Isodecyl acrylate (IDA), Maleic anhydride (MA), [2-(Methacryloyloxy)ethyl]trimethylammonium chloride (MAETMA), Methacryloyl-L-Lysine (MAL), Methacryloxysuccinimide (MAS), Methacrylamidotrehalose (MAT), Methyl heptadecanoate (MHD), 1-Methyl-1H-indole-3-carbaldehyde (MICA), 2-N-Methylmaleimide (MMI), Methyl-5-norbornene-2,3-dicarboxylic anhydride (MNDCA), Methoxyethyl methacrylate (MOEMA), 2-(2-Methoxyethoxy)ethyl methacrylate (MOEOEMA), 3-Methyl-3-oxetanemethanol (MOM), 2-Methacryloyloxyethyl phosphorylcholine (MPC), Methyl 4-vinylbenzoate (MVB), 2-Naphthyl acrylate (NA), N-(Acryloxy)succinimide (NAS), o-Nitrobenzyl methacrylate (NBMA), N-Hydroxysuccinimide (NHS), N-(Methacryloxy) succinimide methacrylate (NHSMA), N-Isopropylacrylamide (NIPAM), 2-Naphthyl methacrylate (NMA), N-(Methacryloyloxy)succinimide (NMS), N-(n-Octadecyl)acrylamide (NODAA), 4-Nitro-N-propylbenzylamine hydrochloride (NPBAHC), Oligoethylene glycol methacrylate (OEGMA), Oligoethylenimine (OEI), 3-Phenylthiophene (3-PTP), Poly(N-methyl 4-vinylpyridine iodide) (P4VPQ), Poly(2-aminoethylmethacrylamide) (PAEMA), N—(N'—{N"—[N"'-(2-aminoethyl)-2-aminoethyl]-2-aminoethyl}-2-aminoethyl)-aspartamide (Asp(TEP)), 4-Pentenoic anhydride (PAN), Pentabromobenzyl acrylate (PBBA), Pentabromobenzyl methacrylate (PBBMA), Pentabromophenyl acrylate (PBPA), Pentabromophenyl methacrylate (PBPMA), Poly (ε-caprolactone) (PCL), trans-2-Phenylcyclopropyl isocyanate (PCPI), 1,5-Pentanediol (PD), 2-Phenyl-1,3-dioxan-5-ol (PDO), Pyridyl disulfide ethyl methacrylate (PDSEMA), Poly(ethylene glycol) (PEG), Poly(ethylene glycol) acrylate (PEGA), Poly(ethylene glycol) methyl ether methacrylate (PEGMEMA, Poly(ethylene glycol) ethyl ether methacrylate (PEGEEMA), Poly(ethylene glycol) methacrylate (PEGMA), Pentaethylenehexamine (PEHA), Poly(ethylenimine) (PEI), Pentaerythritol tetraacrylate (PETA), Pentafluorophenyl (PFP), Pentafluorophenyl acrylate (PFPA), Pentafluorophenyl methacrylate (PFPMA), Poly(glutamic acid) (PGA), Poly-(glycoamidoamine) (PGAA), Poly(glycidylbutylamine) (PGBA), Poly(glycidyl methacrylate) functionalized with ethanolamine (PGEA), Poly(glycidyl methacrylate) (PGMA), Poly(N-(2-Hydroxypropyl)methacrylamide) (PHPMA), Poly(lactic acid) (PLA), Poly(L-glutamate), (PLG), Poly(lactic-co-glycolic acid) (PLGA), Poly(L-lysine) (PLL), Poly(L-lactic acid) (PLLA), Poly (lauryl methacrylate) (PLMA), Poly(methacrylic acid) (PMAA), Poly-(2-deoxy-2-methacrylamido glucopyranose) (PMAG), Poly-(methyl methacrylate) (PMMA), Poly(2-methacryloyloxyethyl phosphorylcholine) (PMPC), Poly[N-(3-(methacryloylamino) propyl)-N,N-dimethyl-N-(3-sulfopropyl) ammonium hydroxide] (PMPD), Poly(n-butyl acrylate) (PnBA), Poly(n-butyl methacrylate) (PnBMA), Poly(N-isopropyl acrylamide) (PNIPAM), Poly(oligoethylene glycol methacrylate) (POEGMA), Poly(propylene glycol) (PPG), Poly(propylenimine) (PPI), 3,4-Propylenedioxythiophene (ProDOT), Poly(styrene) (PS), Poly(sodium 4-styrenesulfonate) (PSS), Poly(tributyl-(4-vinylbenzyl) phosphonium chloride) (PTBP), Poly(triethyl-(4-vinylbenzyl)phosphonium chloride) (PTEP), Poly((2-trimethylamino)ethyl metacrylate chloride) (PTMAEMA), Poly((vinylbenzyl) trimethylammonium) (PVBTMA), Poly(2-vinyl-4,4-dimethylazlactone) (PVDMA), Poly(N-ethyl-4-vinylpyridinium bromide) (PVP), Quaternized Poly-DMAEMA (QPDMAEMA), Sulfobetaine methacrylate (SBMA), 3-Sulfopropyl methacrylate potassium salt (SPMAP), Thiocholesterol (TC), Thiophene-2,5-diboronic acid bis(pinacol) ester (TDABP), Triethylene glycol dimethacrylate (TEGDMA), Trifluoroethylene (TFE), 2,2,2-Trifluoroethyl acrylate (TFEA), 2,2,2-Trifluoroethyl methacrylate (TFEMA), Tetrahydrofurfuryl acrylate (THFA), Triallylisocyanurate (TIC), Trimethylene Carbonate (TMC), 4,4'-Trimethylenedipiperidine (TMDP), Trimethylolpropane tris(3-mercaptopropionate) (TMPTMP), (Trimethylsilyl) methacrylate (TMSMA), Triphenylcarbenium pentachlorostannate (TPCPCS), 3-Vinylbenzaldehyde (3VBA), 4-Vinylpyridinium chloride (4VP), Vinyl acrylate (VA), Vinyl acetate (VAT), 4-Vinylbenzoic acid (VBA), (Vinylbenzyl)trimethylammonium chloride (VBTAC), 1-Vinylimidazole (VI), 1-Vinyl-2-pyrrolidone (VP), m-Xylylenediamine (XDA), Zinc stearate (ZS), and the like.

In some embodiments, the monomer units used to make Block 1 and/or Block 2 of RAFT copolymers as described herein are selected from the group consisting of 2-(dimethylamino) ethyl acrylate (DMAEEA), 2-(diethylamino) ethyl methacrylate (DEAEEA), 2-(diisopropylamino) ethyl methacrylate (DIEAMA), butyl methacrylate (BMA), ethyl acrylic acid (EAA), propyl acrylic acid (PAA), (hydroxyethyl)methacrylate, and methyl methacrylate (MMA).

In some embodiments, the RAFT copolymers provided herein can be described by the formula:

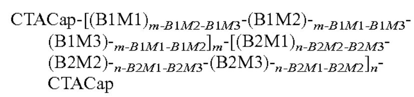

$$\text{CTACap-[(B1M1)}_{m\text{-}B1M2\text{-}B1M3}\text{-(B1M2)-}_{m\text{-}B1M1\text{-}B1M3}\text{-(B1M3)-}_{m\text{-}B1M1\text{-}B1M2}]_{m}\text{-[(B2M1)}_{n\text{-}B2M2\text{-}B2M3}\text{-(B2M2)-}_{n\text{-}B2M1\text{-}B2M3}\text{-(B2M3)-}_{n\text{-}B2M1\text{-}B2M2}]_{n}\text{-CTACap}$$

For example, a RAFT copolymer as described herein having a single monomer in Block 1 of 25 units and 3 different monomers in Block 2 having an average monomer unit ratio of 20:10:5 for a total n of 35, can be described by the general formula

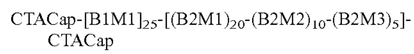

$$\text{CTACap-[B1M1]}_{25}\text{-[(B2M1)}_{20}\text{-(B2M2)}_{10}\text{-(B2M3)}_{5}\text{]-CTACap}$$

It will be further appreciated that the polymers prepared using a RAFT polymerization are random polymers having a distribution of units and hence molecular weights. Therefore, the cartoon representation of Block 2 in the example above is a random copolymer comprising 35 monomer units of B2M1, B2M2, and B2M3 in the ratio described above.

In another illustrative embodiment, the polymer nanoparticle composition can be coated with one or more polymers to protect the compositions from immune responses or to enhance endosomal escape. In one embodiment, the one or more polymers comprise polyethylene glycol. In another embodiment, the one or more polymers comprise polyethylene glycol poly-L-lysine. In yet another embodiment, the one or more polymers comprise polyethylenimine. In an additional embodiment, the one or more polymers comprise polyethylene glycol poly-L-lysine and polyethylenimine.

It will be appreciated that tuning the parameters and properties of the RAFT copolymers described herein can be advantageous to their use in the compositions and methods as described herein. Accordingly, the methods for preparing RAFT copolymers either in singleton or in library format as described herein are capable of providing particular parameters and properties of the RAFT copolymers.

In some embodiments, a RAFT block polymer as described herein has one or more of an overall molecular weight ($M_n$) (i.e. the total of all blocks) in the range of about 1 kDa to about 1000 kDa, or about 2 kDa to about 500 kDa, or about 2 kDa to about 160 kDa, and overall degree of polymerization in the range of about 10 to about 3500, or about 20 to about 2500, or about 30 to about 900, a size in the range of about of about 10 nm to about 10000 nm, and a maximum corona-to-core ratio (CCR) of about 1 to about 4. In some embodiments, the overall molecular weight ($M_n$) in the range of about 30 kDa to about 120 kDa, about 40 kDa to about 110 kDa about 50 kDa to about 100 kDa, about 60 kDa to about 90 kDa, about 40 kDa to about 80 kDa, and about 40 kDa to about 60 kDa. In some embodiments, the overall degree of polymerization in the range of about 40 to about 850, about 60 to about 800, about 100 to about 700, about 200 to about 600, or about 300 to about 500. In some embodiments, the size is in the range of about of about 10 nm to about 10000 nm, or about 20 nm to about 5000 nm, or about 50 nm to about 3000 nm, or about 20 nm to about 1000 nm, or about 50 nm to about 1000 nm, or about 30 nm to about 500 nm, or about 200 nm to about 2000 nm, or about 100 nm to about 5000 nm, or about 100 nm to about 500 nm, or about 10 nm to about 50 nm, about 15 nm to about 45 nm, about 20 nm to about 40 nm, or about 25 nm to about 35 nm. In some embodiments, the maximum corona-to-core ratio (CCR) is less than 4, or less than 3, about 1 to about 3.8, about 1.2 to about 3.5, about 1.5 to about 3, about 1.5 to about 2.5, or about 1 to about 2.

In some embodiments, a first block can be prepared from one or more monomer units and have a molecular weight ($M_n$) in the range of about 1 kDa to about 500 kDa, or about 10 kDa to about 200 kDa, or about 10 kDa to about 160 kDa, or about 1 kDa to about 80 kDa, and a degree of polymerization in the range of about 10 to about 3500, or about 10 to about 2500, or about 20 to about 2000, or about 50 to about 1200, or about 50 to about 1000. In some embodiments, a first block molecular weight ($M_n$) can be in the range of about 1 kDa to about 500 kDa, or about 2 kDa to about 400 kDa, or about 5 kDa to about 200 kDa, or about 10 kDa to about 160 kDa, or about 15 kDa to about 100 kDa, or about 25 kDa to about 60 kDa, or about 30 kDa to about 55 kDa, about 30 kDa to about 50 kDa, or about 30 kDa to about 40 kDa, and the like. In some embodiments, the first block degree of polymerization is in the range of about 30 to about 350, about 50 to about 300, about 70 to about 250, about 80 to about 240, about 100 to about 200, and the like.

In some embodiments, the second block can be prepared from one or more monomer units, and can have a molecular weight ($M_n$) in the range of about 1 kDa to about 500 kDa, or about 10 kDa to about 200 kDa, or about 10 kDa to about 160 kDa, or about 1 kDa to about 80 kDa, and a degree of polymerization in the range of about 10 to about 3500, or about 10 to about 2500, or about 20 to about 2000, or about 50 to about 1200, or about 50 to about 1000. In some embodiments, the second block molecular weight ($M_n$) is in the range of about 10 kDa to about 70 kDa, about 15 kDa to about 65 kDa, about 20 kDa to about 60 kDa, about 25 kDa to about 55 kDa, about 30 kDa to about 50 kDa, about 35 kDa to about 45 kDa, about 5 kDa to about 15 kDa, and the like. In some embodiments, the second block degree of polymerization is in the range of about 3 to about 2500; or about 20 to about 2000, or about 30 to about 1500, or about 40 to about 1200, or about 10 to about 500, or about 12 to about 450, or about 20 to about 400, or about 25 to about 350, or about 50 to about 300, or about 100 to about 250, or about 150 to about 200, or about 5 to about 50, or about 5 to about 20, and the like.

In some embodiments, a third, fourth, or subsequent block can be prepared from one or more monomer units, and each can have a molecular weight ($M_n$) in the range of about 1 kDa to about 500 kDa, or about 10 kDa to about 200 kDa, or about 10 kDa to about 160 kDa, or about 1 kDa to about 80 kDa, and a degree of polymerization in the range of about 10 to about 3500, or about 10 to about 2500, or about 20 to about 2000, or about 50 to about 1200, or about 50 to about 1000. In some embodiments, the third, fourth, or subsequent block molecular weight ($M_n$) is in the range of about 10 kDa to about 70 kDa, about 15 kDa to about 65 kDa, about 20 kDa to about 60 kDa, about 25 kDa to about 55 kDa, about 30 kDa to about 50 kDa, about 35 kDa to about 45 kDa, about 5 kDa to about 15 kDa, and the like. In some embodiments, the third, fourth, or subsequent block degree of polymerization is in the range of about 3 to about 2500; or about 20 to about 2000, or about 30 to about 1500, or about 40 to about 1200, or about 10 to about 500, or about 12 to about 450, or about 20 to about 400, or about 25 to about 350, or about 50 to about 300, or about 100 to about 250, or about 150 to about 200, or about 5 to about 50, or about 5 to about 20, and the like.

In some embodiments, a single chain transfer agent can be used in the RAFT polymerization process in connection with the present disclosure. In some embodiments, for a block polymer having more than one block, one or more single chain transfer agents can be used in the RAFT polymerization process in connection with the present disclosure. In some embodiments, for a block polymer having two blocks, a first chain transfer agent and a second chain transfer agent (which can be the same or different) can be used at each step of the RAFT polymerization process in connection with the present disclosure. In some embodiments, for a block polymer having three blocks, a first chain transfer agent, a second chain transfer agent, and a third chain transfer agent (which can be the same or different) can be used at each step of the RAFT polymerization process in connection with the present disclosure.

It will be appreciated that a variety of solvents can be used in the RAFT polymerization method steps and purification steps described herein. Suitable solvents include, but are not limited to, 2-Chloroethanol, Acetic Acid (Glacial), Acetone, Acetonitrile, Acetophenone, Aniline, Benzaldehyde, Benzyl Acetate, Carbon disulfide, Cyclohexane, Cyclohexanol, Di(ethylene glycol), Di(propylene glycol), Diacetone alcohol, Diethyl ether, Dimethylsulfoxide, Ethanol, Ethyl acetate, Ethylene glycol, Formaldehyde (37% solution), Formamide, Formic acid, Formic acid (96%), Hexanelsobutanol, Isopropanol, Isopropyl acetate, Isopropyl ether, m-Cresol, Methanol, Methyl acetate, Methyl ethyl ketone, Mineral Oil, N,N-Dimethylformamide, n-Butanol, n-Octane, n-Propanol, Propylene glycol, Pyridine, t-Butanol, Tetrahydrofuran, Trifluoroacetic acid, water, and the like, and combinations thereof.

In some embodiments, the one or more nanoparticle forming polymers are RAFT block copolymers comprising a. a first terminus comprising a first capping unit derived from a first chain transfer agent in a RAFT copolymerization process;

b. a first block prepared from one or more monomer units covalently attached to the first reactive functional unit, and having a molecular weight ($M_n$) in the range of about 1 kDa to about 500 kDa and a degree of polymerization in the range of about 10 to about 2500;

c. optionally a second block prepared from one or more monomer units covalently attached to the first block, and having a molecular weight ($M_n$) in the range of about 1 kDa to about 500 kDa and a degree of polymerization in the range of about 10 to about 2500;

d. optionally a third block prepared from one or more monomer units covalently attached to the first and/or second blocks, and having a molecular weight ($M_n$) in the range of about 1 kDa to about 500 kDa and a degree of polymerization in the range of about 10 to about 2500;

e. optionally a fourth block prepared from one or more monomer units covalently attached to the first, second, and/or third blocks, and having a molecular weight ($M_n$) in the range of about 1 kDa to about 500 kDa and a degree of polymerization in the range of about 10 to about 2500;

f. optionally a fifth block prepared from one or more monomer units covalently attached to the first, second, third, and/or fourth blocks, and having a molecular weight ($M_n$) in the range of about 1 kDa to about 500 kDa and a degree of polymerization in the range of about 10 to about 2500; and g. a second terminus comprising a second capping unit derived from a first, a second, a third, or a fourth chain transfer agent.

Illustrative payloads for the polymer nanoparticle described herein can include any one or a combination of compositions selected from the group comprising: nucleic acids (e.g., DNA or RNA), pDNA, oligodeoxyribonucleic acids (ODNs), dsDNA, ssDNA, antisense oligonucleotides, antisense RNA, siRNA, messenger RNA, guide RNA (e.g., small guide RNA), ribonucleoproteins, donor DNA strands used in the CRISPR/Cas9 system, and enzymes, such as CRISPR-associated enzymes, e.g., Cas9, enzymes used in other gene editing systems, such as ZFNs, custom designed homing endonucleases, TALENS systems, other gene editing endonucleases, and reverse transcriptase.

In another aspect, the present disclosure rapidly identifies top candidates using a machine learning model. In the illustrative embodiment, a graph neural network (GNN) is used for this process. Polymers can be characterized at three scales: monomer, block, and full polymer. Monomers combine to form blocks, and blocks combine to form full polymers. Polymer properties are dependent on characteristics of the polymer at all three scales. The relationships between monomers, blocks, and polymers can be captured with a directed graph. Information can then be shared between nodes in the graph to create a numerical representation of the full polymer at all three scales: monomer, block, and polymer. These numerical representations can then be used in a neural network to prediction properties of the polymer. The use of a GNN for polymer property prediction in the illustrative embodiment provides two primary benefits: first, the graph can model polymer characteristics at all three scales which is important for accurate prediction; second, the graph provides a flexible modeling structure that can accommodate several polymer structures.

Figure 3A:
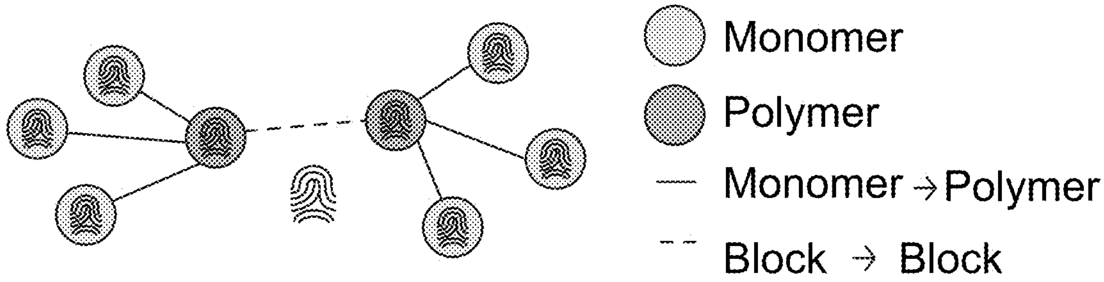
FIG. 3(*a*)-3(*b*) are schematic diagrams showing graph neural network architecture (3(*a*)) and Zeta potential prediction from SMILES input (3(*b*)).

The machine learning model is first trained on a combination of public data and preliminary testing data, supplemented with the large data sets described above. The illustrative embodiment involves a three-loop deep learning cycle to accelerate high-throughput characterization and screening for PNPs. The three deep learning loops characterize the PNP physical properties, in vitro bioactivity, and in vivo bioactivity, respectively. Each loop utilizes a GNN deep learning model (see FIG. 3*a*) to characterize the candidate PNPs. The GNN takes the simplified molecular-input line-entry system (SMILES) strings defining the monomers as an input (the nodes of the graph), and the edges of the graph define the relationship between the monomers and how they combine to form the PNP. The edges of the graph also allow additional information about the polymer (e.g., ratios of monomers and degree of polymerization) to be incorporated into the GNN.

Figure 3B:
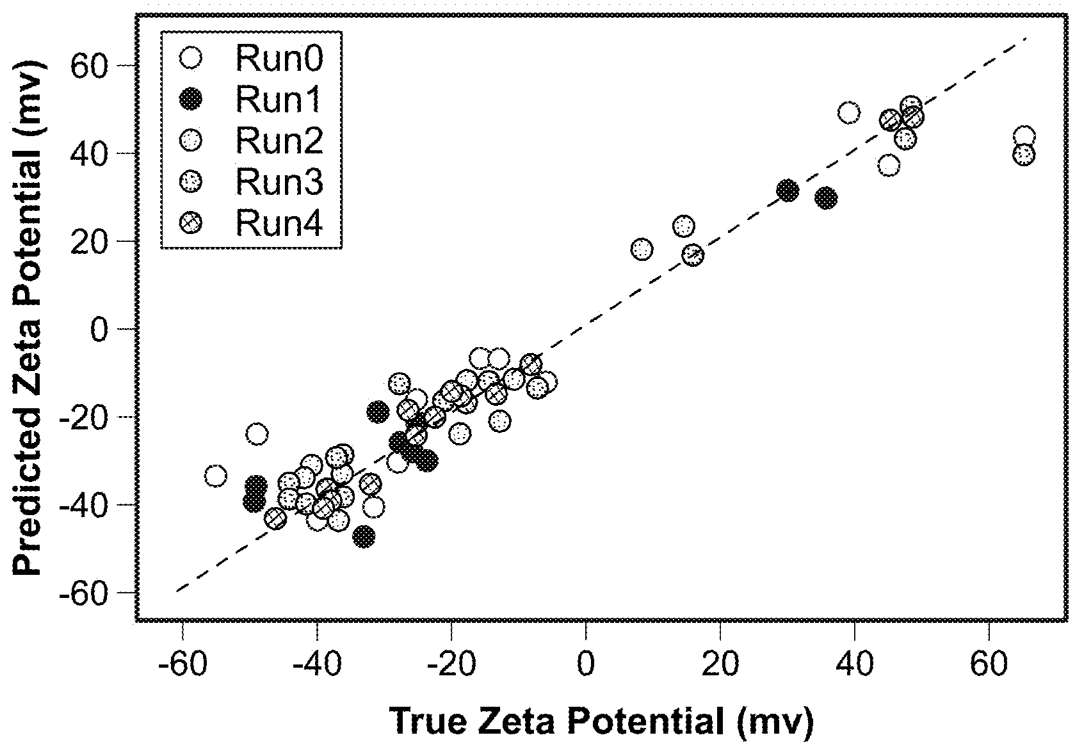

The presently disclosed architecture offers at least three distinct advantages. First, the deep learning model is not dependent on polymer fingerprinting. Rather, the deep learning model will learn an appropriate numerical embedding from the SMILES strings. Second, the graph allows the model the flexibility to represent various families of PNPs with ease. Third, using SMILES strings as inputs allows the limited training dataset to be augmented with enumerated SMILES strings, increasing the amount of training data available and improving the model performance. Testing of this GNN architecture has shown impressive ability to predict zeta potential (see FIG. 3*b*), a critical characteristic for non-viral gene delivery vehicles. Once trained, these deep learning models will be used to prioritize the synthesis and characterization of candidate PNPs in the high-throughput system to meet the requirements of a bioactivity. Iterative data can be used to fine-tune the models in an active learning cycle to improve future performance.

In some embodiments, data augmentation may be performed to artificially increase the size and variety of the data used to train the machine learning model (and, consequently, increase model performance). Deep learning models require relatively large datasets for training and can over-fit to small datasets. As discussed above, the GNN takes the SMILES strings defining the monomers as an input. A monomer (a building block of a polymer) has a single canonical SMILES string, but it also has multiple alternative SMILES string representations. SMILES enumeration can be performed to generate these alternative forms from the canonical SMILES string and, thus, increase the size of the training data set many times over. The neural network model is then able to leverage this increase in data size and variety of representations to improve performance.

In other embodiments, a modified Transformer model (rather than a GNN) may be used to predict polymer properties (and, thus, rapidly identify top candidates for non-viral carriers for delivering base editing proteins, among other applications). The modified Transformer model exploits relative positional information of inputs to create numerical embeddings for monomer string inputs. These numerical embeddings can then be used in deep learning and statistical models for polymer property prediction. Additionally, the Transformer model is more computationally efficient compared to many other deep learning architectures that can process sequential data. The original Transformer architecture consists of an encoding and decoding architecture. The encoder takes an input sequence of data and outputs a high dimensional embedding, while the decoder takes the high dimensional embedding as an input and tries to predict the original or similar sequence to the one input into the encoder. The present disclosure does not need to predict a sequential output, so it only uses the encoding portion of the Transformer to predict polymer properties, both physical and in-vitro/in-vivo.

In yet another aspect, an illustrative embodiment of the present disclosure allows for the selection the top candidates for PNP-mediated delivery of the SOD1-targeting CBE in a mouse model of ALS. Functional gene editing tests in a microglial cell line stably expressing EGFP or SOD1 can then be performed using these top candidates. Moreover, the efficacy and safety PNP-mediated CBE delivery can be assessed in the G93A-SOD1 mouse model of ALS. Prior success of CBE base editors for slowing ALS progression in mice shows a likelihood that they can also lead to clinical translation of a novel ALS gene editing therapy.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected. There exist a plurality of advantages of the present disclosure arising from the various features of the apparatus, systems, and methods described herein. It will be noted that alternative embodiments of the apparatus, systems, and methods of the present disclosure may not include all of the features described, yet still benefit from at least some of the advantages of such features. Those of ordinary skill in the art may readily devise their own implementations of the apparatus, systems, and methods that incorporate one or more of the features of the present disclosure.

EXAMPLES

Example 1

Barcode Design

Figures 4, 5A, 5B, 5C:
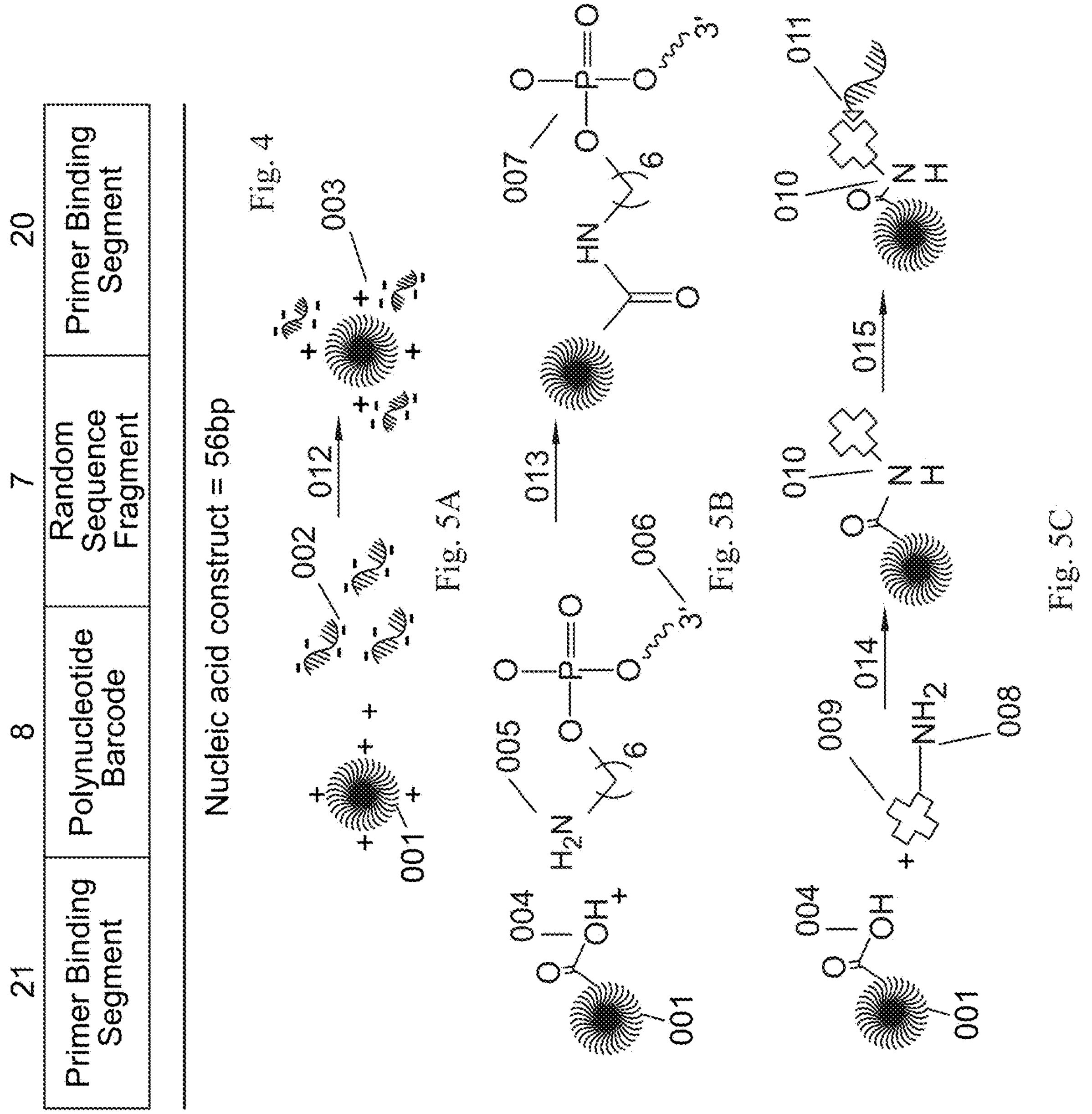
FIG. 4 is an illustration of one representative example of a nucleic acid construct of the present disclosure, showing the length (in base pairs (bp)) of the primer binding segments (20 bp and 21 bp in the construct shown), the polynucleotide barcode (8 bp in the construct shown), and the random sequence fragment (7 bp in the construct shown) of the present disclosure.

The nucleic acid constructs used in this example comprised a unique portion comprising 8-10 nucleotides in the center of the polynucleotide, the unique portion further constrained by the requirement of a hamming distance of at least 3 bases from any other barcodes to be pooled. Directly on the 3' end of the barcode, 7-10 random bases are included for bioinformatic removal of PCR duplicates. This central sequence is flanked by universal primer annealing sites containing overhangs for the addition of index adapters during sequencing library preparation. FIG. 4 shows a representative illustration of these barcodes. These nucleic acid constructs were designed with either a biotin functional group or an amine functional group on the 5' end.

Example 2

Polymer Nanoparticle Synthesis

A diblock copolymer was synthesized as described in PCTapp349529(21477779.1) using reversible addition-fragmentation chain transfer (RAFT) polymerization with reagents and amounts listed in Table 2. Block 1 reagents were combined in a round bottom flask, purged with argon, and heated to 60° C. for 6 hours using a heating mantle. The reaction product was purified using four 80:20 pentane:ether precipitation washes and centrifugation cycles and dried in vacuo. The Block 1 product was used as the macroRAFT agent for Block 2, and the calculated reagent volumes (as calculated based on theoretical molecular weight information for Block 1) were combined in a round bottom for the Block 2 reaction. The reaction mixture was argon purged before being heated at 60° C. for 24 hours. The reaction product was purified using the same purification process and dried in vacuo. The resulting polymer was dialyzed in deionized water for 4 days with multiple water changes each day. Finally, the dialyzed material was lyophilized for 4 days and stored at room temperature for experimental use.

TABLE 2

Reagents and amounts used to synthesize barcoded PNPs

| Reagent | Purpose | Lot 0001 Amount | Lot 0002 Amount |
|---|---|---|---|
| Block 1 | | | |
| 2-dimethylaminoethyl acrylate (DMAEMA) | Monomer | 15999.6 mg | 32000.0 mg |
| (4-cyano-4-(((ethylthio)carbonothioyl)thio)pentanoicacid) (ECT) | Chain transfer agent | 76.9 mg | 153.7 mg |
| Azobisisobutyronitrile (AIBN) | Initiator | 9.5 mg | 19.05 mg |
| Dimethylformamide (DMF) | Solvent | 24131.1 mg | 48229.8 mg |
| Block 1 Reaction Yield | % Yield | 31.75% | 39.55% |
| Block 2 | | | |
| 2-dimethylaminoethyl acrylate (DMAEMA) | Monomer | 713.0 mg | 2110.6 mg |
| butyl methacrylate (BMA) | Monomer | 1934.4 mg | 5727.6 mg |
| propyl acrylic acid (PAA) | Monomer | 518.2 mg | 1540.1 mg |
| Block 1 macroRAFT agent, meaning ECT + DMAEMA. The ECT end groups (R & Z) were still present to perform their function, but they were on the end of the p(DMAEMA) polymer synthesized as block 1. For reference, here is ECT R & Z groups on either side of onyl group. | Macro Chain transfer agent | 1528.4 mg | 4526.2 mg |

TABLE 2-continued

| Reagents and amounts used to synthesize barcoded PNPs | | | |
|---|---|---|---|
| Reagent | Purpose | Lot 0001 Amount | Lot 0002 Amount |
| ECT<br>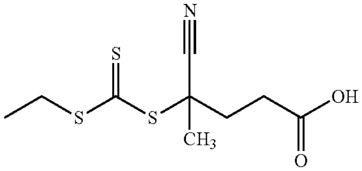<br>Z R | | | |
| Azobisisobutyronitrile (AIBN) | Initiator | 1.7 mg | 4.93 mg |
| Dimethylformamide (DMF) | Solvent | 7045.0 mg | 20828.8 mg |
| Block 2 Reaction Yield | % Yield | 73.33% | 70.99% |

Example 3

Figure 6:
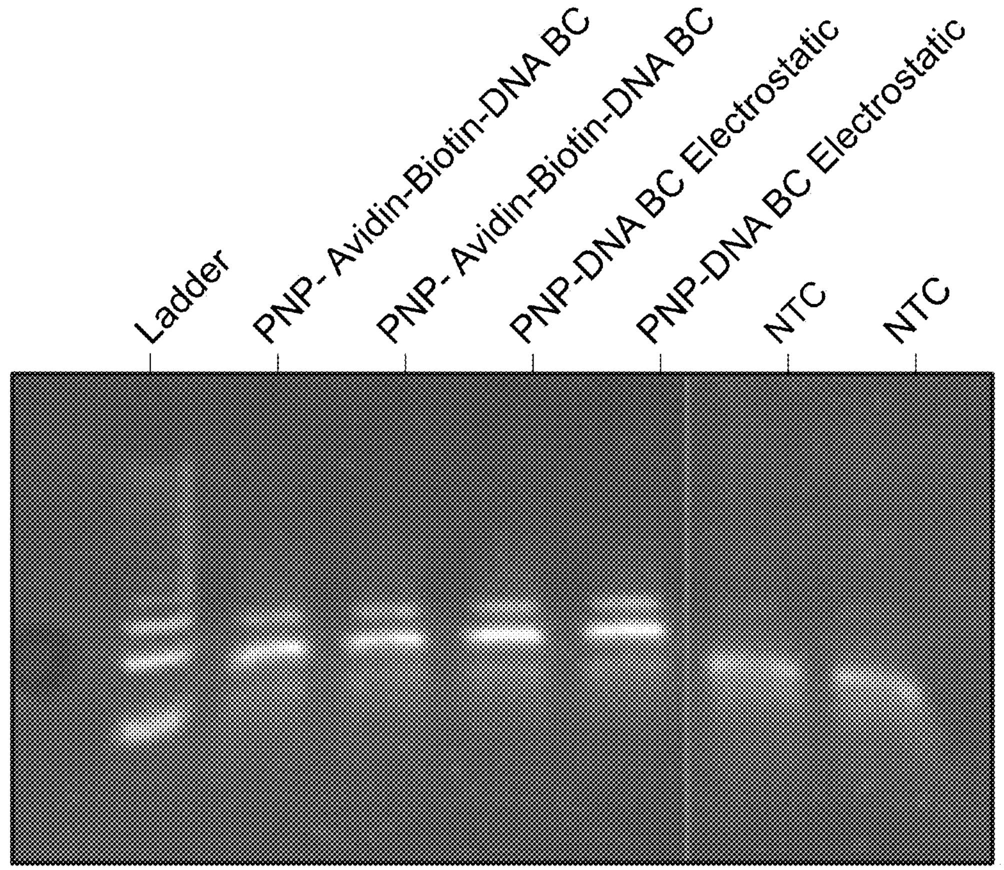
FIG. 6 is an e-gel showing amplification of nucleic acid constructs electrostatically bound to polymer nanoparticles. The presence of the double band in the samples with nucleic acid construct confirms that the barcodes were attached to the PNP. The absence of the double band in the not test control (NTC) validates the positive result.

Composition Example 1 (CE1): Electrostatic Attachment of Nucleic Acid Constructs (Containing DNA Barcodes) to Polymer Nanoparticles RAFT copolymers were synthesized according to the methods above and the reagents listed in Table 2. The polymer was dispersed in phosphate buffered saline at a concentration of ~5 mg/ml. For electrostatic loading (FIG. 5*a*), nucleic acid constructs (according to the design shown in FIG. 4 including polynucleotide barcodes) were dissolved in tris EDTA buffer at a concentration of ~100 μM (~1.9 mg/mL). These stock solutions were mixed together with PBS to produce a solution with a final concentration of 0.05 mg/mL polymer and 0.00389 mg/mL nucleic acid construct. They were incubated at room temperature for at least 30 minutes to allow the positively charged polymer to associate with the negatively charged nucleic acid constructs. The sample was transferred to an amicon ultra-4 centrifuge tube (MWCO 30 kDa). (Max 3.5 mL/Tube) and centrifuged at 4,000×g for 15 minutes to remove any unbound nucleic acid constructs. The filtrate (containing unbound nucleic acid constructs) was discarded and sterile PBS was added to the retentate to final concentration of 0.05 mg/mL polymer and 0.00389 mg/mL nucleic acid constructs. The electrostatically bound nucleic acid constructs were amplified via PCR, using primers designed to bind to the universal primer binding segments on the nucleic acid constructs. The amplicons were detected via gel electrophoresis on agarose gel. The presence of a double band (FIG. 6) in a lane indicates the presence of amplicons, showing that nucleic acid constructs were bound to the PNPs.

Example 4

Figure 7:
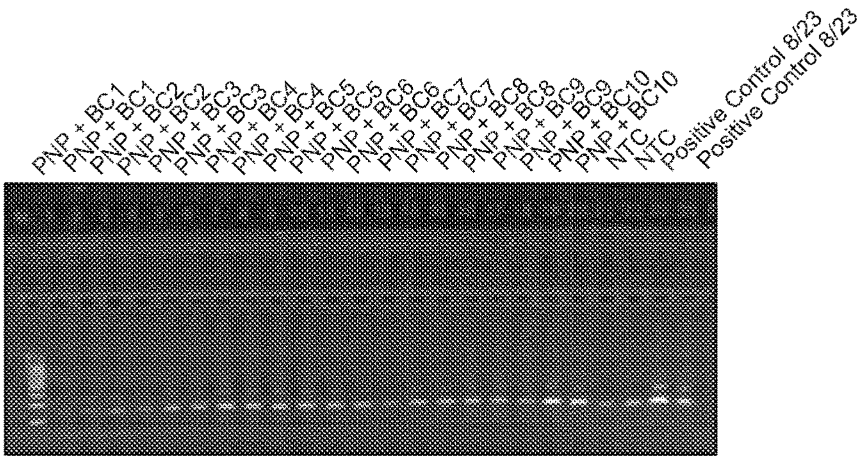
FIG. 7 is a series of e-gels showing DNA barcode amplification from a pooled sample of 96 unique barcodes, each attached to a prototype PNP. Each frame in the figure is one row of a 48 channel gel electrophoresis. The first column of each gel is a DNA latter, the bottom band of which is ~100 bases. The bright band in each column near the 100 bp mark indicates amplicons coming from the barcodes.
Figure 7:
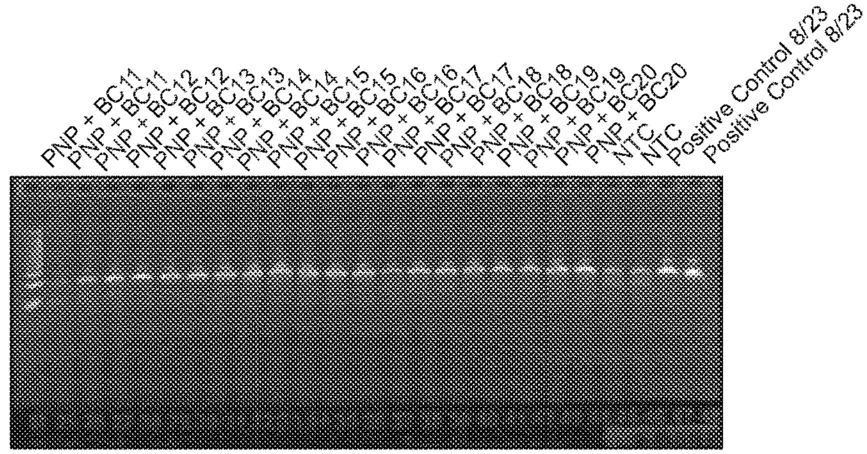
Figure 7:
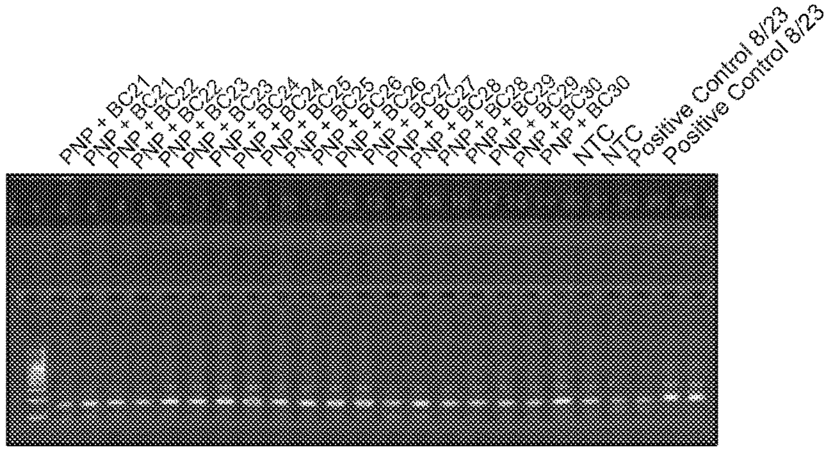
Figure 7:
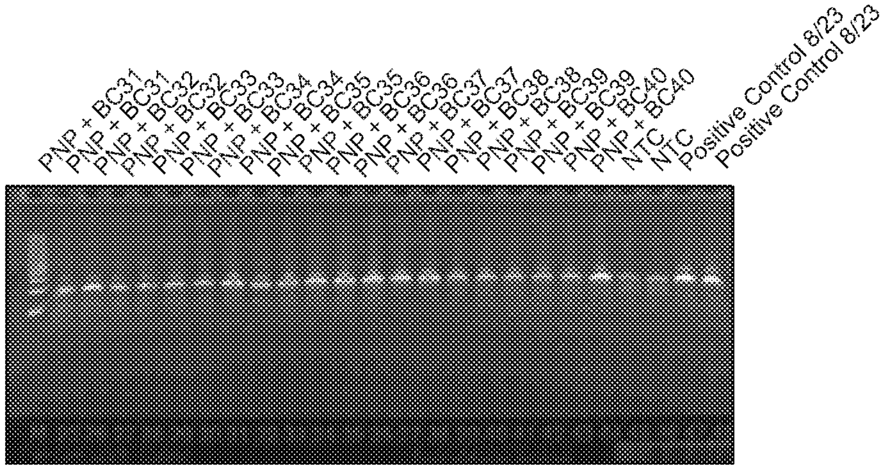
Figure 7:
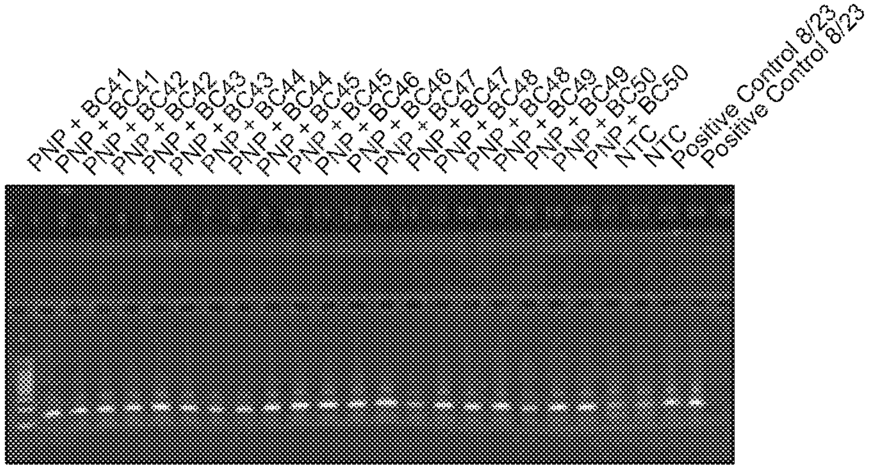
Figure 7:
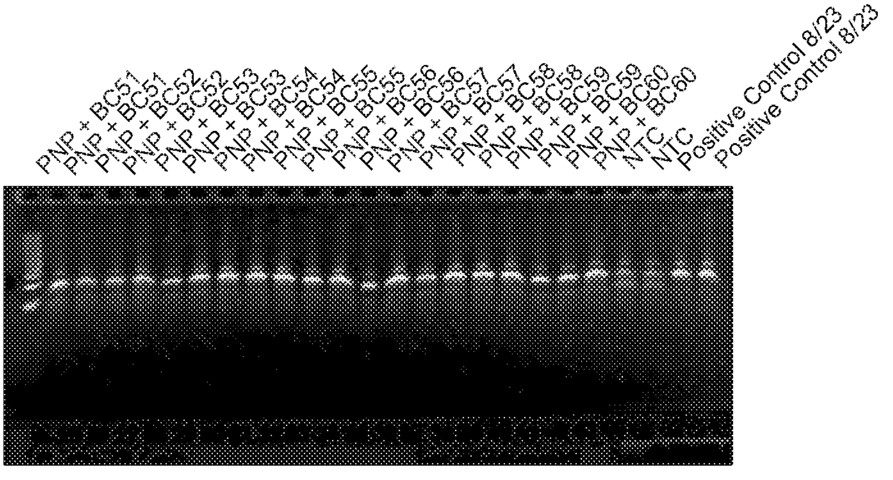
Figure 7:
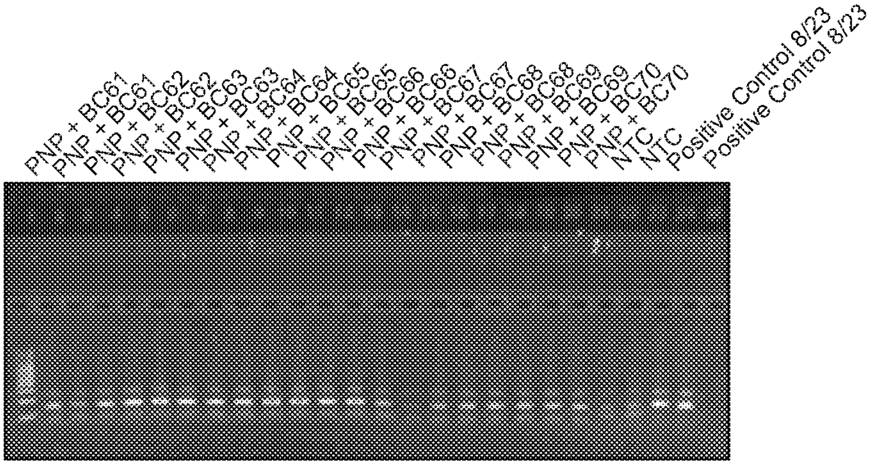
Figure 7:
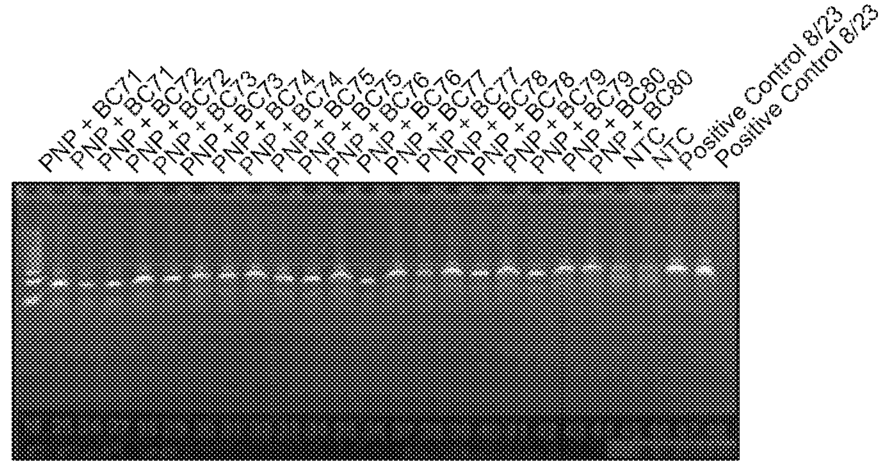
Figure 7:
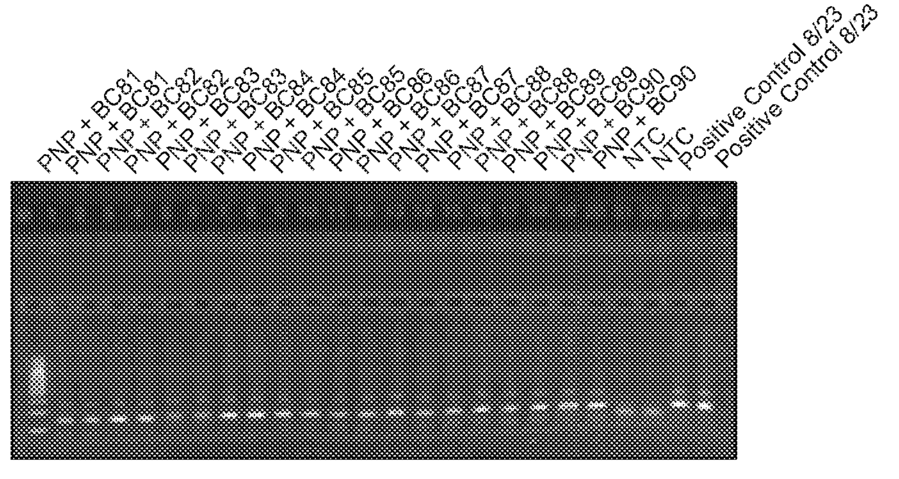
Figure 7:
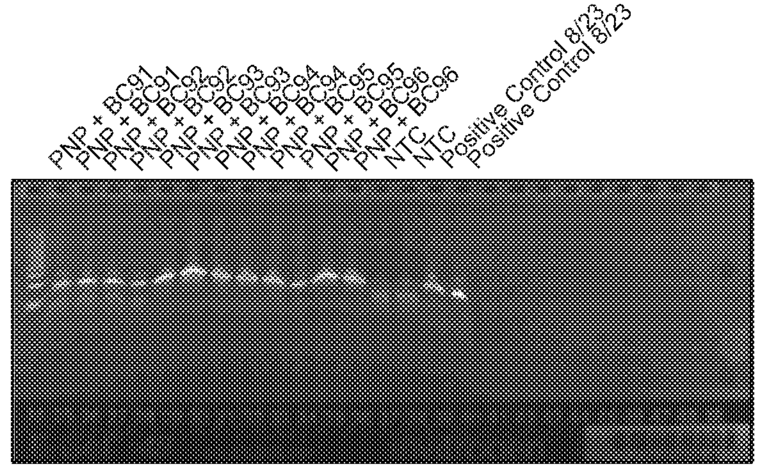

Composition Example 2 (CE2): Nucleic Acid Construct Conjugation to PNPs Via Avidin-Biotin Linkage RAFT copolymers made using CTAs that contain at least one carboxyl terminal group were further functionalized with avidin (FIG. 5*b*). A RAFT copolymer was transferred into a MES buffer at ~12 mg/mL. The sample was sonicated for 30 minutes. EDC reagent and Sulfo-NHS reagent was added to the polymer at a molar ratio of 10:1 and 25:1 respectively, reagent to PNP. The sample was incubated for at least 10 minutes at room temperature to allow the reaction to occur. The reaction volume was filtered through a membrane with a molecular weight cut off of 30 kDa via centrifuge at ~3000×g for ~15 minutes. The filtrate was discarded, and sterile PBS was added to the retentate to reconstitute to 10 mg/mL polymer. Avidin (36.9 mg) was added to the reaction and incubated for 15 minutes at room temperature. The sample was transferred to an amicon ultra-4 centrifuge tube (MWCO 30 kDa). (Max 3.5 mL/Tube) and centrifuged at 4,000×g for 15 minutes. The filtrate was discarded and sterile PBS was added to the retentate to final concentration of 8 mg/mL polymer. A nucleic acid constructs with biotin attached to the 5' end was added to the avidin functionalized polymer at a molar ratio of 10 moles of polymer to 1 mole of nucleic acid constructs. The sample was incubated for at least 15 minutes. The sample was transferred to an amicon ultra-4 centrifuge tube (MWCO 30 kDa, Max 3.5 mL/Tube) and centrifuged at 4,000×g for 15 minutes to remove any unbound nucleic acid constructs. The filtrate (containing unbound nucleic acid constructs) was discarded and sterile PBS was added to the retentate to final concentration of 8 mg/mL polymer. The conjugated nucleic acid constructs were amplified via PCR, using primers designed to bind to the universal primer binding segments on the nucleic acid constructs. The amplicons were detected via gel electrophoresis on agarose gel. The presence of a double band (FIGS. 6 and 7) in a lane indicates the presence of amplicons, showing that nucleic acid constructs were bound to the PNPs.

Figure 13:
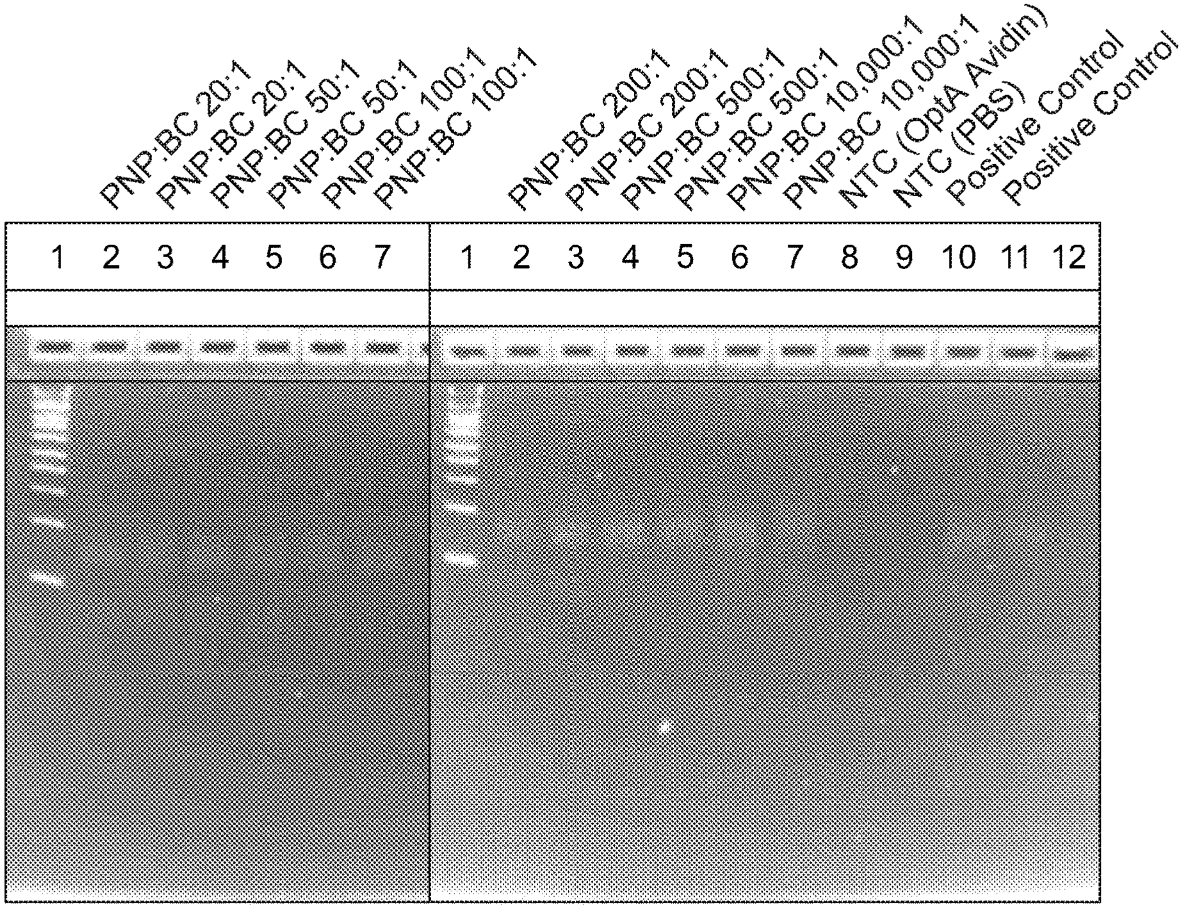
FIG. 13 is an electrophoresis gel showing a band corresponding to barcode (BC) amplicons produced from PCR performed on samples of PNPs with barcodes attached at various molar ratios of PNP to BC (i.e. moles of polymer divided by moles of barcode). The presence of the band for all barcoded PNP samples confirms that the barcode can be detected via PCR on PNPs labeled with barcodes at ratios of anywhere from 20:1 to 10,000:1 (moles PNP:moles BC).

To test the range of PNP to barcode ratios that can be used in the reduction to practice of nucleic acid constructs labeled PNPs, the method above was used to attach the nucleic acid constructs to PNPs using the avidin-biotin linkage (FIG. 5*a*), varying the PNP to nucleic acid constructs ratio from as low as 20:1 to as high as 10,000 to 1 (moles polymer to moles nucleic acid constructs). FIG. 13 shows a gel electrophoresis graph with bands corresponding to the amplicons from nucleic acid constructs produced from a PCR reaction on the nucleic acid constructs with these various PNP to nucleic acid constructs ratios, indicating that these ratios are in the useable range for the reduction to practice of the nucleic acid constructs PNP composition.

The avidin-biotin conjugation method was used to attach 96 unique barcodes to 96 aliquots of the polymer described in Table 2, yielding 96 aliquots of the same polymer in which the population of nanoparticles in each aliquot has a unique barcode attached. These 96 aliquots were pooled by combining the aliquots in volumetrically equivalent amounts into a single vial, yielding a dispersion of 96 distinct populations of barcoded PNPs, in which all populations comprised a polymer micelle formed from the polymer described in Table 2 and a unique barcode from the population of 96 unique barcodes.

Figure 8:
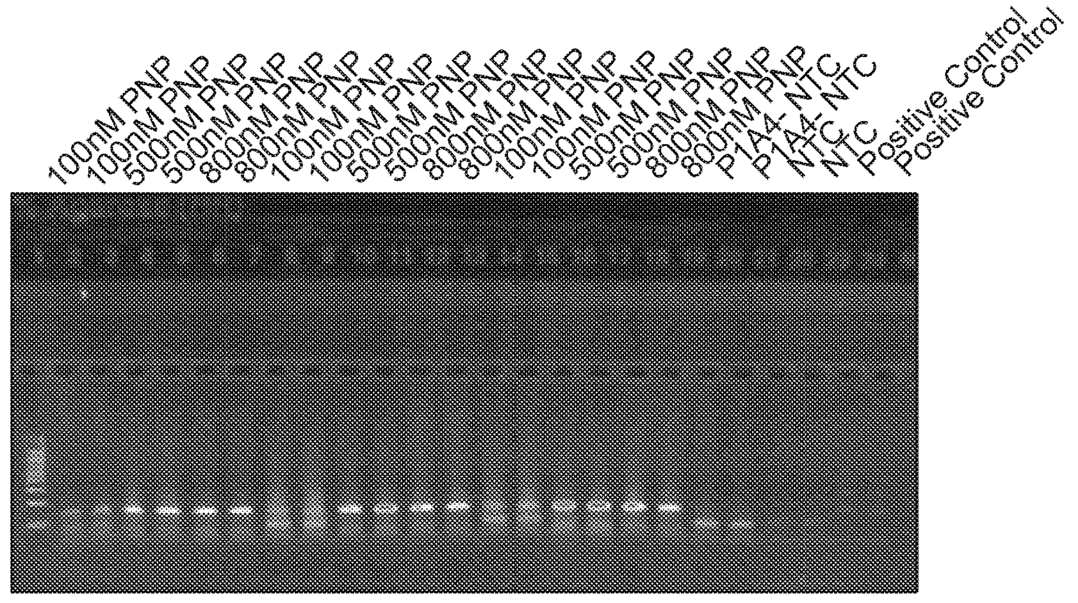
FIG. 8. is an e-gel showing DNA barcode amplification from a pooled sample of 96 unique barcodes, attached to a prototype PNP, extracted after being spiked into a culture of HEK-293 cells. Each frame in the figure is one row of a 48 channel gel electrophoresis. The first column of each gel is a D=NA latter, the bottom band of which is ~100 bases. The bright band in each column near the 100 bp mark indicates amplicons coming from the barcodes.

The pooled sample of avidin-biotin conjugated nucleic acid construct-PNPs were spiked into HEK-293T cells. The cells were seeded in 96 well plates at 20,000 cells per well, in 100 μl at of media and left to adhere overnight. Twenty-four hours after seeding, the pooled sample of PNPs with 96 unique barcodes were added at a dose of ~0.024 mg/mL PNP in each well and placed in an incubator at 37° C. overnight. The next day, barcodes extracted from the samples, using the QIAamp 96 DNA extraction kit and a Qiacube HT instrument according to the manufacturer's protocol. The conjugated barcodes were amplified via PCR, using primers designed to bind to the universal primer binding sequences on the barcodes. The amplicons were detected via gel electrophoresis on agarose gel. The presence of a double band (FIG. 8) in a lane indicates the presence of amplicons, showing that nucleic acid constructs were bound to the PNPs.

Figure 12A:
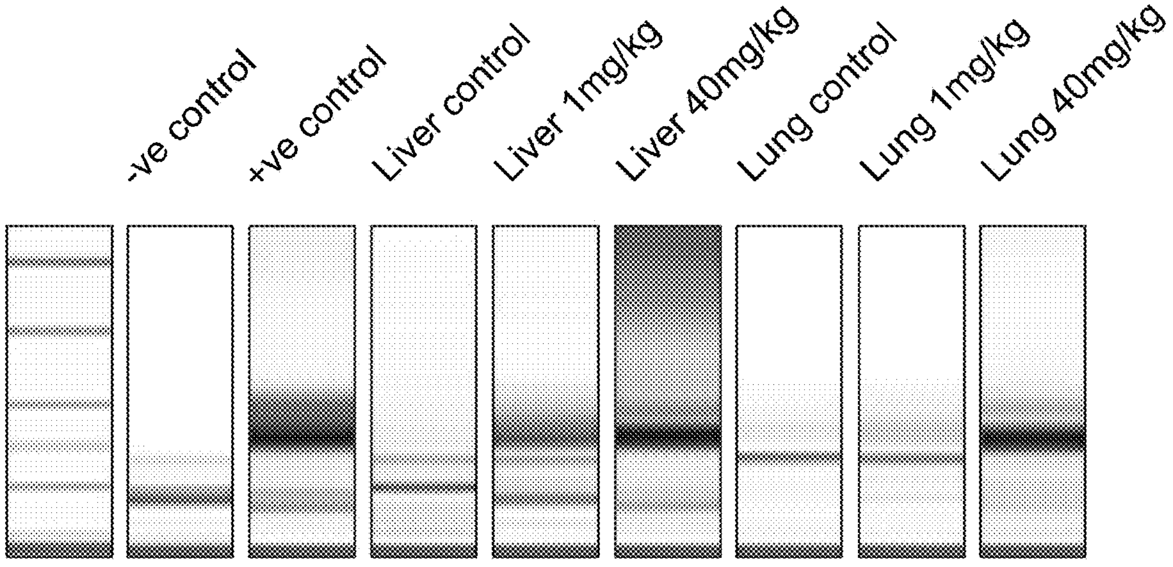
FIGS. 12(*a*)-12(*d*) show gel images of PCR amplified barcodes extracted from indicated mouse tissues (FIGS. 12(*a*) and 12(*b*)); sequencing data demonstrating the ability to detect all 96 individual barcodes from a single mouse organ, where (a) denotes low dose and (b) denotes high dose (FIG. 12(*c*)); and a graph depicting relative abundance of each barcode in a single organ (FIG. 12(*d*)).
Figure 12B:
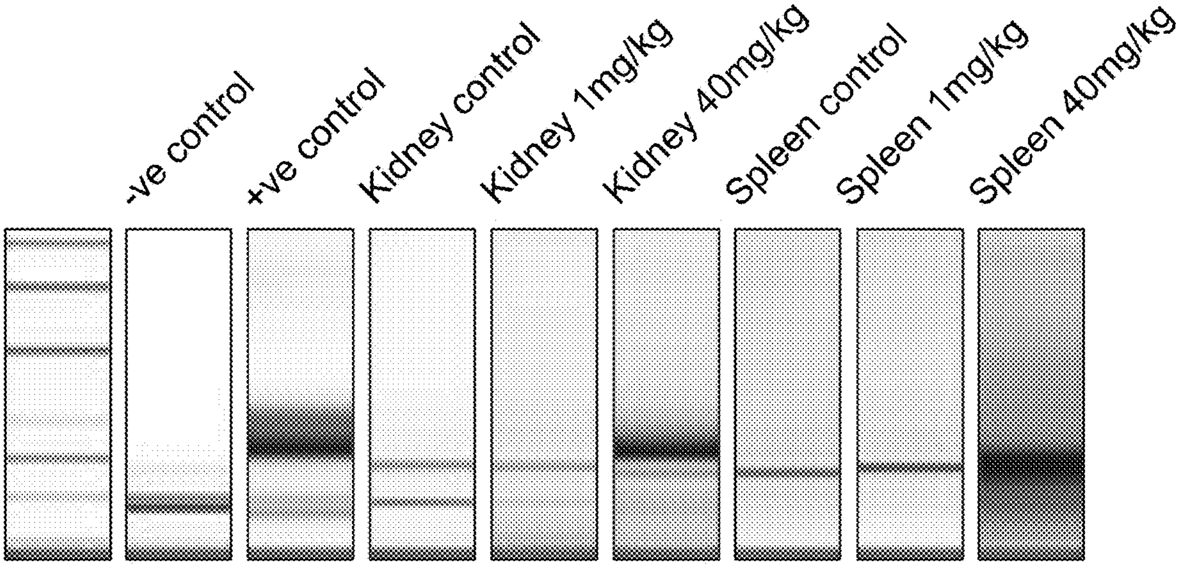
Figure 12C:
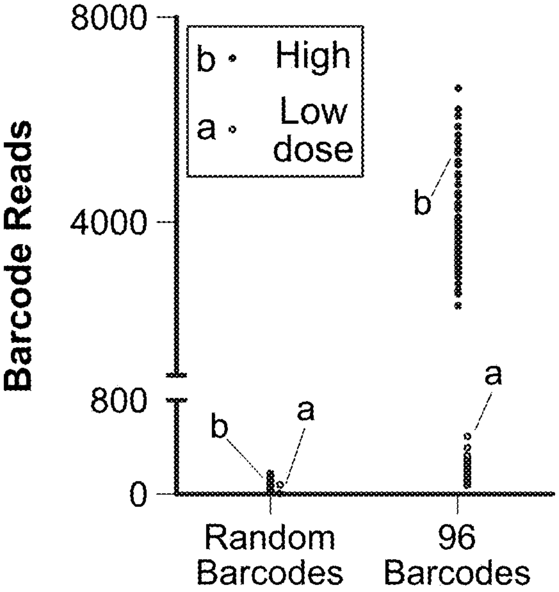
Figure 12D:
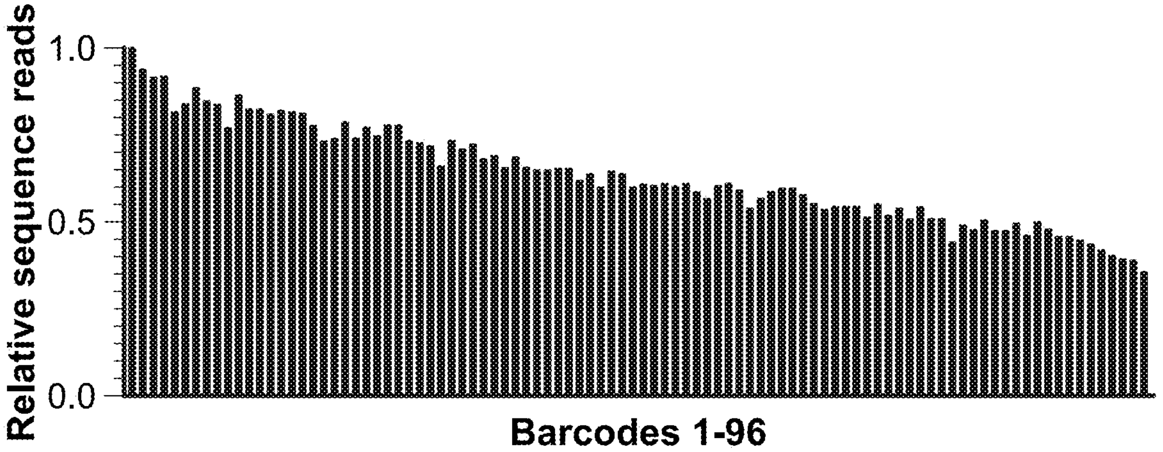

The pooled sample of PNPs with 96 unique barcodes conjugated via avidin-biotin linkage, was administered to mice (using the in vivo screening protocol described below). Twenty-four hours after dosing, the mice were sacrificed and the tissues were analyzed for the presence of the barcoded PNPs. PCR was used to amplify the barcodes from the tissue samples and agilent fragment analysis was used to detect the presence of nucleic acid constructs-PNPs, with a dark band matching the positive control as the indicator of the presence of nucleic acid constructs-PNPs (FIG. 12*a*). This experiment reduced to practice the ability to label PNPs with unique nucleic acid constructs, administer them to mice, and then detect their biodistribution via PCR. We further used deep sequencing techniques to distinguish all 96 unique barcodes in the liver tissue. Library preparations, sequencing and sequence analysis were performed as described below. All 96 unique barcodes were detected in a way that was countable and distinguishable from the others (FIG. 12*c* and FIG. 12*d*). This shows that our compositions allow not only the detection of uniquely barcoded PNPs in mouse tissue 24 hours after dosing, but it also allows us to quantitatively distinguish each uniquely barcoded PNP from all other uniquely barcoded PNPs in the animal tissue.

Example 5

Preparation of RAFT Copolymers for Polymer Nanoparticle Libraries

Briefly, Block 1 reagents (monomer(s), chain transfer agent, initiator, and solvent) were combined in wells of a polypropylene 96-well u-shaped bottom microplate (Greiner Bio-One), in polypropylene 96 well cluster tubes (Corning), in polypropylene Eppendorf microcentrifuge tubes (Sigma-Aldrich), or in polypropylene 50 mL or 15 mL conical tubes (VWR) and placed in a VWR 1400E Sheldon vacuum oven. A 20 mL glass vial was filled with approximately 10-15 mL of solvent (e.g., dimethylformamide), and the vial was placed in the oven to provide a source for atmosphere saturation. The oven was purged with argon at ~3 L/min for approximately 45 minutes and heated to between 60° C. and 75° C. for 6-24 hours. Upon completion of the reaction, acetone was added to the wells or tubes to prevent polymer solidification and the wells or tubes were sealed and left at room temperature overnight. The next day, the reaction product solutions were transferred to 1.5 mL Eppendorf tubes (if necessary) and purified via at least three precipitation washes using an appropriate purification solvent solution (e.g., 80:20 pentane:ether, isopropyl alcohol, methanol, etc.) and centrifugation cycles and dried in vacuo. The Block 1 product was used as the macroRAFT agent for Block 2, and the calculated reagent volumes (as calculated based on theoretical or actual molecular weight information for Block 1) were combined in a polypropylene 96-well u-shaped bottom microplate (Greiner Bio-One), in polypropylene 96 well cluster tubes (Corning), in polypropylene Eppendorf microcentrifuge tubes (Sigma-Aldrich), or in polypropylene 50 mL or 15 mL conical tubes (VWR) for the Block 2 reaction. The reaction mixtures were placed in a VWR 1400E Sheldon vacuum oven, which was argon purged at ~3 L/min for approximately 45 minutes before being heated to between 60° C. and 75° C. for 6-24 hours. The reaction products were purified using the same purification process as used for Block 1 library materials and dried in vacuo. The resulting polymers were resuspended in either acetone or chloroform and aliquoted as needed for experimental use (these transfer solvents evaporated prior to material use), stored in a dry state at room temperature, or dissolved in deionized water, frozen, and lyophilized prior to experimental use. Size was measured using a Wyatt Technology DynaPro Plate Reader III. Molecular weights for Block 1 materials were measured using a DynaPro Plate Reader III. Nanoparticle sizes above the DynaPro Plate Reader III molar mass capability threshold prevented measurement of Block 2 molecular weights for these polymer libraries. All molecular weights for high-throughput polymer libraries are reported as weight average molecular weight ($M_w$).

A summary of the reagents, amounts, and reaction conditions used to synthesize Block 1 and Block 2 of a pilot PNP library of 96 PNPs are shown in Tables 3 and 4, respectively, below. PNPs 22, 61, and 89-96 were used as 10 unique PNPs for HEK cell studies. PNPs 1-88 were used as unique PNPs for flow cytometry studies. Table 3 Abbreviations: ACVA, 4,4'-Azobis(4-cyanovaleric acid); AIBN, Azobisisobutyronitrile; BMA, butyl methacrylate; CTP, 4-Cyano-4-(thiobenzoylthio)pentanoic acid; DMAEMA, dimethylaminoethyl methacrylate; DMF, N,N-Dimethylformamide; ECT, 4-Cyano-4-[(ethylsulfanylthiocarbonyl)sulfanyl]pentanoic acid; MMA, methyl methacrylate. Table 4 Abbreviations: ACVA, 4,4'-Azobis(4-cyanovaleric acid); AIBN, Azobisisobutyronitrile; BMA, butyl methacrylate; CTP, 4-Cyano-4-(thiobenzoylthio)pentanoic acid; DMAEMA, dimethylaminoethyl methacrylate; DMF, N,N-Dimethylformamide; ECT, 4-Cyano-4-[(ethylsulfanylthiocarbonyl)sulfanyl]pentanoic acid; HEMA, 2-Hydroxyethyl methacrylate; MMA, methyl methacrylate. Table 5 Abbreviations: PDI, polydispersity index.

Static Light Scattering (SLS) and Dynamic Light Scattering (DLS) measurements to determine Block 1 molar mass and PNP size (e.g., diameter) were determined using a DynaPro Plate Reader III by Wyatt Technology. Data acquisition and handling were made with DYNAMICS software. SLS and DLS data were obtained under the following conditions:

SOLVENT: Water

TEMPERATURE: 25° C.

SAMPLE VOLUME: 200 μL

DATA ACQUISITION SETTINGS: 5 acquisitions of 5 seconds per acquisition

TABLE 3

Summary of Block 1 Reagents and Reaction Conditions Used in Pilot PNP Library

| PNP | Block 1 Reagents, Purpose, Amounts, and Reaction Conditions | | | | | | | | | | |
|---|---|---|---|---|---|---|---|---|---|---|---|
| | Monomer and Amount (mol) | | Chain Transfer Agent (CTA) and Amount (mol) | | Initiator and Amount (mol) | | Solvent Amount (mol) | | Time (min) | Temp (C.) | Block 1 Rxn % Yield |
| 1 | DMAEMA | 2.49E−04 | CTP | 2.49E−06 | ACVA | 2.49E−06 | DMF | 2.04E−03 | 363 | 75 | 56.4 |
| 2 | DMAEMA | 2.49E−04 | CTP | 1.09E−06 | ACVA | 1.09E−06 | DMF | 2.04E−03 | 363 | 75 | 62.1 |
| 3 | DMAEMA | 2.49E−04 | CTP | 8.54E−07 | ACVA | 8.55E−07 | DMF | 2.04E−03 | 363 | 75 | 59.2 |
| 4 | DMAEMA | 2.49E−04 | CTP | 7.00E−07 | ACVA | 7.01E−07 | DMF | 2.04E−03 | 363 | 75 | 57.9 |
| 5 | DMAEMA | 2.49E−04 | CTP | 5.18E−07 | ACVA | 5.16E−07 | DMF | 2.04E−03 | 363 | 75 | 66.7 |
| 6 | DMAEMA | 2.49E−04 | CTP | 4.61E−07 | ACVA | 4.57E−07 | DMF | 2.04E−03 | 363 | 75 | 66.6 |
| 7 | DMAEMA | 2.49E−04 | CTP | 4.13E−07 | ACVA | 4.08E−07 | DMF | 2.04E−03 | 363 | 75 | 61.5 |
| 8 | DMAEMA | 2.49E−04 | CTP | 3.65E−07 | ACVA | 3.68E−07 | DMF | 2.04E−03 | 363 | 75 | 50.6 |
| 9 | DMAEMA | 2.49E−04 | CTP | 3.36E−07 | ACVA | 3.37E−07 | DMF | 2.04E−03 | 363 | 75 | 57.2 |
| 10 | DMAEMA | 2.49E−04 | CTP | 3.07E−07 | ACVA | 3.12E−07 | DMF | 2.04E−03 | 363 | 75 | 56.7 |
| 11 | DMAEMA | 2.49E−04 | CTP | 1.52E−06 | ACVA | 1.52E−06 | DMF | 2.04E−03 | 363 | 75 | 74.3 |
| 12 | DMAEMA | 2.49E−04 | CTP | 1.09E−06 | ACVA | 1.09E−06 | DMF | 2.04E−03 | 363 | 75 | 73.0 |
| 13 | DMAEMA | 2.49E−04 | CTP | 8.54E−07 | ACVA | 8.55E−07 | DMF | 2.04E−03 | 363 | 75 | 68.1 |
| 14 | DMAEMA | 2.49E−04 | CTP | 7.00E−07 | ACVA | 7.01E−07 | DMF | 2.04E−03 | 363 | 75 | 64.6 |
| 15 | DMAEMA | 2.49E−04 | CTP | 5.18E−07 | ACVA | 5.16E−07 | DMF | 2.04E−03 | 363 | 75 | 69.5 |
| 16 | DMAEMA | 2.49E−04 | CTP | 4.61E−07 | ACVA | 4.57E−07 | DMF | 2.04E−03 | 363 | 75 | 57.0 |
| 17 | DMAEMA | 2.49E−04 | CTP | 4.13E−07 | ACVA | 4.08E−07 | DMF | 2.04E−03 | 363 | 75 | 53.4 |
| 18 | DMAEMA | 2.49E−04 | CTP | 3.65E−07 | ACVA | 3.68E−07 | DMF | 2.04E−03 | 363 | 75 | 66.4 |
| 19 | DMAEMA | 2.49E−04 | CTP | 3.36E−07 | ACVA | 3.37E−07 | DMF | 2.04E−03 | 363 | 75 | 55.0 |
| 20 | DMAEMA | 2.49E−04 | CTP | 2.49E−06 | ACVA | 2.49E−06 | DMF | 2.04E−03 | 363 | 75 | 66.6 |
| 21 | DMAEMA | 2.49E−04 | CTP | 1.52E−06 | ACVA | 1.52E−06 | DMF | 2.04E−03 | 363 | 75 | 75.4 |
| 22 | DMAEMA | 2.49E−04 | CTP | 1.09E−06 | ACVA | 1.09E−06 | DMF | 2.04E−03 | 363 | 75 | 73.6 |
| 23 | DMAEMA | 2.49E−04 | CTP | 8.54E−07 | ACVA | 8.55E−07 | DMF | 2.04E−03 | 363 | 75 | 65.1 |
| 24 | DMAEMA | 2.49E−04 | CTP | 7.00E−07 | ACVA | 7.01E−07 | DMF | 2.04E−03 | 363 | 75 | 71.4 |
| 25 | DMAEMA | 2.49E−04 | CTP | 5.95E−07 | ACVA | 5.94E−07 | DMF | 2.04E−03 | 363 | 75 | 60.7 |
| 26 | DMAEMA | 2.49E−04 | CTP | 5.18E−07 | ACVA | 5.16E−07 | DMF | 2.04E−03 | 363 | 75 | 66.6 |
| 27 | DMAEMA | 2.49E−04 | CTP | 4.61E−07 | ACVA | 4.57E−07 | DMF | 2.04E−03 | 363 | 75 | 55.2 |
| 28 | DMAEMA | 2.49E−04 | CTP | 4.13E−07 | ACVA | 4.08E−07 | DMF | 2.04E−03 | 363 | 75 | 55.7 |
| 29 | DMAEMA | 2.49E−04 | CTP | 3.65E−07 | ACVA | 3.68E−07 | DMF | 2.04E−03 | 363 | 75 | 51.4 |
| 30 | DMAEMA | 2.49E−04 | CTP | 3.36E−07 | ACVA | 3.37E−07 | DMF | 2.04E−03 | 363 | 75 | 53.3 |
| 31 | DMAEMA | 2.49E−04 | CTP | 3.07E−07 | ACVA | 3.12E−07 | DMF | 2.04E−03 | 363 | 75 | 47.2 |
| 32 | DMAEMA | 2.49E−04 | CTP | 1.52E−06 | ACVA | 1.52E−06 | DMF | 2.04E−03 | 363 | 75 | 88.7 |
| 33 | DMAEMA | 2.49E−04 | CTP | 1.09E−06 | ACVA | 1.09E−06 | DMF | 2.04E−03 | 363 | 75 | 72.0 |
| 34 | DMAEMA | 2.49E−04 | CTP | 8.54E−07 | ACVA | 8.55E−07 | DMF | 2.04E−03 | 363 | 75 | 65.0 |
| 35 | DMAEMA | 2.49E−04 | CTP | 5.95E−07 | ACVA | 5.94E−07 | DMF | 2.04E−03 | 363 | 75 | 69.4 |
| 36 | DMAEMA | 2.49E−04 | CTP | 4.61E−07 | ACVA | 4.57E−07 | DMF | 2.04E−03 | 363 | 75 | 46.1 |
| 37 | DMAEMA | 2.49E−04 | CTP | 4.13E−07 | ACVA | 4.08E−07 | DMF | 2.04E−03 | 363 | 75 | 47.5 |
| 38 | DMAEMA | 2.49E−04 | CTP | 3.36E−07 | ACVA | 3.37E−07 | DMF | 2.04E−03 | 363 | 75 | 52.3 |
| 39 | DMAEMA | 2.49E−04 | CTP | 3.07E−07 | ACVA | 3.12E−07 | DMF | 2.04E−03 | 363 | 75 | 55.9 |
| 40 | DMAEMA | 2.49E−04 | CTP | 2.49E−06 | ACVA | 2.49E−06 | DMF | 2.04E−03 | 363 | 75 | 82.3 |
| 41 | DMAEMA | 2.49E−04 | CTP | 8.54E−07 | ACVA | 8.55E−07 | DMF | 2.04E−03 | 363 | 75 | 76.5 |
| 42 | DMAEMA | 2.49E−04 | CTP | 7.00E−07 | ACVA | 7.01E−07 | DMF | 2.04E−03 | 363 | 75 | 71.7 |
| 43 | DMAEMA | 2.49E−04 | CTP | 4.13E−07 | ACVA | 4.08E−07 | DMF | 2.04E−03 | 363 | 75 | 54.9 |
| 44 | DMAEMA | 2.49E−04 | CTP | 3.65E−07 | ACVA | 3.68E−07 | DMF | 2.04E−03 | 363 | 75 | 54.3 |
| 45 | DMAEMA | 2.49E−04 | CTP | 3.36E−07 | ACVA | 3.37E−07 | DMF | 2.04E−03 | 363 | 75 | 54.6 |
| 46 | DMAEMA | 2.49E−04 | CTP | 3.07E−07 | ACVA | 3.12E−07 | DMF | 2.04E−03 | 363 | 75 | 55.0 |
| 47 | DMAEMA | 2.49E−04 | CTP | 1.09E−06 | ACVA | 1.09E−06 | DMF | 2.04E−03 | 363 | 75 | 93.5 |
| 48 | DMAEMA | 2.49E−04 | CTP | 8.54E−07 | ACVA | 8.55E−07 | DMF | 2.04E−03 | 363 | 75 | 79.7 |
| 49 | DMAEMA | 2.49E−04 | CTP | 5.18E−07 | ACVA | 5.16E−07 | DMF | 2.04E−03 | 363 | 75 | 56.9 |
| 50 | DMAEMA | 2.49E−04 | CTP | 4.61E−07 | ACVA | 4.57E−07 | DMF | 2.04E−03 | 363 | 75 | 52.0 |
| 51 | DMAEMA | 2.49E−04 | CTP | 4.13E−07 | ACVA | 4.08E−07 | DMF | 2.04E−03 | 363 | 75 | 55.8 |
| 52 | DMAEMA | 2.49E−04 | CTP | 3.36E−07 | ACVA | 3.37E−07 | DMF | 2.04E−03 | 363 | 75 | 51.8 |
| 53 | DMAEMA | 2.49E−04 | CTP | 3.07E−07 | ACVA | 3.12E−07 | DMF | 2.04E−03 | 363 | 75 | 53.1 |
| 54 | DMAEMA | 2.49E−04 | CTP | 1.52E−06 | ACVA | 1.52E−06 | DMF | 2.04E−03 | 363 | 75 | 86.5 |
| 55 | DMAEMA | 2.49E−04 | CTP | 8.54E−07 | ACVA | 8.55E−07 | DMF | 2.04E−03 | 363 | 75 | 72.9 |
| 56 | DMAEMA | 2.49E−04 | CTP | 7.00E−07 | ACVA | 7.01E−07 | DMF | 2.04E−03 | 363 | 75 | 71.5 |
| 57 | DMAEMA | 2.49E−04 | CTP | 5.95E−07 | ACVA | 5.94E−07 | DMF | 2.04E−03 | 363 | 75 | 59.9 |
| 58 | DMAEMA | 2.49E−04 | CTP | 5.18E−07 | ACVA | 5.16E−07 | DMF | 2.04E−03 | 363 | 75 | 63.7 |
| 59 | DMAEMA | 2.49E−04 | CTP | 4.13E−07 | ACVA | 4.08E−07 | DMF | 2.04E−03 | 363 | 75 | 52.0 |
| 60 | DMAEMA | 2.49E−04 | CTP | 3.65E−07 | ACVA | 3.68E−07 | DMF | 2.04E−03 | 363 | 75 | 54.9 |
| 61 | DMAEMA | 2.49E−04 | CTP | 3.36E−07 | ACVA | 3.37E−07 | DMF | 2.04E−03 | 363 | 75 | 55.3 |
| 62 | DMAEMA | 2.49E−04 | CTP | 3.07E−07 | ACVA | 3.12E−07 | DMF | 2.04E−03 | 363 | 75 | 42.2 |
| 63 | DMAEMA | 2.49E−04 | CTP | 1.52E−06 | ACVA | 1.52E−06 | DMF | 2.04E−03 | 363 | 75 | 82.9 |
| 64 | DMAEMA | 2.49E−04 | CTP | 1.09E−06 | ACVA | 1.09E−06 | DMF | 2.04E−03 | 363 | 75 | 71.2 |
| 65 | DMAEMA | 2.49E−04 | CTP | 5.95E−07 | ACVA | 5.94E−07 | DMF | 2.04E−03 | 363 | 75 | 60.4 |
| 66 | DMAEMA | 2.49E−04 | CTP | 5.18E−07 | ACVA | 5.16E−07 | DMF | 2.04E−03 | 363 | 75 | 64.9 |
| 67 | DMAEMA | 2.49E−04 | CTP | 3.65E−07 | ACVA | 3.68E−07 | DMF | 2.04E−03 | 363 | 75 | 54.0 |
| 68 | DMAEMA | 2.49E−04 | CTP | 3.36E−07 | ACVA | 3.37E−07 | DMF | 2.04E−03 | 363 | 75 | 44.2 |
| 69 | DMAEMA | 2.49E−04 | CTP | 3.07E−07 | ACVA | 3.12E−07 | DMF | 2.04E−03 | 363 | 75 | 52.4 |
| 70 | DMAEMA | 2.49E−04 | CTP | 2.49E−06 | ACVA | 4.97E−07 | DMF | 2.04E−03 | 363 | 75 | 52.5 |

TABLE 3-continued

Summary of Block 1 Reagents and Reaction Conditions Used in Pilot PNP Library

| PNP | Block 1 Reagents, Purpose, Amounts, and Reaction Conditions | | | | | | | | | | |
|---|---|---|---|---|---|---|---|---|---|---|---|
| | Monomer and Amount (mol) | | Chain Transfer Agent (CTA) and Amount (mol) | | Initiator and Amount (mol) | | Solvent Amount (mol) | | Time (min) | Temp (C.) | Block 1 Rxn % Yield |
| 71 | DMAEMA | 2.49E−04 | CTP | 1.52E−06 | ACVA | 3.03E−07 | DMF | 2.04E−03 | 363 | 75 | 46.6 |
| 72 | DMAEMA | 2.49E−04 | CTP | 1.09E−06 | ACVA | 2.19E−07 | DMF | 2.04E−03 | 363 | 75 | 40.2 |
| 73 | DMAEMA | 2.49E−04 | CTP | 8.54E−07 | ACVA | 1.71E−07 | DMF | 2.04E−03 | 363 | 75 | 37.7 |
| 74 | DMAEMA | 2.49E−04 | CTP | 5.18E−07 | ACVA | 1.03E−07 | DMF | 2.04E−03 | 363 | 75 | 27.3 |
| 75 | DMAEMA | 2.49E−04 | CTP | 4.61E−07 | ACVA | 9.05E−08 | DMF | 2.04E−03 | 363 | 75 | 26.7 |
| 76 | DMAEMA | 2.49E−04 | CTP | 4.13E−07 | ACVA | 8.21E−08 | DMF | 2.04E−03 | 363 | 75 | 25.1 |
| 77 | DMAEMA | 2.49E−04 | CTP | 3.65E−07 | ACVA | 7.37E−08 | DMF | 2.04E−03 | 363 | 75 | 23.0 |
| 78 | DMAEMA | 2.49E−04 | CTP | 3.36E−07 | ACVA | 6.74E−08 | DMF | 2.04E−03 | 363 | 75 | 22.8 |
| 79 | DMAEMA | 2.49E−04 | CTP | 2.49E−06 | ACVA | 4.97E−07 | DMF | 2.04E−03 | 363 | 75 | 52.7 |
| 80 | DMAEMA | 2.49E−04 | CTP | 1.52E−06 | ACVA | 3.03E−07 | DMF | 2.04E−03 | 363 | 75 | 47.6 |
| 81 | DMAEMA | 2.49E−04 | CTP | 1.09E−06 | ACVA | 2.19E−07 | DMF | 2.04E−03 | 363 | 75 | 39.3 |
| 82 | DMAEMA | 2.49E−04 | CTP | 8.54E−07 | ACVA | 1.71E−07 | DMF | 2.04E−03 | 363 | 75 | 37.1 |
| 83 | DMAEMA | 2.49E−04 | CTP | 7.00E−07 | ACVA | 1.41E−07 | DMF | 2.04E−03 | 363 | 75 | 34.0 |
| 84 | DMAEMA | 2.49E−04 | CTP | 5.95E−07 | ACVA | 1.18E−07 | DMF | 2.04E−03 | 363 | 75 | 31.8 |
| 85 | DMAEMA | 2.49E−04 | CTP | 5.18E−07 | ACVA | 1.03E−07 | DMF | 2.04E−03 | 363 | 75 | 25.1 |
| 86 | DMAEMA | 2.49E−04 | CTP | 4.61E−07 | ACVA | 9.05E−08 | DMF | 2.04E−03 | 363 | 75 | 25.7 |
| 87 | DMAEMA | 2.49E−04 | CTP | 4.13E−07 | ACVA | 8.21E−08 | DMF | 2.04E−03 | 363 | 75 | 23.9 |
| 88 | DMAEMA | 2.49E−04 | CTP | 7.00E−07 | ACVA | 1.41E−07 | DMF | 2.04E−03 | 363 | 75 | 27.7 |
| 89 | DMAEMA | 2.49E−04 | CTP | 8.54E−07 | ACVA | 1.71E−07 | DMF | 2.04E−03 | 363 | 75 | 32.8 |
| 90 | DMAEMA | 2.49E−04 | CTP | 3.65E−07 | ACVA | 7.37E−08 | DMF | 2.04E−03 | 363 | 75 | 21.0 |
| 91 | DMAEMA | 2.53E−04 | CTP | 8.42E−07 | ACVA | 8.44E−07 | DMF | 2.03E−03 | 360 | 70 | 103.4 |
| 92 | MMA | 3.95E−04 | CTP | 1.32E−06 | AIBN | 2.63E−07 | DMF | 2.04E−03 | 360 | 70 | 61.2 |
| 93 | BMA | 2.80E−04 | ECT | 9.32E−07 | AIBN | 1.86E−07 | DMF | 2.01E−03 | 360 | 70 | 32.4 |
| 94 | DMAEMA | 2.53E−04 | ECT | 8.43E−07 | AIBN | 8.44E−07 | DMF | 2.03E−03 | 360 | 65 | 101.0 |
| 95 | MMA | 3.96E−04 | ECT | 1.32E−06 | ACVA | 1.32E−07 | DMF | 2.04E−03 | 360 | 65 | 13.7 |
| 96 | BMA | 2.80E−04 | CTP | 9.31E−07 | AIBN | 9.32E−07 | DMF | 2.01E−03 | 360 | 65 | 32.1 |

TABLE 4

Summary of Block 2 Reagents and Reaction Conditions Used in Pilot PNP Library

| PNP | Block 2 Reagents, Purpose, Amounts, and Reaction Conditions | | | | | | | | | | |
|---|---|---|---|---|---|---|---|---|---|---|---|
| | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
| 1 | HEMA | 2.54E−05 | p(DMA EMA), (006-A1 Block 1) | 1.27E−06 | ACVA | 1.27E−06 | DMF | 8.00E−04 | 1440 | 64 | 65.3 |
| 2 | HEMA | 2.70E−05 | p(DMA EMA), (006-A3 Block 1) | 1.33E−06 | ACVA | 1.33E−06 | DMF | 8.33E−04 | 1440 | 64 | 85.7 |
| 3 | HEMA | 2.38E−05 | p(DMA EMA), (006-A4 Block 1) | 1.19E−06 | ACVA | 1.19E−06 | DMF | 7.25E−04 | 1440 | 64 | 77.4 |
| 4 | HEMA | 1.91E−05 | p(DMA EMA), (006-A5 Block 1) | 9.60E−06 | ACVA | 9.60E−07 | DMF | 5.36E−04 | 1440 | 64 | 56.6 |
| 5 | HEMA | 2.15E−05 | p(DMA EMA), (006-A7 Block 1) | 1.08E−06 | ACVA | 1.08E−06 | DMF | 5.92E−04 | 1440 | 64 | 83.8 |
| 6 | HEMA | 2.07E−05 | p(DMA EMA), (006-A8 Block 1) | 1.03E−06 | ACVA | 1.03E−06 | DMF | 5.54E−04 | 1440 | 64 | 87.4 |
| 7 | HEMA | 1.99E−05 | p(DMA EMA), (006-A9 Block 1) | 9.78E−06 | ACVA | 9.78E−07 | DMF | 5.32E−04 | 1440 | 64 | 85.5 |

TABLE 4-continued

Summary of Block 2 Reagents and Reaction Conditions Used in Pilot PNP Library

| PNP | Block 2 Reagents, Purpose, Amounts, and Reaction Conditions | | | | | | | | | | |
|---|---|---|---|---|---|---|---|---|---|---|---|
| | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
| 8 | HEMA | 1.51E−05 | p(DMA EMA), (006-A10 Block 1) | 7.57E−07 | ACVA | 7.56E−07 | DMF | 3.99E−04 | 1440 | 64 | 95.6 |
| 9 | HEMA | 1.75E−05 | p(DMA EMA), (006-A11 Block 1) | 8.71E−07 | ACVA | 8.71E−07 | DMF | 4.56E−04 | 1440 | 64 | 87.4 |
| 10 | HEMA | 1.51E−05 | p(DMA EMA), (006-A12 Block 1) | 7.48E−07 | ACVA | 7.49E−07 | DMF | 3.62E−04 | 1440 | 64 | 90.2 |
| 11 | HEMA | 7.07E−05 | p(DMA EMA), (006-B2 Block 1) | 1.55E−06 | ACVA | 1.56E−06 | DMF | 2.67E−03 | 1440 | 64 | 73.3 |
| 12 | HEMA | 4.53E−05 | p(DMA EMA), (006-B3 Block 1) | 9.94E−07 | ACVA | 9.95E−07 | DMF | 1.58E−03 | 1440 | 64 | 71.6 |
| 13 | HEMA | 5.96E−05 | p(DMA EMA), (006-B4 Block 1) | 1.31E−06 | ACVA | 1.31E−06 | DMF | 2.22E−03 | 1440 | 64 | 70.3 |
| 14 | HEMA | 5.16E−05 | p(DMA EMA), (006-B5 Block 1) | 1.12E−06 | ACVA | 1.12E−06 | DMF | 1.87E−03 | 1440 | 64 | 87.8 |
| 15 | HEMA | 5.24E−05 | p(DMA EMA), (006-B7 Block 1) | 1.15E−06 | ACVA | 1.15E−06 | DMF | 1.90E−03 | 1440 | 64 | 85.3 |
| 16 | HEMA | 3.02E−05 | p(DMA EMA), (006-B8 Block 1) | 6.62E−07 | ACVA | 6.60E−07 | DMF | 1.01E−03 | 1440 | 64 | 86.3 |
| 17 | HEMA | 2.94E−05 | p(DMA EMA), (006-B9 Block 1) | 6.35E−07 | ACVA | 6.35E−07 | DMF | 9.77E−04 | 1440 | 64 | 90.9 |
| 18 | HEMA | 3.18E−05 | p(DMA EMA), (006-B10 Block 1) | 6.93E−07 | ACVA | 6.92E−07 | DMF | 1.02E−03 | 1440 | 64 | 84.3 |
| 19 | HEMA | 2.94E−05 | p(DMA EMA), (006-B11 Block 1) | 6.50E−07 | ACVA | 6.49E−07 | DMF | 9.96E−04 | 1440 | 64 | 86.3 |
| 20 | HEMA | 1.45E−04 | p(DMA EMA), (006-C1 Block 1) | 2.03E−06 | ACVA | 2.03E−06 | DMF | 5.86E−03 | 1440 | 64 | 74.8 |
| 21 | HEMA | 1.12E−04 | p(DMA EMA), (006-C2 Block 1) | 1.57E−06 | ACVA | 1.57E−06 | DMF | 4.41E−03 | 1440 | 64 | 79.8 |
| 22 | HEMA | 1.02E−04 | p(DMA EMA), (006-C3 Block 1) | 1.44E−06 | ACVA | 1.44E−06 | DMF | 4.03E−03 | 1440 | 64 | 82.6 |
| 23 | HEMA | 9.06E−05 | p(DMA EMA), (006-C4 Block 1) | 1.27E−06 | ACVA | 1.27E−06 | DMF | 3.55E−03 | 1440 | 64 | 82.9 |
| 24 | HEMA | 6.83E−05 | p(DMA EMA), (006-C5 Block 1) | 9.54E−07 | ACVA | 9.53E−07 | DMF | 2.56E−03 | 1440 | 64 | 86.9 |

TABLE 4-continued

Summary of Block 2 Reagents and Reaction Conditions Used in Pilot PNP Library

| PNP | Block 2 Reagents, Purpose, Amounts, and Reaction Conditions | | | | | | | | | | |
|---|---|---|---|---|---|---|---|---|---|---|---|
| | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
| 25 | HEMA | 6.52E−05 | p(DMA EMA), (006-C6 Block 1) | 9.16E−07 | ACVA | 9.17E−07 | DMF | 2.50E−03 | 1440 | 64 | 94.4 |
| 26 | HEMA | 6.91E−05 | p(DMA EMA), (006-C7 Block 1) | 9.62E−07 | ACVA | 9.63E−07 | DMF | 2.61E−03 | 1440 | 64 | 89.5 |
| 27 | HEMA | 6.36E−05 | p(DMA EMA), (006-C8 Block 1) | 8.91E−07 | ACVA | 8.92E−07 | DMF | 2.44E−03 | 1440 | 64 | 97.0 |
| 28 | HEMA | 5.01E−05 | p(DMA EMA), (006-C9 Block 1) | 6.99E−07 | ACVA | 6.99E−07 | DMF | 1.86E−03 | 1440 | 64 | 90.0 |
| 29 | HEMA | 4.93E−05 | p(DMA EMA), (006-C10 Block 1) | 6.95E−07 | ACVA | 6.96E−07 | DMF | 1.86E−03 | 1440 | 64 | 90.1 |
| 30 | HEMA | 5.40E−05 | p(DMA EMA), (006-C11 Block 1) | 7.51E−07 | ACVA | 7.53E−07 | DMF | 2.02E−03 | 1440 | 64 | 90.4 |
| 31 | HEMA | 1.99E−05 | p(DMA EMA), (006-C12 Block 1) | 2.83E−07 | ACVA | 2.82E−07 | DMF | 6.23E−04 | 1440 | 64 | 82.4 |
| 32 | HEMA | 1.87E−04 | p(DMA EMA), (006-D2 Block 1) | 1.92E−06 | ACVA | 1.92E−06 | DMF | 7.52E−03 | 1440 | 64 | 73.9 |
| 33 | HEMA | 9.69E−05 | p(DMA EMA), (006-D3 Block 1) | 9.94E−07 | ACVA | 9.95E−07 | DMF | 3.77E−03 | 1440 | 64 | 83.0 |
| 34 | HEMA | 1.12E−04 | p(DMA EMA), (006-D4 Block 1) | 1.15E−06 | ACVA | 1.15E−06 | DMF | 4.45E−03 | 1440 | 64 | 81.5 |
| 35 | HEMA | 1.09E−04 | p(DMA EMA), (006-D6 Block 1) | 1.12E−06 | ACVA | 1.12E−06 | DMF | 4.31E−03 | 1440 | 64 | 85.9 |
| 36 | HEMA | 6.28E−05 | p(DMA EMA), (006-D8 Block 1) | 6.48E−07 | ACVA | 6.46E−07 | DMF | 2.45E−03 | 1440 | 64 | 94.7 |
| 37 | HEMA | 5.56E−05 | p(DMA EMA), (006-D9 Block 1) | 5.74E−07 | ACVA | 5.74E−07 | DMF | 2.15E−03 | 1440 | 64 | 96.7 |
| 38 | HEMA | 3.42E−05 | p(DMA EMA), (006-D11 Block 1) | 3.54E−07 | ACVA | 3.53E−07 | DMF | 1.21E−03 | 1440 | 64 | 90.7 |
| 39 | HEMA | 3.73E−05 | p(DMA EMA), (006-D12 Block 1) | 3.88E−07 | ACVA | 3.89E−07 | DMF | 1.33E−03 | 1440 | 64 | 76.5 |
| 40 | HEMA | 1.80E−04 | p(DMA EMA), (006-E1 Block 1) | 1.46E−06 | ACVA | 1.47E−06 | DMF | 7.27E−03 | 1440 | 64 | 81.5 |
| 41 | HEMA | 1.08E−04 | p(DMA EMA), (006-E4 Block 1) | 8.80E−07 | ACVA | 8.81E−07 | DMF | 4.23E−03 | 1440 | 64 | 80.6 |

TABLE 4-continued

Summary of Block 2 Reagents and Reaction Conditions Used in Pilot PNP Library

| PNP | Block 2 Reagents, Purpose, Amounts, and Reaction Conditions | | | | | | | | | | |
|---|---|---|---|---|---|---|---|---|---|---|---|
| | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
| 42 | HEMA | 1.32E−04 | p(DMA EMA), (006-E5 Block 1) | 1.07E−06 | ACVA | 1.07E−06 | DMF | 5.28E−03 | 1440 | 64 | 81.7 |
| 43 | HEMA | 6.04E−05 | p(DMA EMA), (006-E9 Block 1) | 4.94E−07 | ACVA | 4.92E−07 | DMF | 2.32E−03 | 1440 | 64 | 92.0 |
| 44 | HEMA | 4.29E−05 | p(DMA EMA), (006-E10 Block 1) | 3.52E−07 | ACVA | 3.53E−07 | DMF | 1.58E−03 | 1440 | 64 | 82.2 |
| 45 | HEMA | 6.52E−05 | p(DMA EMA), (006-E11 Block 1) | 5.32E−07 | ACVA | 5.32E−07 | DMF | 2.52E−03 | 1440 | 64 | 81.3 |
| 46 | HEMA | 5.72E−05 | p(DMA EMA), (006-E12 Block 1) | 4.66E−07 | ACVA | 4.67E−07 | DMF | 2.17E−03 | 1440 | 64 | 70.6 |
| 47 | HEMA | 3.47E−05 | p(DMA EMA), (006-F3 Block 1) | 2.34E−06 | ACVA | 2.34E−06 | DMF | 1.44E−02 | 1440 | 64 | 76.5 |
| 48 | HEMA | 1.83E−04 | p(DMA EMA), (006-F4 Block 1) | 1.23E−06 | ACVA | 1.23E−06 | DMF | 7.42E−03 | 1440 | 64 | 77.4 |
| 49 | HEMA | 1.29E−04 | p(DMA EMA), (006-F7 Block 1) | 8.68E−07 | ACVA | 8.67E−07 | DMF | 5.22E−03 | 1440 | 64 | 80.4 |
| 50 | HEMA | 1.20E−04 | p(DMA EMA), (006-F8 Block 1) | 8.09E−07 | ACVA | 8.10E−07 | DMF | 4.87E−03 | 1440 | 64 | 81.1 |
| 51 | HEMA | 1.06E−04 | p(DMA EMA), (006-F9 Block 1) | 7.13E−07 | ACVA | 7.14E−07 | DMF | 4.24E−03 | 1440 | 64 | 75.3 |
| 52 | HEMA | 2.62E−05 | p(DMA EMA), (006-F11 Block 1) | 1.79E−07 | ACVA | 1.78E−07 | DMF | 8.80E−04 | 1440 | 64 | 83.2 |
| 53 | HEMA | 9.45E−05 | p(DMA EMA), (006-F12 Block 1) | 6.36E−07 | ACVA | 6.35E−07 | DMF | 3.77E−03 | 1440 | 64 | 77.4 |
| 54 | HEMA | 3.09E−04 | p(DMA EMA), (006-G2 Block 1) | 1.77E−06 | ACVA | 1.77E−06 | DMF | 1.28E−02 | 1440 | 64 | 78.8 |
| 55 | HEMA | 2.27E−04 | p(DMA EMA), (006-G4 Block 1) | 1.30E−06 | ACVA | 1.30E−06 | DMF | 9.33E−03 | 1440 | 64 | 77.3 |
| 56 | HEMA | 2.40E−04 | p(DMA EMA), (006-G5 Block 1) | 1.38E−06 | ACVA | 1.38E−06 | DMF | 9.90E−03 | 1440 | 64 | 75.0 |
| 57 | HEMA | 1.54E−04 | p(DMA EMA), (006-G6 Block 1) | 8.86E−07 | ACVA | 8.85E−07 | DMF | 6.30E−03 | 1440 | 64 | 82.7 |
| 58 | HEMA | 1.17E−04 | p(DMA EMA), (006-G7 Block 1) | 6.72E−07 | ACVA | 6.71E−07 | DMF | 4.68E−03 | 1440 | 64 | 83.9 |

TABLE 4-continued

Summary of Block 2 Reagents and Reaction Conditions Used in Pilot PNP Library

| | Block 2 Reagents, Purpose, Amounts, and Reaction Conditions | | | | | | | | | | |
|---|---|---|---|---|---|---|---|---|---|---|---|
| PNP | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
| 59 | HEMA | 9.14E−05 | p(DMA EMA), (006-G9 Block 1) | 5.26E−07 | ACVA | 5.24E−07 | DMF | 3.66E−03 | 1440 | 64 | 74.6 |
| 60 | HEMA | 9.93E−05 | p(DMA EMA), (006-G10 Block 1) | 5.70E−07 | ACVA | 5.71E−07 | DMF | 3.97E−03 | 1440 | 64 | N/A |
| 61 | HEMA | 8.66E−05 | p(DMA EMA), (006-G11 Block 1) | 4.97E−07 | ACVA | 4.96E−07 | DMF | 3.43E−03 | 1440 | 64 | 72.8 |
| 62 | HEMA | 6.36E−05 | p(DMA EMA), (006-G12 Block 1) | 3.65E−07 | ACVA | 3.64E−07 | DMF | 2.51E−03 | 1440 | 64 | 65.1 |
| 63 | HEMA | 3.78E−04 | p(DMA EMA), (006-H2 Block 1) | 1.89E−06 | ACVA | 1.89E−06 | DMF | 1.57E−02 | 1440 | 64 | 70.6 |
| 64 | HEMA | 3.50E−04 | p(DMA EMA), (006-H3 Block 1) | 1.75E−06 | ACVA | 1.75E−06 | DMF | 1.46E−02 | 1440 | 64 | 74.1 |
| 65 | HEMA | 1.87E−04 | p(DMA EMA), (006-H6 Block 1) | 9.35E−07 | ACVA | 9.35E−07 | DMF | 7.69E−03 | 1440 | 64 | 70.8 |
| 66 | HEMA | 1.78E−04 | p(DMA EMA), (006-H7 Block 1) | 8.90E−07 | ACVA | 8.92E−07 | DMF | 7.28E−03 | 1440 | 64 | 81.8 |
| 67 | HEMA | 1.16E−04 | p(DMA EMA), (006-H10 Block 1) | 5.78E−07 | ACVA | 5.78E−07 | DMF | 4.67E−03 | 1440 | 64 | 81.9 |
| 68 | HEMA | 7.23E−05 | p(DMA EMA), (006-H11 Block 1) | 3.60E−07 | ACVA | 3.60E−07 | DMF | 2.86E−03 | 1440 | 64 | 83.0 |
| 69 | HEMA | 8.50E−05 | p(DMA EMA), (006-H12 Block 1) | 4.23E−07 | ACVA | 4.25E−07 | DMF | 3.35E−03 | 1440 | 64 | 70.6 |
| 70 | HEMA | 3.75E−05 | p(DMA EMA), (007-A1 Block 1) | 1.88E−06 | ACVA | 3.75E−07 | DMF | 1.92E−03 | 1440 | 64 | 55.7 |
| 71 | HEMA | 1.72E−05 | p(DMA EMA), (007-A2 Block 1) | 8.63E−07 | ACVA | 1.72E−07 | DMF | 7.77E−04 | 1440 | 64 | 71.1 |
| 72 | HEMA | 1.99E−05 | p(DMA EMA), (007-A3 Block 1) | 9.99E−07 | ACVA | 2.00E−07 | DMF | 9.65E−04 | 1440 | 64 | 76.6 |
| 73 | HEMA | 1.30E−05 | p(DMA EMA), (007-A4 Block 1) | 6.51E−07 | ACVA | 1.30E−07 | DMF | 5.74E−04 | 1440 | 64 | 80.3 |
| 74 | HEMA | 6.12E−06 | p(DMA EMA), (007-A7 Block 1) | 3.07E−07 | ACVA | 6.14E−08 | DMF | 2.28E−04 | 1440 | 64 | 73.5 |
| 75 | HEMA | 3.34E−06 | p(DMA EMA), (007-A8 Block 1) | 1.68E−07 | ACVA | 3.35E−08 | DMF | 7.03E−05 | 1440 | 64 | 72.3 |
| 76 | HEMA | 5.40E−06 | p(DMA EMA), | 2.71E−07 | ACVA | 5.42E−08 | DMF | 1.97E−04 | 1440 | 64 | 66.6 |

TABLE 4-continued

| Summary of Block 2 Reagents and Reaction Conditions Used in Pilot PNP Library | | | | | | | | | | | |
|---|---|---|---|---|---|---|---|---|---|---|---|
| | Block 2 Reagents, Purpose, Amounts, and Reaction Conditions | | | | | | | | | | |
| PNP | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
| 77 | HEMA | 5.06E−06 | (007-A9 Block 1) p(DMAEMA), | 2.52E−07 | ACVA | 5.03E−08 | DMF | 1.86E−04 | 1440 | 64 | 73.6 |
| 78 | HEMA | 5.24E−06 | (007-A10 Block 1) p(DMAEMA), | 2.61E−07 | ACVA | 5.21E−08 | DMF | 1.96E−04 | 1440 | 64 | 77.6 |
| 79 | HEMA | 7.27E−05 | (007-A11 Block 1) p(DMAEMA), | 1.59E−06 | ACVA | 3.18E−07 | DMF | 3.94E−03 | 1440 | 64 | 45.1 |
| 80 | HEMA | 3.45E−05 | (006-B1 Block 1) p(DMAEMA), | 7.54E−07 | ACVA | 1.51E−07 | DMF | 1.76E−03 | 1440 | 64 | 67.5 |
| 81 | HEMA | 2.10E−05 | (007-B2 Block 1) p(DMAEMA), | 4.58E−07 | ACVA | 9.17E−08 | DMF | 1.02E−03 | 1440 | 64 | 66.6 |
| 82 | HEMA | 3.26E−05 | (007-B3 Block 1) p(DMAEMA), | 7.13E−07 | ACVA | 1.43E−07 | DMF | 1.71E−03 | 1440 | 64 | 52.8 |
| 83 | HEMA | 1.84E−05 | (007-B4 Block 1) p(DMAEMA), | 4.02E−07 | ACVA | 8.06E−08 | DMF | 9.00E−04 | 1440 | 64 | 76.9 |
| 84 | HEMA | 2.63E−05 | (007-B5 Block 1) p(DMAEMA), | 5.76E−07 | ACVA | 1.15E−07 | DMF | 1.37E−03 | 1440 | 64 | 60.8 |
| 85 | HEMA | 1.81E−05 | (007-B6 Block 1) p(DMAEMA), | 3.96E−07 | ACVA | 7.92E−08 | DMF | 9.29E−04 | 1440 | 64 | 70.2 |
| 86 | HEMA | 2.14E−05 | (007-B7 Block 1) p(DMAEMA), | 4.67E−07 | ACVA | 9.35E−08 | DMF | 1.11E−03 | 1440 | 64 | 69.4 |
| 87 | HEMA | 1.64E−05 | (007-B8 Block 1) p(DMAEMA), | 3.58E−07 | ACVA | 7.17E−08 | DMF | 8.34E−04 | 1440 | 64 | 79.0 |
| 88 | HEMA | 8.48E−05 | (007-B9 Block 1) p(DMAEMA), | 6.90E−07 | ACVA | 1.38E−07 | DMF | 4.76E−03 | 1440 | 64 | 62.9 |
| 89 | HEMA | 1.45E−04 | (007-E5 Block 1) p(DMAEMA), | 9.74E−07 | ACVA | 1.95E−07 | DMF | 8.18E−03 | 1440 | 64 | 49.4 |
| 90 | HEMA | 5.07E−05 | (007-F4 Block 1) p(DMAEMA), | 4.12E−07 | ACVA | 8.24E−08 | DMF | 2.82E−03 | 1440 | 64 | 46.5 |
| 91 | MMA | 3.17E−04 | (007-E10 Block 1) p(DMAEMA), | 1.06E−06 | ACVA | 1.06E−06 | DMF | 9.27E−04 | 1440 | 60 | 30.5 |
| 92 | DMAEMA | 8.08E−04 | (009-A10 Block 1) p(MMA), | 2.69E−06 | AIBN | 5.39E−07 | DMF | 1.72E−03 | 1440 | 60 | 61.9 |
| 93 | DMAEMA | 9.92E−04 | (009-E8 Block 1) p(BMA), | 3.31E−06 | AIBN | 6.61E−07 | DMF | 2.11E−03 | 1440 | 60 | 74.4 |
| 94 | BMA | 7.75E−04 | (009-G2 Block 1) p(DMAEMA), | 2.58E−06 | AIBN | 2.58E−06 | DMF | 1.74E−03 | 1440 | 60 | 17.3 |

TABLE 4-continued

| Summary of Block 2 Reagents and Reaction Conditions Used in Pilot PNP Library | | | | | | | | | | | |
|---|---|---|---|---|---|---|---|---|---|---|---|
| | Block 2 Reagents, Purpose, Amounts, and Reaction Conditions | | | | | | | | | | |
| PNP | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
| 95 | DMAEMA | 1.25E−04 | (011-B1 Block 1) p(MMA), (011-E6 | 4.16E−07 | ACVA | 4.17E−08 | DMF | 2.66E−04 | 1440 | 60 | 21.2 |
| 96 | DMAEMA | 2.71E−04 | Block 1) p(BMA), (011-G7 Block 1) | 9.04E−07 | AIBN | 9.04E−07 | DMF | 5.78E−04 | 1440 | 60 | 53.6 |

TABLE 5

| Summary of Pilot PNP Library Characterization Data | | | |
|---|---|---|---|
| PNP | Block 1 DynaPro Result (molar mass, kDa) | DynaPro DLS Z-Avg Result (size, nm) | Size PDI (goal < 0.3) |
| 1 | 16.3 | 386.9 | Multimodal |
| 2 | 16.8 | 574.3 | Multimodal |
| 3 | 17.9 | 331.8 | 0.121 |
| 4 | 21.6 | 345.1 | 0.152 |
| 5 | 22.3 | 355.8 | 0.483 |
| 6 | 23.3 | 379.7 | 0.268 |
| 7 | 22.7 | 365.7 | 0.219 |
| 8 | 23.9 | 317.8 | 0.040 |
| 9 | 24.1 | 296.2 | 0.137 |
| 10 | 27.2 | 323.9 | 0.254 |
| 11 | 17.4 | 1017.8 | 0.166 |
| 12 | 26.9 | 1368.9 | Multimodal |
| 13 | 18.7 | 450.2 | 0.087 |
| 14 | 20.9 | 389.2 | 0.152 |
| 15 | 21.9 | 291.5 | 0.111 |
| 16 | 31.2 | 361 | 0.243 |
| 17 | 30.3 | 317.7 | 0.201 |
| 18 | 35.0 | 345.3 | 0.114 |
| 19 | 30.7 | 267.1 | 0.137 |
| 20 | 12.1 | 1383 | 0.238 |
| 21 | 17.7 | 459 | 0.301 |
| 22 | 18.8 | 436.7 | 0.314 |
| 23 | 18.6 | 448 | 0.492 |
| 24 | 26.7 | 422.8 | 0.368 |
| 25 | 24.1 | 333 | 0.214 |
| 26 | 25.1 | 275.6 | Multimodal |
| 27 | 22.8 | 318.3 | 0.219 |
| 28 | 28.9 | 342 | 0.557 |
| 29 | 27.0 | 222.5 | Multimodal |
| 30 | 26.5 | 251.3 | 0.48 |
| 31 | 62.1 | 207.3 | 0.548 |
| 32 | 17.0 | 522.5 | 0.435 |
| 33 | 26.4 | 477.6 | Multimodal |
| 34 | 20.8 | 369.9 | 0.237 |
| 35 | 22.9 | 321.4 | 0.276 |
| 36 | 26.4 | 282.4 | 0.229 |
| 37 | 30.4 | 319.1 | 0.351 |
| 38 | 54.2 | 262.3 | 0.202 |
| 39 | 53.1 | 315.5 | 0.171 |
| 40 | 20.8 | 730.2 | Multimodal |
| 41 | 31.9 | 379.8 | 0.332 |
| 42 | 24.3 | 309.2 | 0.237 |
| 43 | 40.9 | 317.8 | 0.338 |
| 44 | 56.5 | 1186.1 | 0.271 |
| 45 | 37.7 | 386.4 | 0.153 |
| 46 | 43.2 | 279.6 | 0.138 |
| 47 | 14.7 | 413.3 | 0.29 |
| 48 | 23.6 | 351 | 0.218 |
| 49 | 24.2 | 266.7 | 0.524 |
| 50 | 24.0 | 249.3 | 0.401 |

TABLE 5-continued

| Summary of Pilot PNP Library Characterization Data | | | |
|---|---|---|---|
| PNP | Block 1 DynaPro Result (molar mass, kDa) | DynaPro DLS Z-Avg Result (size, nm) | Size PDI (goal < 0.3) |
| 51 | 29.0 | 269.9 | 0.371 |
| 52 | 105.1 | 271.2 | 0.074 |
| 53 | 30.4 | 302.5 | 0.145 |
| 54 | 18.0 | 375.2 | Multimodal |
| 55 | 20.5 | 440.4 | 0.496 |
| 56 | 19.0 | 296.3 | 0.109 |
| 57 | 24.8 | 277.1 | 0.475 |
| 58 | 34.7 | 299.6 | 0.393 |
| 59 | 36.0 | 269 | 0.351 |
| 60 | 34.9 | 264.8 | 0.181 |
| 61 | 40.5 | 353.1 | 0.138 |
| 62 | 41.3 | 230.5 | 0.151 |
| 63 | 16.2 | 354.5 | Multimodal |
| 64 | 15.0 | 355.5 | 0.334 |
| 65 | 23.7 | 332.6 | 0.231 |
| 66 | 26.6 | 253.4 | 0.217 |
| 67 | 34.6 | 294.3 | 0.151 |
| 68 | 44.3 | 275.2 | 0.207 |
| 69 | 45.6 | 404.8 | 0.287 |
| 70 | 9.4 | 2023.5 | 0.020 |
| 71 | 18.3 | 473.2 | 0.521 |
| 72 | 13.5 | 549.2 | 0.153 |
| 73 | 19.7 | 568 | Multimodal |
| 74 | 30.0 | 262 | 0.353 |
| 75 | 53.7 | 229.4 | Multimodal |
| 76 | 31.3 | 230.7 | 0.444 |
| 77 | 30.3 | 387.4 | Multimodal |
| 78 | 29.5 | 266.7 | Multimodal |
| 79 | 11.4 | 1155.7 | Multimodal |
| 80 | 21.3 | 619.2 | 0.198 |
| 81 | 28.9 | 337.7 | 0.053 |
| 82 | 17.5 | 336 | 0.13 |
| 83 | 28.8 | 90.5 | Multimodal |
| 84 | 19.0 | 251.3 | 0.164 |
| 85 | 21.1 | 360.6 | Multimodal |
| 86 | 18.8 | 225.3 | Multimodal |
| 87 | 22.4 | 168 | Multimodal |
| 88 | 13.1 | 298.6 | 0.217 |
| 89 | 11.0 | 281 | 0.314 |
| 90 | 16.3 | 300 | 0.503 |
| 91 | 29.0 | 214 | 0.293 |
| 92 | 9.1 | 14.2 | 0.412 |
| 93 | 3.9 | 21.2 | Multimodal |
| 94 | 15.6 | 432.8 | Multimodal |
| 95 | 13.2 | 268.9 | Multimodal |
| 96 | 14.2 | 657.2 | 0.356 |

Example 6

Figure 9:
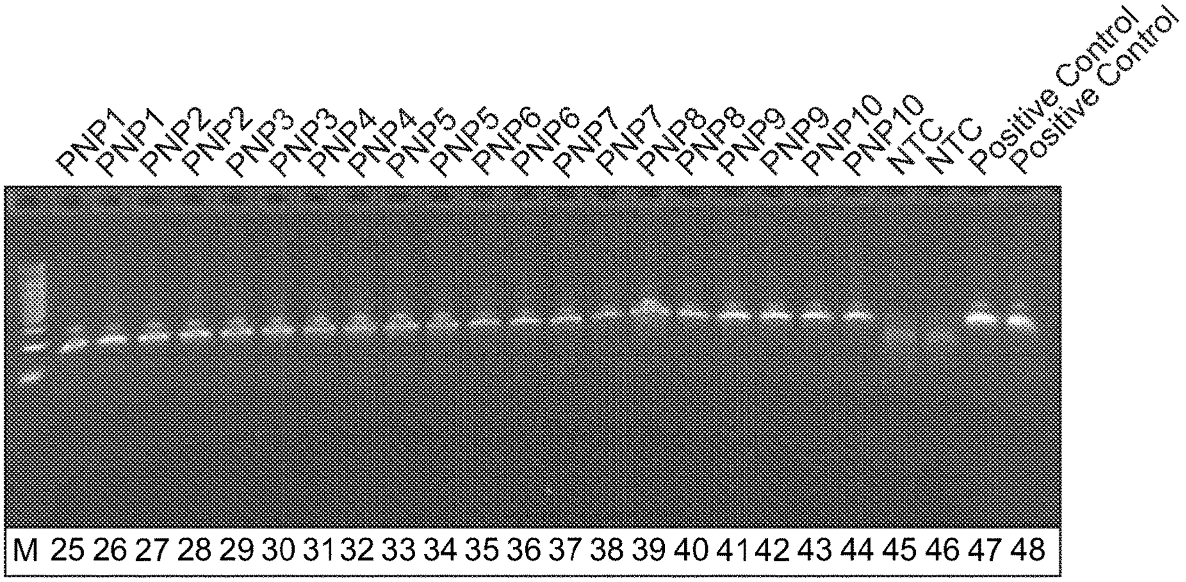
FIG. 9 is an e-gel showing DNA barcode amplification from 10 unique of PNPs with unique barcodes, after being spiked into HEK-293 cells. The presence of the double band is evidence of barcode amplification, present in the positive control sample known to have the barcodes, and not observed in the no test control (NTC) sample, which was phosphate buffered saline only.

Composition Example 3 (CE3): Nucleic Acid Constructs Conjugation to PNPs Direct Amidification with an Amine Terminal Nucleic Acid Construct RAFT copolymers made using CTAs that contain at least one carboxyl terminal group were further functionalized with amine terminal DNA barcodes. A RAFT copolymer was transferred into a MES buffer at ~12 mg/mL. The sample was sonicated for 30 minutes. EDC reagent and Sulfo-NHS reagent was added to the polymer at a molar ratio of 10:1 and 25:1 respectively, reagent to PNP. The sample was incubated for at least 10 minutes at room temperature to allow the reaction to occur. The reaction volume was filtered through a membrane with a molecular weight cut off of 30 kDa via centrifuge at ~3000×g for ~15 minutes. The filtrate was discarded, and sterile PBS was added to the retentate to reconstitute to 10 mg/mL polymer. A nucleic acid constructs with a primary amine group attached to the 5' end was added to polymer and the sample was incubated for at least 15 minutes. The sample was transferred to an amicon ultra-4 centrifuge tube (MWCO 30 kDa, Max 3.5 mL/Tube) and centrifuged at 4,000×g for 15 minutes to remove any unbound nucleic acid constructs. The filtrate (containing unbound nucleic acid constructs) was discarded and sterile PBS was added to the retentate to final concentration of 8 mg/mL polymer. The conjugated barcodes were amplified via PCR, using primers designed to bind to the primer binding segments on the nucleic acid constructs. The amplicons were detected via gel electrophoresis on agarose gel. The presence of a double band (FIG. 9) in a lane indicates the presence of amplicons, showing that nucleic acid constructs were bound to the PNPs.

The direct amidification method was used to attach 10 unique barcodes to 10 unique PNPs. The 10 unique PNPs were prepared according to the reagents shown in EXAMPLE 5.

Figure 10:
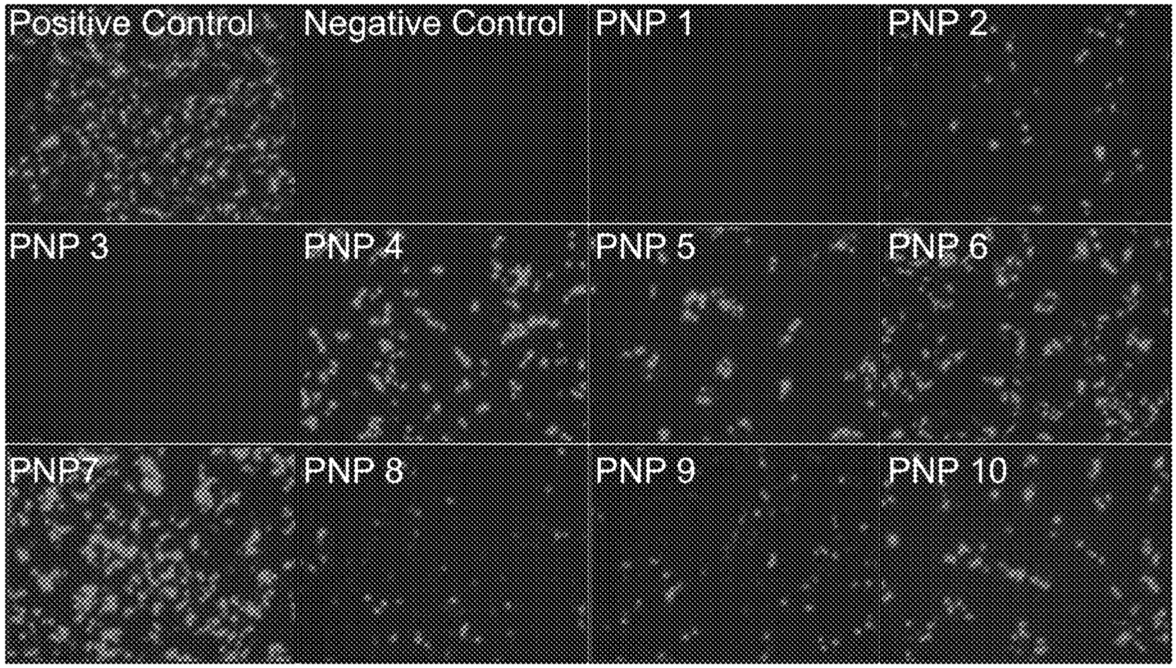
FIG. 10 is a series of images showing each of the 10 unique barcoded PNPs from FIG. 7 were loaded with a plasmid expressing a fluorescent TdTomato protein. The loaded PNPs were each dosed into HEK-293 cells. After 48 hours, the cells were imaged via fluorescent microscopy with a Texas Red filter, and the images are shown above.
Figure 11A:
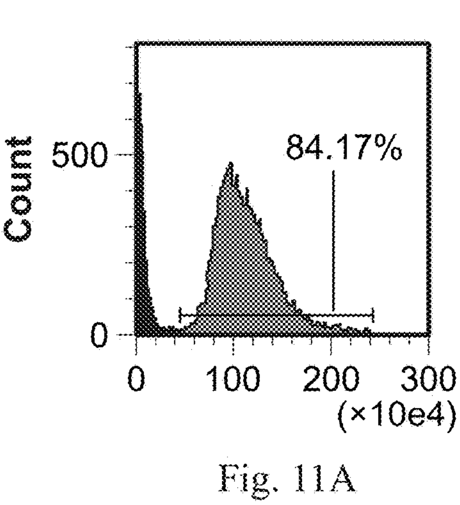
FIG. 11(*a*)-FIG. 11(*e*) show flow cytometry scatter plots depicting cell event distribution of HEK293T cells treated with a representative PNP carrying a td-tomato encoding fluorescent cargo plasmid (FIGS. 11(*a*)-11(*c*)), and heat maps depicting Transfection efficiency and viability of a library of 88 diverse PNPs (PNP Library Transfection Efficiency (FIG. 11(*d*)) and PNP Library Viability (FIG. 11(*e*))).
Figure 11B:
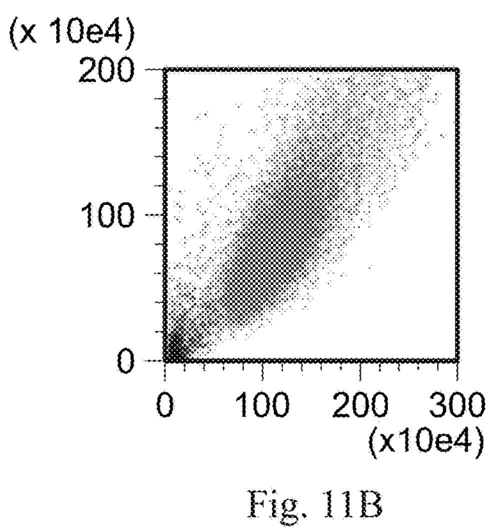
Figure 11C:
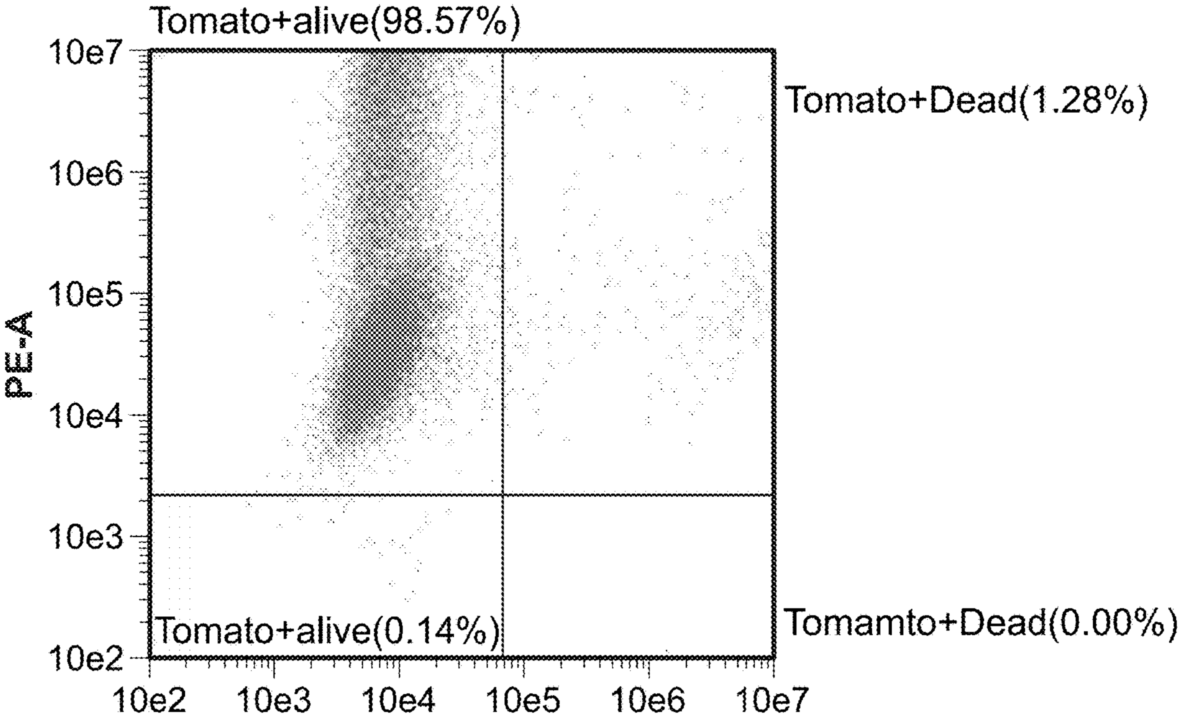
Figure 11D:
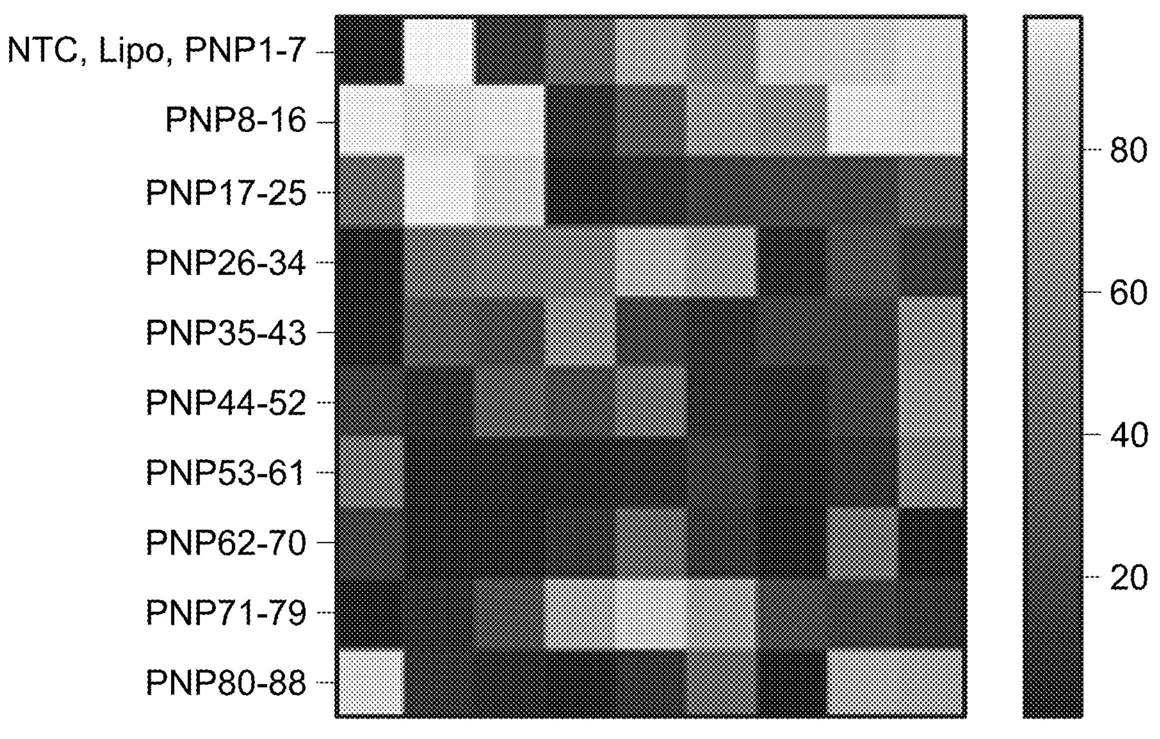
Figure 11E:
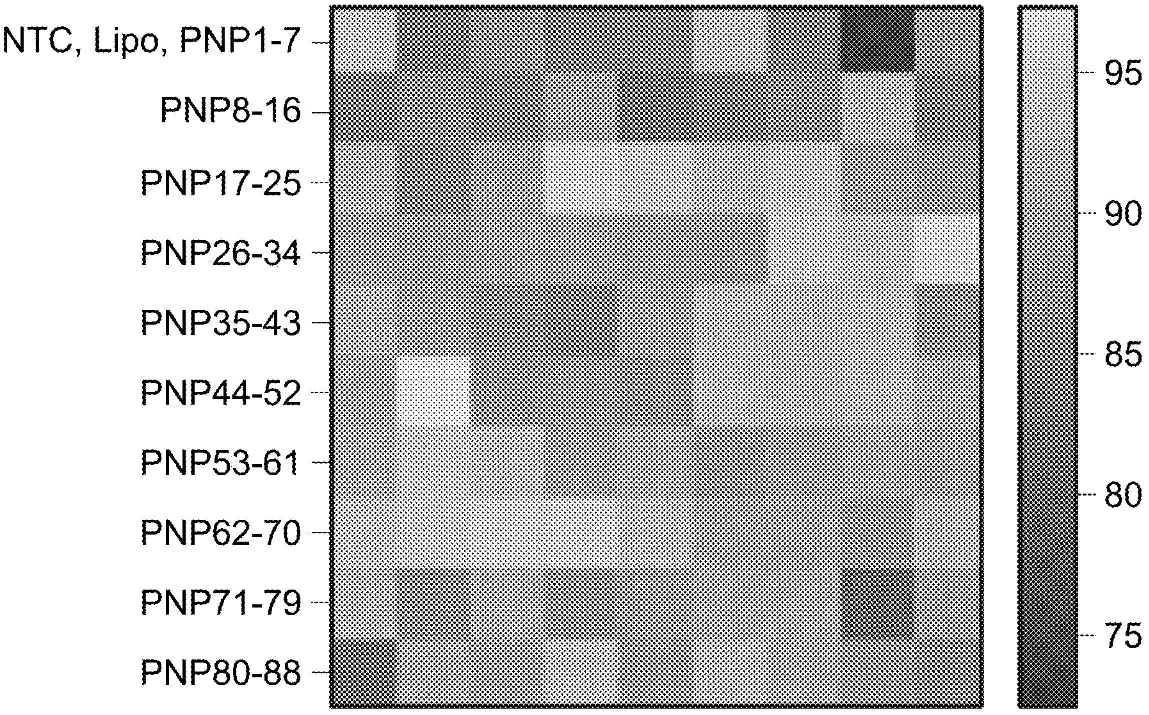

Subsequently, the direct amidification method was used to attach 10 unique DNA barcodes to each PNP, giving each a unique label. The nucleic acid construct-PNPs were loaded with a pDNA encoding for the expression of tdTomato red fluorescent protein, and then used to treat HEK-293T cells at ~0.024 mg/mL PNP, 24 hours after seeding in a 96 well plate at 20,000 cells per well. They were left to incubate for another 48 hours, at which time, expression of the payload was observed via fluorescence microscopy using a Texas Red filter set (FIG. 10). This provides evidence that the nucleic acid constructs-PNPs are capable of being taken up by mammalian cells and delivering a payload, as indicated by the red fluorescent images.

The direct amidification method was then used to attach 88 unique barcodes to 88 unique PNPs. The 88 unique PNPs were prepared according to the reagents shown in EXAMPLE 5. The amidification method was then used to attach 88 unique DAN barcodes to each PNP giving each a unique label. The nucleic acid construct-PNPs were loaded with a pDNA encoding for the expression of tdTomato red fluorescent protein, and then used to treat HEK-293T cells at ~0.024 mg/mL PNP, 24 hours after seeding in a 96 well plate at 20,000 cells per well. They were left to incubate for another 48 hours, at which time, expression of the payload was measured via flow cytometry using a Cytoflex (FIGS. 11(*a*)-(*c*)). This provided evidence that some of the nucleic acid construct-PNPs were able to be taken up by mammalian cells. The cells were also given a live/dead stain using zombie dye, and cell viability was measured via flow cytometry (FIGS. 11(*d*)-(*e*)) showing that the PNPs were of relatively low cytotoxicity, with cell viability numbers of greater than 75% for the vast majority of PNPs.

Example 7

Methods for Screening Nucleic Acid Construct-PNPs in Vitro and in Vivo

The pooled sample of polymer nanoparticles produced from the recipe in Table 2, with 96 unique barcodes attached via avidin-biotin linkage, was used for measuring cell uptake and cytotoxicity in vitro in HEK293T cells, and for measuring biodistribution in vivo administration in mice. nucleic acid construct-PNPs were formulated in a sterile saline solution and stored at 4° C. for up to 1 month prior to in vivo dosing. Cell uptake efficiency and cytotoxicity are assessed in vitro using HEK293T cells with 0.024 mg/mL PNP at 250 ng or 150 ng/well pDNA treatment concentrations. Cell uptake was demonstrated by fluorescence microscopy. Animals are assigned to dose groups using a stratified randomization program designed to maintain similar group mean body weights by sex. Animals are administered either a control or test article via a single bolus intravenous tail-vein injections. Tested doses ranged from 0-150 mg/kg, with adverse clinical events being observed in 35% of animals at 150 mg/kg. Blood and tissue are collected from all animals and snap frozen in liquid nitrogen.

Example 8

Extraction of Nucleic Acid Construct-PNPs from In Vitro Biological Samples 10-20 mg of tissues are placed in a Tris-EDTA lysis buffer and homogenized using the TissueLyser bead-beating system and a 5 mm stainless steel bead. Homogenization is carried out at 25 Hz in 5-7 minute intervals until solution is homogenous in appearance. Proteinase K is then added to the lysate for protein digestion and incubated in a Thermomixer at 55° C. for 2-4 hours. DNA is extracted from the tissue lysate using the QIAamp 96 DNA extraction kit and a Qiacube HT instrument according to the manufacturer's protocol. Concentration and purity of isolated samples is determined using a NanoDrop.

Example 9

PCR Amplification of Polynucleotide Barcodes in Nucleic Acid Constructs

Polymerase chain reaction is used to produce amplicons from extracted nucleic acid constructs. PCR is performed using a single set of universal primers that anneal to the universal amplification sites on the barcode, thereby amplifying all unique barcodes within a sample in a single reaction. Positive amplification of barcode(s) within a sample is determined using electrophoresis (agarose gel or bioanalyzer) indicated by the presence of a band at ~120 bp.

Example 10

Library Preparation and Sequencing of Nucleic Acid Constructs

Sequencing libraries are prepared from the amplicons generated during first stage PCR amplification. Our universal primers also contain overhang sequences that enable attachment of Index Adapters for sequencing. Illumina Unique Dual Indexes are annealed to the overhangs on the amplicon by PCR. Individual indexed libraries are then pooled in equal amounts and purified using a NucleoSpin Gel and PCR Clean-up kit according the manufacturer's protocols. The molar concentration of the final sequencing library is determined using a Qubit dsDNA High Sensitivity Assay kit and Qubit Fluorometer. The library is spiked with 2% PhiX, diluted to 1.8 μM and loaded onto a High Output 300 cycle NextSeq sequencing cartridge. Paired end sequencing is performed using a NextSeq550 instrument.

Example 11

Sequence Analysis and Bioinformatics

Merged reads from each Sample ID are demultiplexed into PE FASTQ files, and merged into a single file. The merged reads are processed to identify those containing both the 5' and 3' flanking adapters. Trimmed reads are then downselected for sequences containing the correct barcode length. Barcode counts are generated from these downselected sequences and tagged according to whether they are spiked or random. Barcode counts are then normalized to the number of FASTQ reads in the sample.

Hypothetical Example

By way of example, in one illustrative embodiment, the presently disclosed rapid DBTL technologies may be used to develop a gene therapy for forms of amyotrophic lateral sclerosis (ALS) caused by toxic, gain-of-function mutations in superoxide dismutase 1 (SOD1). This gene therapy may involve delivering a CRISPR base-editing protein via a non-viral gene delivery vehicle to inactivate the production of mutant SOD1 protein in microglia, a cell type that modulates the progression of the disease but remains refractory to efficient viral transduction. This will enable safe and efficient therapeutic "hit-and-run" editing for ALS.

An exemplary disease that can be treated with the methods described herein is ALS. ALS is a rapidly progressive, paralytic, and invariably fatal disorder characterized by the selective loss of motor neurons in the spinal cord and brain. Though most cases of ALS are sporadic, dominantly inherited mutations in SOD1 (a ubiquitously expressed metalloenzyme that normally converts superoxide anions into oxygen and hydrogen peroxide) account for up to 20% of all inherited or familial forms of ALS. Base editors are a recently emerged gene-editing modality capable of introducing targeted single-base substitutions in DNA without the requirement for a double-strand break (DSB). Base editors consist of fusions of a catalytically impaired Cas9 nuclease variant, known as a Cas9 nickase, with a nucleobase deaminase enzyme. This example will rely on the ability of base editors, specifically cytidine base editors (CBEs), to catalyze C>T base transitions at CGA, CAG or CAA triplets in a target gene sequence, which creates an in-frame stop codon that triggers the degradation of a target mRNA by nonsense-mediated decay—a surveillance mechanism used by cells to prevent the formation of truncated proteins. Using this method, SOD1 will be inactivated in a manner that does not require a DSB and does not rely on the stochastic and mutagenic NHEJ repair pathway, thus overcoming two of the major limitations facing the clinical implementation of CRISPR-Cas9 for ALS. Thus, while first generation CRISPR is considered the "cut and paste" of gene editing, base editors are considered to be an "eraser and pencil" function, allowing for precise single base edits to a genome, opening new mechanisms for revolutionary ALS treatments. However, innovations in gene delivery have significantly lagged innovations in technologies for gene editing itself. Thus, efficient delivery of base editing systems to the specific cell types involved in driving the progression of ALS represents a key limitation impeding its safe and efficient implementation for treatment of the disorder. Non-viral delivery vehicles will be used to address many of these limitations.

In this illustrative example, the rapid DBTL technologies can iterate through hundreds of diverse polymer nanoparticle candidates, using automated high-throughput synthesis of diverse polymer nanoparticle libraries, parallel in vitro and in vivo screens of barcoded libraries, and a machine learning algorithm to analyze the large data sets and predict new libraries for rapid iteration. FIG. 1 presents a simplified flow diagram illustrating a DBTL cycle for non-viral gene delivery development based on automated synthesis, high throughput testing, and machine learning design.

Hypothetical Example

Figure 2:
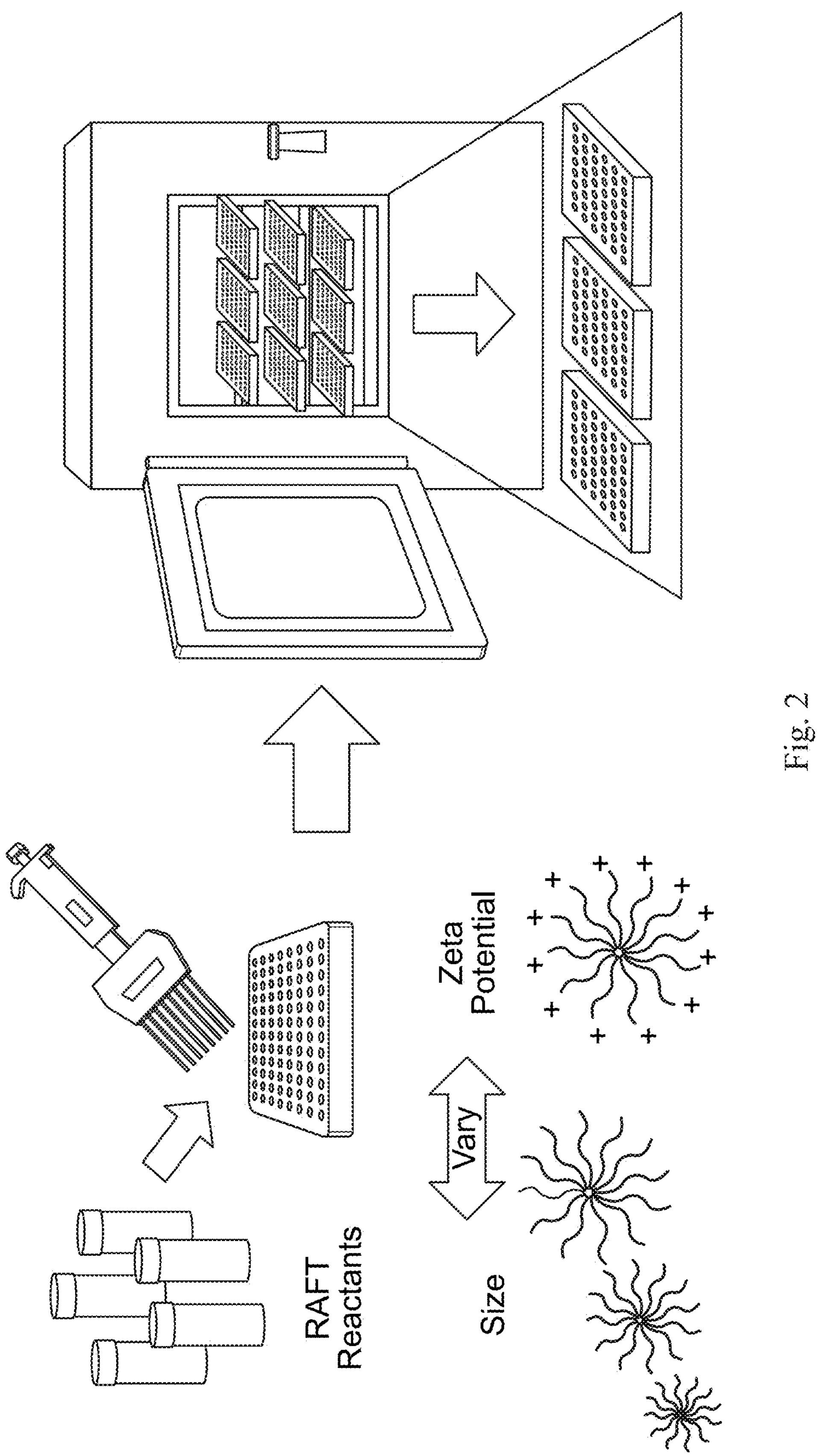
FIG. 2 is a schematic diagram showing an automated multiplexed synthesis of a large, diverse library of PNPs, with various size, charge and hydrophobicity to generate data for gene editing, cytotoxicity, and inflammation.

In one aspect, a library of 100s of polymer nanoparticles (PNPs) encapsulating CBE mRNA can be screened in a high throughput in vitro and in vivo platform. In the illustrative embodiment, over 500 PNPs are synthesized and uniquely labeled and tracked via DNA barcoding. A highly versatile PNP platform based on reversible addition-fragmentation chain transfer (RAFT) polymerization will be used due to its flexibility, reproducibility, and scalability. See K. Sims et al., "Rigor and reproducibility in polymer nanoparticle synthesis and characterization," *Rsc Advances* 2020, 10 (5), 2513-2518 (incorporated herein by reference). As shown in FIG. 2, the RAFT polymerization platform can be used to generate highly monodisperse PNPs with a diverse variety of sizes, charges and chemical make-up. The PNPs can be functionalized to attach cell penetrating peptides to enable higher order functionality and protection to both the vehicle and the cargo. In some embodiments, PNPs may be labeled with quantum dots and other biomarkers via avidin-biotin conjugation. See A. Duong et al., "Scalable, Semicontinuous Production of Micelles Encapsulating Nanoparticles via Electrospray," *Langmuir* 2014, 30 (14), 3939-3948. (incorporated herein by reference). This combination of microglia non-viral delivery vehicles with base editing payloads is highly innovative because it has the potential to lead to a new therapy for ALS. Moreover, the DBTL technologies of the present disclosure are generalizable to enable the creation of advanced non-viral delivery vehicles capable of accessing the other cell types involved in ALS.

After library synthesis, as described above, these PNPs can then be rapidly tested in vitro in a microglial cell line for toxicity, inflammation, and mRNA delivery efficiency via GFP expression. In parallel, the biodistribution and toxicity of the entire library can be assessed using loaded nanoparticles delivered via an intrathecal injection to the cerebrospinal fluid (CSF) of the G93A-SOD1 mouse model of ALS using an mRNA encoding a bioluminescent luciferase that can be tracked via in vitro imaging system (IVIS). This screen should result in three large data sets including particle physical characteristics, in vitro bioactivity, and in vivo biodistribution and toxicity, which, taken together, will provide the basis for an informed design of a novel non-viral delivery vehicle library which will be synthesized in a second iteration. This novel library can then be tested for functional gene editing tests in a microglial cell line modified to express a mutant SOD1 protein. The PNPs can be loaded with mRNA encoding CBE designed to inactivate GFP and SOD1, detected by fluorescence measurement and sequencing.

We claim:

1. A composition comprising:

a non-viral delivery vehicle comprising one or more nanoparticle forming polymers, and a nucleic acid construct, comprising:

two primer binding segments; and one or more unique polynucleotide barcodes between the two primer binding segments, wherein the nucleic acid construct is:

electrostatically associated with the nanoparticle forming polymers;

bonded to the nanoparticle forming polymers via complexation of biotin and a biotin binding molecule; or covalently bonded to the nanoparticle forming polymers, wherein the one or more nanoparticle forming polymers are RAFT block copolymers comprising:

a. a first terminus comprising a first capping unit derived from a first chain transfer agent in a RAFT copolymerization process;

b. a first block prepared from one or more monomer units covalently attached to the first reactive functional unit, and having a molecular weight ($M_n$) in the range of about 1 kDa to about 200 kDa and a degree of polymerization in the range of about 10 to about 2500;

c. optionally a second block prepared from one or more monomer units covalently attached to the first block, and having a molecular weight ($M_n$) in the range of about 1 kDa to about 200 kDa and a degree of polymerization in the range of about 20 to about 2000; and d. a second terminus comprising a second capping unit derived from a first or a second chain transfer agent.

2. The composition of claim 1, wherein the non-viral delivery vehicle has one or more of an overall molecular weight ($M_n$) in the range of about 25 kDa to about 60 kDa, an overall degree of polymerization in the range of about 700 to about 900, a target size in the range of about of about 10 to about 60 nm, and a maximum corona-to-core ratio (CCR) of about 1.5 to about 3.5.

3. The composition of claim 1, wherein the first block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl) methacrylate, and methyl methacrylate.

4. The composition of claim 1, wherein the first block is prepared from one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl) methacrylate, or methyl methacrylate.

5. The composition of claim 1, wherein the second block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxy ethyl methacrylate, and methyl methacrylate.

6. The composition of claim 1, wherein the second block is a random copolymer prepared from two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, hydroxy ethyl methacrylate, and methyl methacrylate.

7. The composition of claim 1, wherein the second block is a random copolymer prepared from three different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxy ethyl) methacrylate, and methyl methacrylate.

8. The composition of claim 1, wherein the second block is a random copolymer prepared from 2-dimethylaminoethyl acrylate, butyl methacrylate, and propyl acrylic acid; or 2-dimethylaminoethyl acrylate and butyl methacrylate; or 2-dimethylaminoethyl acrylate, butyl methacrylate, and ethyl acrylic acid.

9. The composition of claim 1, wherein the nucleic acid construct is electrostatically associated with the nanoparticle forming polymers.

10. The composition of claim 1, wherein the nucleic acid construct is bonded to the nanoparticle forming polymers via complexation of biotin and a biotin binding molecule.

11. The composition of claim 1, wherein the nucleic acid construct is covalently bonded to the nanoparticle forming polymers.

12. The composition of claim 1, wherein the primer binding segments range in length from about 15 base pairs to about 30 base pairs.

13. The composition of claim 1, wherein the primer binding segments are a universal primer binding set.

14. The composition of claim 1, wherein the one or more polynucleotide barcodes comprise unique sequences of 6-20 nucleotides in length.

15. The composition of claim 14, wherein the polynucleotide barcodes further comprise a hamming distance of at least 2-6 bases between any two unique polynucleotide barcode sequences.

16. The composition of claim 1, wherein the nucleic acid construct further comprises from about 6 to about 12 random bases at the 3' end of the polynucleotide barcode.

17. The composition of claim 16, wherein the about 6 to about 12 random bases at the 3' end of the polynucleotide barcode are for bioinformatic removal of PCR duplicates.

18. The composition of claim 1, wherein the nucleic acid construct ranges in length from about 42 nucleotides to about 210 nucleotides.

* * * * *

SEQUENCE LISTING

```
Sequence total quantity: 1003
SEQ ID NO: 1            moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 1
gctacataat                                                            10

SEQ ID NO: 2            moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 2
atgttacaca                                                            10

SEQ ID NO: 3            moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 3
tggggcccaa                                                            10

SEQ ID NO: 4            moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 4
tagtttatcc                                                            10

SEQ ID NO: 5            moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 5
accccgtctt                                                            10

SEQ ID NO: 6            moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 6
ccggccatca                                                            10

SEQ ID NO: 7            moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 7
gagcttgctc                                                            10
```

-continued

```
SEQ ID NO: 8              moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 8
acgttctata                                                            10

SEQ ID NO: 9              moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 9
tacagcaaaa                                                            10

SEQ ID NO: 10             moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 10
gttaggtggt                                                            10

SEQ ID NO: 11             moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 11
ggagaccgac                                                            10

SEQ ID NO: 12             moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 12
tggccccttg                                                            10

SEQ ID NO: 13             moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 13
tggccgtaag                                                            10

SEQ ID NO: 14             moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 14
cgttcgtcaa                                                            10

SEQ ID NO: 15             moltype = DNA  length = 10
FEATURE                   Location/Qualifiers
```

```
misc_feature          1..10
                      note = Description of Artificial Sequence: Synthetic
                       oligonucleotide
source                1..10
                      mol_type = other DNA
                      organism = synthetic construct
SEQUENCE: 15
cggacgtgga                                                                  10

SEQ ID NO: 16         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 16
agagggggca                                                                  10

SEQ ID NO: 17         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 17
gttcaggtcg                                                                  10

SEQ ID NO: 18         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 18
ctcgcaagag                                                                  10

SEQ ID NO: 19         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 19
gcaacgactt                                                                  10

SEQ ID NO: 20         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 20
gccatccatc                                                                  10

SEQ ID NO: 21         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 21
ttccgagcag                                                                  10

SEQ ID NO: 22         moltype = DNA  length = 10
FEATURE               Location/Qualifiers
misc_feature          1..10
                      note = Description of Artificial Sequence: Synthetic
```

```
                        oligonucleotide
source                  1..10
                        mol_type = other DNA
                        organism = synthetic construct
SEQUENCE: 22
cttctggaca                                                    10

SEQ ID NO: 23           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 23
aacattagac                                                    10

SEQ ID NO: 24           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 24
aagcaatagt                                                    10

SEQ ID NO: 25           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 25
agggtaagac                                                    10

SEQ ID NO: 26           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 26
cgttgtcttg                                                    10

SEQ ID NO: 27           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 27
tttccccgcc                                                    10

SEQ ID NO: 28           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 28
cgaatggatc                                                    10

SEQ ID NO: 29           moltype = DNA  length = 10
FEATURE                 Location/Qualifiers
misc_feature            1..10
                        note = Description of Artificial Sequence: Synthetic
                         oligonucleotide
source                  1..10
```

```
                         mol_type = other DNA
                         organism = synthetic construct
SEQUENCE: 29
catcacttgc                                                           10

SEQ ID NO: 30            moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 30
ctctcgcact                                                           10

SEQ ID NO: 31            moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 31
gttcacgtgc                                                           10

SEQ ID NO: 32            moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 32
aataagcctg                                                           10

SEQ ID NO: 33            moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 33
gttaacaatt                                                           10

SEQ ID NO: 34            moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 34
attcagatcc                                                           10

SEQ ID NO: 35            moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 35
cctgctgatt                                                           10

SEQ ID NO: 36            moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
```

```
SEQUENCE: 36
cttggtcata                                                     10

SEQ ID NO: 37          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 37
tcttcctgtt                                                     10

SEQ ID NO: 38          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 38
actgccatgg                                                     10

SEQ ID NO: 39          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 39
catgtatagt                                                     10

SEQ ID NO: 40          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 40
ggtagcggca                                                     10

SEQ ID NO: 41          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 41
tcactctaac                                                     10

SEQ ID NO: 42          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 42
aaggtgcacc                                                     10

SEQ ID NO: 43          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 43
aatgctcgtt                                                     10
```

```
SEQ ID NO: 44          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 44
tgtctagaaa                                                                10

SEQ ID NO: 45          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 45
ctgcctgcct                                                                10

SEQ ID NO: 46          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 46
actataaaag                                                                10

SEQ ID NO: 47          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 47
tagtatcgag                                                                10

SEQ ID NO: 48          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 48
atcgcagtcc                                                                10

SEQ ID NO: 49          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 49
tcatcagaac                                                                10

SEQ ID NO: 50          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 50
tcctagacgc                                                                10

SEQ ID NO: 51          moltype = DNA  length = 10
```

```
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 51
gccgggcggg                                                              10

SEQ ID NO: 52          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 52
gcccagaaga                                                              10

SEQ ID NO: 53          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 53
cttagagctg                                                              10

SEQ ID NO: 54          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 54
gtctgcgctt                                                              10

SEQ ID NO: 55          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 55
cgccgtcctt                                                              10

SEQ ID NO: 56          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 56
tttatctgct                                                              10

SEQ ID NO: 57          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 57
tgcttcggag                                                              10

SEQ ID NO: 58          moltype = DNA  length = 10
FEATURE                Location/Qualifiers
misc_feature           1..10
```

```
                        note = Description of Artificial Sequence: Synthetic
                         oligonucleotide
source                  1..10
                        mol_type = other DNA
                        organism = synthetic construct
SEQUENCE: 58
ggggagaatg                                                                10

SEQ ID NO: 59           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 59
gtggtaagtg                                                                10

SEQ ID NO: 60           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 60
gaaattagta                                                                10

SEQ ID NO: 61           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 61
gctatcctaa                                                                10

SEQ ID NO: 62           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 62
atctgtacga                                                                10

SEQ ID NO: 63           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 63
agttcggggc                                                                10

SEQ ID NO: 64           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 64
cgagtctgtc                                                                10

SEQ ID NO: 65           moltype = DNA  length = 10
FEATURE                 Location/Qualifiers
misc_feature            1..10
                        note = Description of Artificial Sequence: Synthetic
                         oligonucleotide
```

```
source                1..10
                      mol_type = other DNA
                      organism = synthetic construct
SEQUENCE: 65
atcctacgca                                                   10

SEQ ID NO: 66         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 66
atggtggata                                                   10

SEQ ID NO: 67         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 67
cctctaacta                                                   10

SEQ ID NO: 68         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 68
atagctgcac                                                   10

SEQ ID NO: 69         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 69
gacagaattt                                                   10

SEQ ID NO: 70         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 70
caattggcat                                                   10

SEQ ID NO: 71         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 71
tctagtagac                                                   10

SEQ ID NO: 72         moltype = DNA  length = 10
FEATURE               Location/Qualifiers
misc_feature          1..10
                      note = Description of Artificial Sequence: Synthetic
                       oligonucleotide
source                1..10
                      mol_type = other DNA
```

```
                        organism = synthetic construct
SEQUENCE: 72
ttattcatgg                                                                   10

SEQ ID NO: 73           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 73
ttggcaaccg                                                                   10

SEQ ID NO: 74           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 74
cataatacat                                                                   10

SEQ ID NO: 75           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 75
acagactcac                                                                   10

SEQ ID NO: 76           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 76
gcgatgctgc                                                                   10

SEQ ID NO: 77           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 77
catctttgcc                                                                   10

SEQ ID NO: 78           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 78
gtgactccag                                                                   10

SEQ ID NO: 79           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 79
```

-continued

```
ggacgagtct                                                        10

SEQ ID NO: 80          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 80
tagtggcgtg                                                        10

SEQ ID NO: 81          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 81
aacgcagctt                                                        10

SEQ ID NO: 82          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 82
agaacaggtg                                                        10

SEQ ID NO: 83          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 83
aggctatgtt                                                        10

SEQ ID NO: 84          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 84
cctggatctt                                                        10

SEQ ID NO: 85          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 85
ctagccggcc                                                        10

SEQ ID NO: 86          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 86
accagttatc                                                        10
```

-continued

```
SEQ ID NO: 87           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 87
acgttatagc                                                            10

SEQ ID NO: 88           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 88
tcgagtttga                                                            10

SEQ ID NO: 89           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 89
tgaagcgagc                                                            10

SEQ ID NO: 90           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 90
gactggcgaa                                                            10

SEQ ID NO: 91           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 91
gatggaccta                                                            10

SEQ ID NO: 92           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 92
gtccacaacg                                                            10

SEQ ID NO: 93           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 93
cctccccaga                                                            10

SEQ ID NO: 94           moltype = DNA  length = 10
FEATURE                 Location/Qualifiers
```

```
misc_feature            1..10
                        note = Description of Artificial Sequence: Synthetic
                         oligonucleotide
source                  1..10
                        mol_type = other DNA
                        organism = synthetic construct
SEQUENCE: 94
ttatgacgcc                                                                  10

SEQ ID NO: 95           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 95
cttgatccgt                                                                  10

SEQ ID NO: 96           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 96
aatgcgcaat                                                                  10

SEQ ID NO: 97           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 97
gtacccctca                                                                  10

SEQ ID NO: 98           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 98
cgacagctcg                                                                  10

SEQ ID NO: 99           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 99
tgacctggct                                                                  10

SEQ ID NO: 100          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 100
ttcatagccc                                                                  10

SEQ ID NO: 101          moltype = DNA  length = 10
FEATURE                 Location/Qualifiers
misc_feature            1..10
                        note = Description of Artificial Sequence: Synthetic
```

```
                        oligonucleotide
source                 1..10
                       mol_type = other DNA
                       organism = synthetic construct
SEQUENCE: 101
cccaagagaa                                                   10

SEQ ID NO: 102         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 102
aaacgaagta                                                   10

SEQ ID NO: 103         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 103
gacgtttaca                                                   10

SEQ ID NO: 104         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 104
gatcgatttg                                                   10

SEQ ID NO: 105         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 105
cactgtcacc                                                   10

SEQ ID NO: 106         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 106
tgtgagagtt                                                   10

SEQ ID NO: 107         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 107
gacgtaacct                                                   10

SEQ ID NO: 108         moltype = DNA  length = 10
FEATURE                Location/Qualifiers
misc_feature           1..10
                       note = Description of Artificial Sequence: Synthetic
                        oligonucleotide
source                 1..10
```

```
                         mol_type = other DNA
                         organism = synthetic construct
SEQUENCE: 108
cagactctgc                                                         10

SEQ ID NO: 109           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 109
tatgccaata                                                         10

SEQ ID NO: 110           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 110
acaggtgatg                                                         10

SEQ ID NO: 111           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 111
gtcatcgcgt                                                         10

SEQ ID NO: 112           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 112
tcttataaac                                                         10

SEQ ID NO: 113           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 113
gtgtagactg                                                         10

SEQ ID NO: 114           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 114
aaacaaccgg                                                         10

SEQ ID NO: 115           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
```

```
SEQUENCE: 115
atcctgtacc                                                        10

SEQ ID NO: 116          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 116
ttataagaat                                                        10

SEQ ID NO: 117          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 117
ataagtaggc                                                        10

SEQ ID NO: 118          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 118
tctcgtaagg                                                        10

SEQ ID NO: 119          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 119
gatccgccgc                                                        10

SEQ ID NO: 120          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 120
tgtcaggttt                                                        10

SEQ ID NO: 121          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 121
tccgaagccc                                                        10

SEQ ID NO: 122          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 122
tccatgtcca                                                        10
```

```
SEQ ID NO: 123          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 123
gtgatggtac                                                            10

SEQ ID NO: 124          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 124
ctccacatac                                                            10

SEQ ID NO: 125          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 125
ttcggatgag                                                            10

SEQ ID NO: 126          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 126
acgacatcgc                                                            10

SEQ ID NO: 127          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 127
gagatgcaca                                                            10

SEQ ID NO: 128          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 128
tttgtatggc                                                            10

SEQ ID NO: 129          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 129
cttttctaga                                                            10

SEQ ID NO: 130          moltype = DNA  length = 10
```

```
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 130
agtctaatca                                                      10

SEQ ID NO: 131          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 131
gacttagcca                                                      10

SEQ ID NO: 132          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 132
tatcacagta                                                      10

SEQ ID NO: 133          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 133
aagctcgagt                                                      10

SEQ ID NO: 134          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 134
tgttacgaca                                                      10

SEQ ID NO: 135          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 135
aaggatagtc                                                      10

SEQ ID NO: 136          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 136
gcacttagcc                                                      10

SEQ ID NO: 137          moltype = DNA  length = 10
FEATURE                 Location/Qualifiers
misc_feature            1..10
```

```
                      note = Description of Artificial Sequence: Synthetic
                       oligonucleotide
source                1..10
                      mol_type = other DNA
                      organism = synthetic construct
SEQUENCE: 137
gagggatccg                                                   10

SEQ ID NO: 138        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 138
attctagaag                                                   10

SEQ ID NO: 139        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 139
gataactgat                                                   10

SEQ ID NO: 140        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 140
atctgactgt                                                   10

SEQ ID NO: 141        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 141
caaagcgaac                                                   10

SEQ ID NO: 142        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 142
gaaattgcga                                                   10

SEQ ID NO: 143        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 143
gggtccagtc                                                   10

SEQ ID NO: 144        moltype = DNA  length = 10
FEATURE               Location/Qualifiers
misc_feature          1..10
                      note = Description of Artificial Sequence: Synthetic
                       oligonucleotide
```

```
source                 1..10
                       mol_type = other DNA
                       organism = synthetic construct
SEQUENCE: 144
atcaggtagc                                                              10

SEQ ID NO: 145         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 145
gaaaggtcct                                                              10

SEQ ID NO: 146         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 146
ggctaccaca                                                              10

SEQ ID NO: 147         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 147
ttattgctga                                                              10

SEQ ID NO: 148         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 148
cgccgcgttt                                                              10

SEQ ID NO: 149         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 149
ttttcaaaag                                                              10

SEQ ID NO: 150         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 150
ctgggctaaa                                                              10

SEQ ID NO: 151         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
```

```
                        organism = synthetic construct
SEQUENCE: 151
cccgatgaga                                                                10

SEQ ID NO: 152          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 152
tgggaaatat                                                                10

SEQ ID NO: 153          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 153
gtacgagcgg                                                                10

SEQ ID NO: 154          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 154
gcgtgcagct                                                                10

SEQ ID NO: 155          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 155
agtctgcgga                                                                10

SEQ ID NO: 156          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 156
taactattta                                                                10

SEQ ID NO: 157          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 157
gagttgccgg                                                                10

SEQ ID NO: 158          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 158
```

```
cagcccggcg                                                          10

SEQ ID NO: 159          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 159
tcacctacat                                                          10

SEQ ID NO: 160          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 160
agtggctaac                                                          10

SEQ ID NO: 161          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 161
agaatgtgag                                                          10

SEQ ID NO: 162          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 162
tagtttcgca                                                          10

SEQ ID NO: 163          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 163
cttcatttct                                                          10

SEQ ID NO: 164          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 164
gccatgatat                                                          10

SEQ ID NO: 165          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 165
acggcaaatc                                                          10
```

-continued

```
SEQ ID NO: 166          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 166
atcgatagta                                                            10

SEQ ID NO: 167          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 167
cctaaaggca                                                            10

SEQ ID NO: 168          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 168
tacgagcggt                                                            10

SEQ ID NO: 169          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 169
tttgtcgtcg                                                            10

SEQ ID NO: 170          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 170
tacaagcttg                                                            10

SEQ ID NO: 171          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 171
gaccaacacg                                                            10

SEQ ID NO: 172          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 172
gaacgacgaa                                                            10

SEQ ID NO: 173          moltype = DNA  length = 10
FEATURE                 Location/Qualifiers
```

```
misc_feature            1..10
                        note = Description of Artificial Sequence: Synthetic
                         oligonucleotide
source                  1..10
                        mol_type = other DNA
                        organism = synthetic construct
SEQUENCE: 173
tcggaacgca                                                                  10

SEQ ID NO: 174          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 174
atccggtggt                                                                  10

SEQ ID NO: 175          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 175
taaaacgtag                                                                  10

SEQ ID NO: 176          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 176
tatgtgagcc                                                                  10

SEQ ID NO: 177          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 177
gaggcatcga                                                                  10

SEQ ID NO: 178          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 178
gaatgggtgg                                                                  10

SEQ ID NO: 179          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 179
aacgacacaa                                                                  10

SEQ ID NO: 180          moltype = DNA  length = 10
FEATURE                 Location/Qualifiers
misc_feature            1..10
                        note = Description of Artificial Sequence: Synthetic
```

```
                        oligonucleotide
source                  1..10
                        mol_type = other DNA
                        organism = synthetic construct
SEQUENCE: 180
gtacgatgca                                                    10

SEQ ID NO: 181          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 181
agaaggcgcc                                                    10

SEQ ID NO: 182          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 182
ccgcaatgga                                                    10

SEQ ID NO: 183          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 183
tacggatttt                                                    10

SEQ ID NO: 184          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 184
gtcgttagct                                                    10

SEQ ID NO: 185          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 185
ggactagggc                                                    10

SEQ ID NO: 186          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 186
attggtattc                                                    10

SEQ ID NO: 187          moltype = DNA  length = 10
FEATURE                 Location/Qualifiers
misc_feature            1..10
                        note = Description of Artificial Sequence: Synthetic
                         oligonucleotide
source                  1..10
```

```
                        mol_type = other DNA
                        organism = synthetic construct
SEQUENCE: 187
atcccagaga                                                      10

SEQ ID NO: 188          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 188
gtcccagctc                                                      10

SEQ ID NO: 189          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 189
cacgaggaat                                                      10

SEQ ID NO: 190          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 190
tacaattgca                                                      10

SEQ ID NO: 191          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 191
attcctgaat                                                      10

SEQ ID NO: 192          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 192
tagcgaggcg                                                      10

SEQ ID NO: 193          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 193
ctggatgggc                                                      10

SEQ ID NO: 194          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
```

-continued

```
SEQUENCE: 194
gcgacggcca                                                   10

SEQ ID NO: 195          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 195
acctgcacaa                                                   10

SEQ ID NO: 196          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 196
catgacagac                                                   10

SEQ ID NO: 197          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 197
ttaccaacgt                                                   10

SEQ ID NO: 198          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 198
caggtgtgtg                                                   10

SEQ ID NO: 199          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 199
cgagggacgg                                                   10

SEQ ID NO: 200          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 200
cgtctcggta                                                   10

SEQ ID NO: 201          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 201
taagctatct                                                   10
```

-continued

```
SEQ ID NO: 202          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 202
tactcccta                                                             10

SEQ ID NO: 203          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 203
ttatattcat                                                            10

SEQ ID NO: 204          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 204
agcgatctgc                                                            10

SEQ ID NO: 205          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 205
tcttctgatc                                                            10

SEQ ID NO: 206          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 206
atagttccca                                                            10

SEQ ID NO: 207          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 207
tttacgggtg                                                            10

SEQ ID NO: 208          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 208
gtgtcccctg                                                            10

SEQ ID NO: 209          moltype = DNA  length = 10
```

```
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 209
gcgggggtcg                                                                   10

SEQ ID NO: 210         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 210
cattgatcta                                                                   10

SEQ ID NO: 211         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 211
agggacggtg                                                                   10

SEQ ID NO: 212         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 212
cagttacttt                                                                   10

SEQ ID NO: 213         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 213
ccatacttcc                                                                   10

SEQ ID NO: 214         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 214
atcagaatta                                                                   10

SEQ ID NO: 215         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 215
aaactaggca                                                                   10

SEQ ID NO: 216         moltype = DNA  length = 10
FEATURE                Location/Qualifiers
misc_feature           1..10
```

```
                        note = Description of Artificial Sequence: Synthetic
                         oligonucleotide
source                  1..10
                        mol_type = other DNA
                        organism = synthetic construct
SEQUENCE: 216
aatgtcgttg                                                                  10

SEQ ID NO: 217          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 217
cacatgggtc                                                                  10

SEQ ID NO: 218          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 218
ggtcgctggt                                                                  10

SEQ ID NO: 219          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 219
actgtattac                                                                  10

SEQ ID NO: 220          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 220
ccgagacgcg                                                                  10

SEQ ID NO: 221          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 221
actccaaccc                                                                  10

SEQ ID NO: 222          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 222
atattacaag                                                                  10

SEQ ID NO: 223          moltype = DNA  length = 10
FEATURE                 Location/Qualifiers
misc_feature            1..10
                        note = Description of Artificial Sequence: Synthetic
                         oligonucleotide
```

```
source                  1..10
                        mol_type = other DNA
                        organism = synthetic construct
SEQUENCE: 223
ccatggatag                                                              10

SEQ ID NO: 224          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 224
ccgtctcaat                                                              10

SEQ ID NO: 225          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 225
gatcgtcggg                                                              10

SEQ ID NO: 226          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 226
tcttgttttg                                                              10

SEQ ID NO: 227          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 227
aatattgctc                                                              10

SEQ ID NO: 228          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 228
aacgtcgtct                                                              10

SEQ ID NO: 229          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 229
aatattttg                                                               10

SEQ ID NO: 230          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

```
                         organism = synthetic construct
SEQUENCE: 230
cgtaacgtgc                                                               10

SEQ ID NO: 231           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 231
gcgtggttat                                                               10

SEQ ID NO: 232           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 232
caaaacatta                                                               10

SEQ ID NO: 233           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 233
cgtatcctga                                                               10

SEQ ID NO: 234           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 234
tcgcttacaa                                                               10

SEQ ID NO: 235           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 235
tccattgtgt                                                               10

SEQ ID NO: 236           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 236
gcccccattc                                                               10

SEQ ID NO: 237           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 237
```

```
tgacgtctat                                                              10

SEQ ID NO: 238          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 238
tgggccgagg                                                              10

SEQ ID NO: 239          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 239
aagtgtcaag                                                              10

SEQ ID NO: 240          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 240
gacagtagag                                                              10

SEQ ID NO: 241          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 241
cgcagccatc                                                              10

SEQ ID NO: 242          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 242
gaggcagaac                                                              10

SEQ ID NO: 243          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 243
gttgaaattg                                                              10

SEQ ID NO: 244          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 244
atctgataaa                                                              10
```

-continued

```
SEQ ID NO: 245          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 245
agctgtctct                                                            10

SEQ ID NO: 246          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 246
ttttaggtta                                                            10

SEQ ID NO: 247          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 247
tatctgtccg                                                            10

SEQ ID NO: 248          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 248
aaaacatatg                                                            10

SEQ ID NO: 249          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 249
gtaaagaaga                                                            10

SEQ ID NO: 250          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 250
tcgacgtgca                                                            10

SEQ ID NO: 251          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 251
tagatcttaa                                                            10

SEQ ID NO: 252          moltype = DNA  length = 10
FEATURE                 Location/Qualifiers
```

-continued

```
misc_feature            1..10
                        note = Description of Artificial Sequence: Synthetic
                         oligonucleotide
source                  1..10
                        mol_type = other DNA
                        organism = synthetic construct
SEQUENCE: 252
cactggtcac                                                                10

SEQ ID NO: 253          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 253
attctgatgt                                                                10

SEQ ID NO: 254          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 254
atggccctga                                                                10

SEQ ID NO: 255          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 255
ggtgatgaga                                                                10

SEQ ID NO: 256          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 256
caccgtgggg                                                                10

SEQ ID NO: 257          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 257
gcttgctcgg                                                                10

SEQ ID NO: 258          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 258
ccagttgaac                                                                10

SEQ ID NO: 259          moltype = DNA  length = 10
FEATURE                 Location/Qualifiers
misc_feature            1..10
                        note = Description of Artificial Sequence: Synthetic
```

```
                       oligonucleotide
source                 1..10
                       mol_type = other DNA
                       organism = synthetic construct
SEQUENCE: 259
cgtctgtacc                                                            10

SEQ ID NO: 260         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 260
ccaacgcggc                                                            10

SEQ ID NO: 261         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 261
acgtgatcga                                                            10

SEQ ID NO: 262         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 262
ccatcgaatc                                                            10

SEQ ID NO: 263         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 263
cggtgtctgc                                                            10

SEQ ID NO: 264         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 264
aaaccacctc                                                            10

SEQ ID NO: 265         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 265
tcaatgttcc                                                            10

SEQ ID NO: 266         moltype = DNA  length = 10
FEATURE                Location/Qualifiers
misc_feature           1..10
                       note = Description of Artificial Sequence: Synthetic
                        oligonucleotide
source                 1..10
```

```
                        mol_type = other DNA
                        organism = synthetic construct
SEQUENCE: 266
ttcgacatgt                                                        10

SEQ ID NO: 267          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 267
aggcacgata                                                        10

SEQ ID NO: 268          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 268
cacgagatca                                                        10

SEQ ID NO: 269          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 269
catgctgggg                                                        10

SEQ ID NO: 270          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 270
taccatggtt                                                        10

SEQ ID NO: 271          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 271
ttgcccatat                                                        10

SEQ ID NO: 272          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 272
tgcacattcg                                                        10

SEQ ID NO: 273          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
```

```
SEQUENCE: 273
gttatgttgg                                                    10

SEQ ID NO: 274          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 274
tgagttatga                                                    10

SEQ ID NO: 275          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 275
gatggccccc                                                    10

SEQ ID NO: 276          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 276
gatgggttac                                                    10

SEQ ID NO: 277          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 277
agctacgttg                                                    10

SEQ ID NO: 278          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 278
accccatgca                                                    10

SEQ ID NO: 279          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 279
tactaccgtt                                                    10

SEQ ID NO: 280          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 280
tcgcttctac                                                    10
```

```
SEQ ID NO: 281          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 281
ctggcagtgc                                                            10

SEQ ID NO: 282          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 282
tctatatata                                                            10

SEQ ID NO: 283          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 283
ggattagttc                                                            10

SEQ ID NO: 284          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 284
gtgttacgct                                                            10

SEQ ID NO: 285          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 285
tcgactccgt                                                            10

SEQ ID NO: 286          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 286
ggtagcaggc                                                            10

SEQ ID NO: 287          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 287
tattggattc                                                            10

SEQ ID NO: 288          moltype = DNA  length = 10
```

-continued

```
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 288
gttcgatcga                                                               10

SEQ ID NO: 289          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 289
atattaatat                                                               10

SEQ ID NO: 290          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 290
agaacgattg                                                               10

SEQ ID NO: 291          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 291
gtaaagtgta                                                               10

SEQ ID NO: 292          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 292
cccatgtgcc                                                               10

SEQ ID NO: 293          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 293
gtggcctcgc                                                               10

SEQ ID NO: 294          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 294
gacactagga                                                               10

SEQ ID NO: 295          moltype = DNA  length = 10
FEATURE                 Location/Qualifiers
misc_feature            1..10
```

```
                        note = Description of Artificial Sequence: Synthetic
                         oligonucleotide
source                  1..10
                        mol_type = other DNA
                        organism = synthetic construct
SEQUENCE: 295
atattctgac                                                                 10

SEQ ID NO: 296          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 296
taagtagacg                                                                 10

SEQ ID NO: 297          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 297
taacggtcta                                                                 10

SEQ ID NO: 298          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 298
tagtttcatt                                                                 10

SEQ ID NO: 299          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 299
ttggatccga                                                                 10

SEQ ID NO: 300          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 300
cgtgacaacc                                                                 10

SEQ ID NO: 301          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 301
cgcgctcaga                                                                 10

SEQ ID NO: 302          moltype = DNA  length = 10
FEATURE                 Location/Qualifiers
misc_feature            1..10
                        note = Description of Artificial Sequence: Synthetic
                         oligonucleotide
```

```
source                  1..10
                        mol_type = other DNA
                        organism = synthetic construct
SEQUENCE: 302
cgttcttaat                                                                10

SEQ ID NO: 303          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 303
acaagagttt                                                                10

SEQ ID NO: 304          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 304
agggttatag                                                                10

SEQ ID NO: 305          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 305
accacgactc                                                                10

SEQ ID NO: 306          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 306
gtactcgggg                                                                10

SEQ ID NO: 307          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 307
acaaatatct                                                                10

SEQ ID NO: 308          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 308
gatcggggtg                                                                10

SEQ ID NO: 309          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

```
                         organism = synthetic construct
SEQUENCE: 309
atgtaactcc                                                                10

SEQ ID NO: 310           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 310
atgaagaagc                                                                10

SEQ ID NO: 311           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 311
atgtattgtc                                                                10

SEQ ID NO: 312           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 312
tgcattggaa                                                                10

SEQ ID NO: 313           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 313
gcggacgatc                                                                10

SEQ ID NO: 314           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 314
ccgtacttga                                                                10

SEQ ID NO: 315           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 315
tttgcccccg                                                                10

SEQ ID NO: 316           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 316
```

-continued

```
acctcacgcg                                                            10

SEQ ID NO: 317          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 317
attaaggggc                                                            10

SEQ ID NO: 318          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 318
cgtggacatg                                                            10

SEQ ID NO: 319          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 319
ttagcccttc                                                            10

SEQ ID NO: 320          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 320
cgagagtttg                                                            10

SEQ ID NO: 321          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 321
tgcatcctct                                                            10

SEQ ID NO: 322          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 322
tgcgattccg                                                            10

SEQ ID NO: 323          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 323
ttattacgtt                                                            10
```

```
SEQ ID NO: 324          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 324
tgatgtggtt                                                          10

SEQ ID NO: 325          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 325
gggcgtcaat                                                          10

SEQ ID NO: 326          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 326
cccttgaaat                                                          10

SEQ ID NO: 327          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 327
tctttggggc                                                          10

SEQ ID NO: 328          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 328
accggcaggc                                                          10

SEQ ID NO: 329          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 329
gctaaaatct                                                          10

SEQ ID NO: 330          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 330
gccgttgacg                                                          10

SEQ ID NO: 331          moltype = DNA  length = 10
FEATURE                 Location/Qualifiers
```

```
misc_feature          1..10
                      note = Description of Artificial Sequence: Synthetic
                       oligonucleotide
source                1..10
                      mol_type = other DNA
                      organism = synthetic construct
SEQUENCE: 331
ggagttgttg                                                     10

SEQ ID NO: 332        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 332
tacttgagaa                                                     10

SEQ ID NO: 333        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 333
cgggtgcgct                                                     10

SEQ ID NO: 334        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 334
aaaagcgtct                                                     10

SEQ ID NO: 335        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 335
gtaaagatag                                                     10

SEQ ID NO: 336        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 336
gcctggtcag                                                     10

SEQ ID NO: 337        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 337
ggcaaaaagg                                                     10

SEQ ID NO: 338        moltype = DNA  length = 10
FEATURE               Location/Qualifiers
misc_feature          1..10
                      note = Description of Artificial Sequence: Synthetic
```

```
                        oligonucleotide
source                  1..10
                        mol_type = other DNA
                        organism = synthetic construct
SEQUENCE: 338
acccttctct                                                              10

SEQ ID NO: 339          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 339
tcacatagtg                                                              10

SEQ ID NO: 340          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 340
tcgtctgtgc                                                              10

SEQ ID NO: 341          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 341
tgctcggatc                                                              10

SEQ ID NO: 342          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 342
agcagtcccg                                                              10

SEQ ID NO: 343          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 343
tttgggctgt                                                              10

SEQ ID NO: 344          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 344
ctcacgatct                                                              10

SEQ ID NO: 345          moltype = DNA  length = 10
FEATURE                 Location/Qualifiers
misc_feature            1..10
                        note = Description of Artificial Sequence: Synthetic
                         oligonucleotide
source                  1..10
```

-continued

```
                        mol_type = other DNA
                        organism = synthetic construct
SEQUENCE: 345
tggcgcatac                                                            10

SEQ ID NO: 346          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 346
gcaattgaaa                                                            10

SEQ ID NO: 347          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 347
tcgggagacg                                                            10

SEQ ID NO: 348          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 348
cccggcgaaa                                                            10

SEQ ID NO: 349          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 349
tgatgcggaa                                                            10

SEQ ID NO: 350          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 350
aactgaggcg                                                            10

SEQ ID NO: 351          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 351
catattattt                                                            10

SEQ ID NO: 352          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
```

```
SEQUENCE: 352
aaaagtcatt                                                            10

SEQ ID NO: 353         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 353
aagcggtgag                                                            10

SEQ ID NO: 354         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 354
aaggtaatca                                                            10

SEQ ID NO: 355         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 355
ctgacactta                                                            10

SEQ ID NO: 356         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 356
ctgttttcta                                                            10

SEQ ID NO: 357         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 357
cacatggcag                                                            10

SEQ ID NO: 358         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 358
ttcaatccgg                                                            10

SEQ ID NO: 359         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 359
tgtccggcat                                                            10
```

```
SEQ ID NO: 360          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 360
tggtaccgtg                                                            10

SEQ ID NO: 361          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 361
aagagatatt                                                            10

SEQ ID NO: 362          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 362
gatgtactac                                                            10

SEQ ID NO: 363          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 363
gaaatggaat                                                            10

SEQ ID NO: 364          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 364
ttaaaatact                                                            10

SEQ ID NO: 365          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 365
tgaccggaac                                                            10

SEQ ID NO: 366          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 366
gtcgccgcaa                                                            10

SEQ ID NO: 367          moltype = DNA  length = 10
```

-continued

```
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 367
taggataccg                                                            10

SEQ ID NO: 368          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 368
agtccaattg                                                            10

SEQ ID NO: 369          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 369
gggggctata                                                            10

SEQ ID NO: 370          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 370
accttcagtt                                                            10

SEQ ID NO: 371          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 371
atggcaagta                                                            10

SEQ ID NO: 372          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 372
agaatgtttt                                                            10

SEQ ID NO: 373          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 373
agttcgtttg                                                            10

SEQ ID NO: 374          moltype = DNA  length = 10
FEATURE                 Location/Qualifiers
misc_feature            1..10
```

```
                        note = Description of Artificial Sequence: Synthetic
                         oligonucleotide
source                  1..10
                        mol_type = other DNA
                        organism = synthetic construct
SEQUENCE: 374
cactactgac                                                                10

SEQ ID NO: 375          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 375
gatcaagagc                                                                10

SEQ ID NO: 376          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 376
atttatcgag                                                                10

SEQ ID NO: 377          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 377
ccttttttcca                                                                10

SEQ ID NO: 378          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 378
gcacagaggt                                                                10

SEQ ID NO: 379          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 379
tgatctgaat                                                                10

SEQ ID NO: 380          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 380
gttggaggga                                                                10

SEQ ID NO: 381          moltype = DNA  length = 10
FEATURE                 Location/Qualifiers
misc_feature            1..10
                        note = Description of Artificial Sequence: Synthetic
                         oligonucleotide
```

-continued

```
source                1..10
                      mol_type = other DNA
                      organism = synthetic construct
SEQUENCE: 381
ttttgaaggt                                                            10

SEQ ID NO: 382        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 382
taagtcctaa                                                            10

SEQ ID NO: 383        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 383
ggtgttaggg                                                            10

SEQ ID NO: 384        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 384
tgtatgcacc                                                            10

SEQ ID NO: 385        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 385
ccgtgccatt                                                            10

SEQ ID NO: 386        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 386
gaaatcaccc                                                            10

SEQ ID NO: 387        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 387
tttgcacgtg                                                            10

SEQ ID NO: 388        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
```

```
                        organism = synthetic construct
SEQUENCE: 388
cgtctgtttt                                                          10

SEQ ID NO: 389          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 389
ctacaccaca                                                          10

SEQ ID NO: 390          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 390
tgctacaggg                                                          10

SEQ ID NO: 391          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 391
gggaatatat                                                          10

SEQ ID NO: 392          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 392
tcatgtattt                                                          10

SEQ ID NO: 393          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 393
tctccgttta                                                          10

SEQ ID NO: 394          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 394
tacctctcgc                                                          10

SEQ ID NO: 395          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 395
```

```
gcttcaaccg                                                          10

SEQ ID NO: 396          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 396
atgaagctac                                                          10

SEQ ID NO: 397          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 397
cggtacaact                                                          10

SEQ ID NO: 398          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 398
gtgtggtcgt                                                          10

SEQ ID NO: 399          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 399
ggggtcatgt                                                          10

SEQ ID NO: 400          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 400
aggcagccca                                                          10

SEQ ID NO: 401          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 401
caagcacgat                                                          10

SEQ ID NO: 402          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 402
tcaaatggat                                                          10
```

-continued

```
SEQ ID NO: 403          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 403
ggactgaata                                                             10

SEQ ID NO: 404          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 404
ccgtagacgt                                                             10

SEQ ID NO: 405          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 405
cggcgtaccg                                                             10

SEQ ID NO: 406          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 406
ggcggcgccc                                                             10

SEQ ID NO: 407          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 407
agacttgatc                                                             10

SEQ ID NO: 408          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 408
accttgcaca                                                             10

SEQ ID NO: 409          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 409
taaggtgagt                                                             10

SEQ ID NO: 410          moltype = DNA  length = 10
FEATURE                 Location/Qualifiers
```

```
misc_feature            1..10
                        note = Description of Artificial Sequence: Synthetic
                         oligonucleotide
source                  1..10
                        mol_type = other DNA
                        organism = synthetic construct
SEQUENCE: 410
ttgttgtttc                                                                   10

SEQ ID NO: 411          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 411
gagggaatac                                                                   10

SEQ ID NO: 412          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 412
ctcgtacgcg                                                                   10

SEQ ID NO: 413          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 413
ccgcggttta                                                                   10

SEQ ID NO: 414          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 414
ttaaagttaa                                                                   10

SEQ ID NO: 415          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 415
gcatatgggt                                                                   10

SEQ ID NO: 416          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 416
agtctgagcc                                                                   10

SEQ ID NO: 417          moltype = DNA  length = 10
FEATURE                 Location/Qualifiers
misc_feature            1..10
                        note = Description of Artificial Sequence: Synthetic
```

```
                         oligonucleotide
source                  1..10
                        mol_type = other DNA
                        organism = synthetic construct
SEQUENCE: 417
tgtcggttcg                                                            10

SEQ ID NO: 418          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 418
ggtctcaacc                                                            10

SEQ ID NO: 419          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 419
gtaacggcat                                                            10

SEQ ID NO: 420          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 420
acactgagaa                                                            10

SEQ ID NO: 421          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 421
cccaacgtcg                                                            10

SEQ ID NO: 422          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 422
aagaaactgc                                                            10

SEQ ID NO: 423          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 423
accagcccac                                                            10

SEQ ID NO: 424          moltype = DNA  length = 10
FEATURE                 Location/Qualifiers
misc_feature            1..10
                        note = Description of Artificial Sequence: Synthetic
                         oligonucleotide
source                  1..10
```

```
                          mol_type = other DNA
                          organism = synthetic construct
SEQUENCE: 424
tgtagttact                                                              10

SEQ ID NO: 425            moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 425
ggctagaggc                                                              10

SEQ ID NO: 426            moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 426
gttcggcaga                                                              10

SEQ ID NO: 427            moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 427
ccaaaataga                                                              10

SEQ ID NO: 428            moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 428
cccatataac                                                              10

SEQ ID NO: 429            moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 429
gtcactaccg                                                              10

SEQ ID NO: 430            moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
SEQUENCE: 430
gtagtgtggc                                                              10

SEQ ID NO: 431            moltype = DNA  length = 10
FEATURE                   Location/Qualifiers
misc_feature              1..10
                          note = Description of Artificial Sequence: Synthetic
                           oligonucleotide
source                    1..10
                          mol_type = other DNA
                          organism = synthetic construct
```

```
SEQUENCE: 431
caatctcata                                                            10

SEQ ID NO: 432          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 432
ccatgttata                                                            10

SEQ ID NO: 433          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 433
taagcagtgg                                                            10

SEQ ID NO: 434          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 434
tcggcggcta                                                            10

SEQ ID NO: 435          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 435
tattaaatgc                                                            10

SEQ ID NO: 436          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 436
gtcgccatta                                                            10

SEQ ID NO: 437          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 437
ggcgtcgttc                                                            10

SEQ ID NO: 438          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 438
ctagtagata                                                            10
```

```
SEQ ID NO: 439          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 439
tcgtcagtat                                                            10

SEQ ID NO: 440          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 440
ggggtatcgg                                                            10

SEQ ID NO: 441          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 441
tgctctgcca                                                            10

SEQ ID NO: 442          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 442
tgccgtaact                                                            10

SEQ ID NO: 443          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 443
cggtacaggc                                                            10

SEQ ID NO: 444          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 444
tcctaatttg                                                            10

SEQ ID NO: 445          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 445
tctttctgga                                                            10

SEQ ID NO: 446          moltype = DNA  length = 10
```

```
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 446
ccgcgacttg                                                  10

SEQ ID NO: 447         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 447
acctatagcg                                                  10

SEQ ID NO: 448         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 448
gccggcacct                                                  10

SEQ ID NO: 449         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 449
tttgataggc                                                  10

SEQ ID NO: 450         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 450
actgtgagct                                                  10

SEQ ID NO: 451         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 451
ttatcgttca                                                  10

SEQ ID NO: 452         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 452
actagtggcc                                                  10

SEQ ID NO: 453         moltype = DNA  length = 10
FEATURE                Location/Qualifiers
misc_feature           1..10
```

```
                        note = Description of Artificial Sequence: Synthetic
                         oligonucleotide
source                  1..10
                        mol_type = other DNA
                        organism = synthetic construct
SEQUENCE: 453
cctccgtggt                                                   10

SEQ ID NO: 454          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 454
ttagggtatg                                                   10

SEQ ID NO: 455          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 455
gaatcaggcg                                                   10

SEQ ID NO: 456          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 456
ggctgaccaa                                                   10

SEQ ID NO: 457          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 457
tgccagaccg                                                   10

SEQ ID NO: 458          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 458
tccctacgcg                                                   10

SEQ ID NO: 459          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 459
tccgctggag                                                   10

SEQ ID NO: 460          moltype = DNA  length = 10
FEATURE                 Location/Qualifiers
misc_feature            1..10
                        note = Description of Artificial Sequence: Synthetic
                         oligonucleotide
```

```
source                  1..10
                        mol_type = other DNA
                        organism = synthetic construct
SEQUENCE: 460
ggatcaaaac                                                           10

SEQ ID NO: 461          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 461
ttcacctcac                                                           10

SEQ ID NO: 462          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 462
gacacacggc                                                           10

SEQ ID NO: 463          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 463
tgggcgatta                                                           10

SEQ ID NO: 464          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 464
taagatcttc                                                           10

SEQ ID NO: 465          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 465
ctccgactac                                                           10

SEQ ID NO: 466          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 466
gggccatcat                                                           10

SEQ ID NO: 467          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

```
                        organism = synthetic construct
SEQUENCE: 467
tcaggccaga                                                            10

SEQ ID NO: 468          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 468
cttgtggggc                                                            10

SEQ ID NO: 469          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 469
agatagtctg                                                            10

SEQ ID NO: 470          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 470
gcgtcaaagt                                                            10

SEQ ID NO: 471          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 471
acgaaaattt                                                            10

SEQ ID NO: 472          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 472
gagtctggtg                                                            10

SEQ ID NO: 473          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 473
atcgagcgac                                                            10

SEQ ID NO: 474          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 474
```

-continued

```
ggtcctcaga                                                              10

SEQ ID NO: 475          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 475
tgattttgtc                                                              10

SEQ ID NO: 476          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 476
gcatttctca                                                              10

SEQ ID NO: 477          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 477
gcatgccagt                                                              10

SEQ ID NO: 478          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 478
attagacgac                                                              10

SEQ ID NO: 479          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 479
aaagcccata                                                              10

SEQ ID NO: 480          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 480
cactacattc                                                              10

SEQ ID NO: 481          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 481
cacggtttct                                                              10
```

```
SEQ ID NO: 482          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 482
cccaccagtg                                                          10

SEQ ID NO: 483          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 483
ctcacttgtc                                                          10

SEQ ID NO: 484          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 484
gatagactct                                                          10

SEQ ID NO: 485          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 485
atttccattt                                                          10

SEQ ID NO: 486          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 486
atatgtggcc                                                          10

SEQ ID NO: 487          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 487
cgggacgaac                                                          10

SEQ ID NO: 488          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 488
agaaccgtga                                                          10

SEQ ID NO: 489          moltype = DNA  length = 10
FEATURE                 Location/Qualifiers
```

```
misc_feature            1..10
                        note = Description of Artificial Sequence: Synthetic
                         oligonucleotide
source                  1..10
                        mol_type = other DNA
                        organism = synthetic construct
SEQUENCE: 489
tagtgtactg                                                                  10

SEQ ID NO: 490          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 490
aactaatcga                                                                  10

SEQ ID NO: 491          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 491
cgaagtgacg                                                                  10

SEQ ID NO: 492          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 492
cggagcctcg                                                                  10

SEQ ID NO: 493          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 493
atcacacgag                                                                  10

SEQ ID NO: 494          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 494
cgacgagttc                                                                  10

SEQ ID NO: 495          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 495
gcttcccgtg                                                                  10

SEQ ID NO: 496          moltype = DNA  length = 10
FEATURE                 Location/Qualifiers
misc_feature            1..10
                        note = Description of Artificial Sequence: Synthetic
```

```
                        oligonucleotide
source                  1..10
                        mol_type = other DNA
                        organism = synthetic construct
SEQUENCE: 496
gattcatacc                                                                10

SEQ ID NO: 497          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 497
gagagaagcg                                                                10

SEQ ID NO: 498          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 498
gaagtggcct                                                                10

SEQ ID NO: 499          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 499
ggacgacgcc                                                                10

SEQ ID NO: 500          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 500
tagggtctca                                                                10

SEQ ID NO: 501          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 501
aactacaggt                                                                10

SEQ ID NO: 502          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 502
gtggcctgtg                                                                10

SEQ ID NO: 503          moltype = DNA  length = 10
FEATURE                 Location/Qualifiers
misc_feature            1..10
                        note = Description of Artificial Sequence: Synthetic
                         oligonucleotide
source                  1..10
```

```
                        mol_type = other DNA
                        organism = synthetic construct
SEQUENCE: 503
ctttaccagc                                                      10

SEQ ID NO: 504          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 504
cgcgttactg                                                      10

SEQ ID NO: 505          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 505
ttgctcccgt                                                      10

SEQ ID NO: 506          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 506
catcaaacaa                                                      10

SEQ ID NO: 507          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 507
gctttatgat                                                      10

SEQ ID NO: 508          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 508
ctgcatactg                                                      10

SEQ ID NO: 509          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 509
ggtggctcag                                                      10

SEQ ID NO: 510          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
```

```
SEQUENCE: 510
ggacgatcaa                                                          10

SEQ ID NO: 511          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 511
ccgactggtg                                                          10

SEQ ID NO: 512          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 512
ggaacaaccg                                                          10

SEQ ID NO: 513          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 513
gaacgagacc                                                          10

SEQ ID NO: 514          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 514
caccaagaaa                                                          10

SEQ ID NO: 515          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 515
atgcattacc                                                          10

SEQ ID NO: 516          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 516
gtatcatgcc                                                          10

SEQ ID NO: 517          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 517
agtagatgtt                                                          10
```

```
SEQ ID NO: 518          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 518
ctctagatgt                                                    10

SEQ ID NO: 519          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 519
gctacttgtg                                                    10

SEQ ID NO: 520          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 520
tatgaaacgt                                                    10

SEQ ID NO: 521          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 521
cctcgttgat                                                    10

SEQ ID NO: 522          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 522
ctagagccat                                                    10

SEQ ID NO: 523          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 523
tagagttata                                                    10

SEQ ID NO: 524          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 524
aacgagaggc                                                    10

SEQ ID NO: 525          moltype = DNA  length = 10
```

```
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 525
ggtctaccgt                                                            10

SEQ ID NO: 526         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 526
gccccctcac                                                            10

SEQ ID NO: 527         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 527
cataggaatt                                                            10

SEQ ID NO: 528         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 528
tccggctcgt                                                            10

SEQ ID NO: 529         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 529
tgagagtcgg                                                            10

SEQ ID NO: 530         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 530
cgtagaaata                                                            10

SEQ ID NO: 531         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 531
ctttacatga                                                            10

SEQ ID NO: 532         moltype = DNA  length = 10
FEATURE                Location/Qualifiers
misc_feature           1..10
```

```
                        note = Description of Artificial Sequence: Synthetic
                         oligonucleotide
source                  1..10
                        mol_type = other DNA
                        organism = synthetic construct
SEQUENCE: 532
gagcgccgtc                                                   10

SEQ ID NO: 533          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 533
ggctctcggc                                                   10

SEQ ID NO: 534          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 534
agagcttgtt                                                   10

SEQ ID NO: 535          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 535
aatcagccac                                                   10

SEQ ID NO: 536          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 536
agaagagcca                                                   10

SEQ ID NO: 537          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 537
tcgtatgagt                                                   10

SEQ ID NO: 538          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 538
ttcttcctcg                                                   10

SEQ ID NO: 539          moltype = DNA  length = 10
FEATURE                 Location/Qualifiers
misc_feature            1..10
                        note = Description of Artificial Sequence: Synthetic
                         oligonucleotide
```

```
source                  1..10
                        mol_type = other DNA
                        organism = synthetic construct
SEQUENCE: 539
acacaaaagc                                                          10

SEQ ID NO: 540          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 540
cgcgggaccc                                                          10

SEQ ID NO: 541          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 541
gtcgcgacac                                                          10

SEQ ID NO: 542          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 542
ccggaggaaa                                                          10

SEQ ID NO: 543          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 543
cggcgtatga                                                          10

SEQ ID NO: 544          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 544
taggcattct                                                          10

SEQ ID NO: 545          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 545
aaaggaggga                                                          10

SEQ ID NO: 546          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

```
                        organism = synthetic construct
SEQUENCE: 546
acctttacgg                                                                10

SEQ ID NO: 547          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 547
ctaccgttaa                                                                10

SEQ ID NO: 548          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 548
gagcttcgcc                                                                10

SEQ ID NO: 549          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 549
gccatagaag                                                                10

SEQ ID NO: 550          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 550
tttagcgtat                                                                10

SEQ ID NO: 551          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 551
gcaaacagat                                                                10

SEQ ID NO: 552          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 552
taggtcatgg                                                                10

SEQ ID NO: 553          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 553
```

-continued

```
ctctaacaga                                                         10

SEQ ID NO: 554          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 554
ggctcatgaa                                                         10

SEQ ID NO: 555          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 555
caatgtctca                                                         10

SEQ ID NO: 556          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 556
tgatcgtatt                                                         10

SEQ ID NO: 557          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 557
gcgcttttca                                                         10

SEQ ID NO: 558          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 558
aagattatat                                                         10

SEQ ID NO: 559          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 559
actagctgac                                                         10

SEQ ID NO: 560          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 560
ggtgagctca                                                         10
```

```
SEQ ID NO: 561          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 561
cgctttcgct                                                            10

SEQ ID NO: 562          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 562
tgattcaaaa                                                            10

SEQ ID NO: 563          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 563
actgaacagg                                                            10

SEQ ID NO: 564          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 564
attcgagcta                                                            10

SEQ ID NO: 565          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 565
tgtaggctaa                                                            10

SEQ ID NO: 566          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 566
acaaagcttt                                                            10

SEQ ID NO: 567          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 567
gcccgaggga                                                            10

SEQ ID NO: 568          moltype = DNA  length = 10
FEATURE                 Location/Qualifiers
```

-continued

```
misc_feature          1..10
                      note = Description of Artificial Sequence: Synthetic
                       oligonucleotide
source                1..10
                      mol_type = other DNA
                      organism = synthetic construct
SEQUENCE: 568
gcccgctggg                                                              10

SEQ ID NO: 569        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 569
accccgctga                                                              10

SEQ ID NO: 570        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 570
cttatgccct                                                              10

SEQ ID NO: 571        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 571
ccgccatagc                                                              10

SEQ ID NO: 572        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 572
cttaatgatt                                                              10

SEQ ID NO: 573        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 573
cagtccacaa                                                              10

SEQ ID NO: 574        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 574
atggacggac                                                              10

SEQ ID NO: 575        moltype = DNA  length = 10
FEATURE               Location/Qualifiers
misc_feature          1..10
                      note = Description of Artificial Sequence: Synthetic
```

```
                         oligonucleotide
source                  1..10
                        mol_type = other DNA
                        organism = synthetic construct
SEQUENCE: 575
cggcctctcg                                                  10

SEQ ID NO: 576          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 576
tagtcgccat                                                  10

SEQ ID NO: 577          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 577
gttgatcttc                                                  10

SEQ ID NO: 578          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 578
acttgccaag                                                  10

SEQ ID NO: 579          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 579
atgactggtt                                                  10

SEQ ID NO: 580          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 580
tgtcgtagga                                                  10

SEQ ID NO: 581          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 581
agcaaacacg                                                  10

SEQ ID NO: 582          moltype = DNA  length = 10
FEATURE                 Location/Qualifiers
misc_feature            1..10
                        note = Description of Artificial Sequence: Synthetic
                         oligonucleotide
source                  1..10
```

```
                         mol_type = other DNA
                         organism = synthetic construct
SEQUENCE: 582
tactgatgaa                                                            10

SEQ ID NO: 583           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 583
gtatcccata                                                            10

SEQ ID NO: 584           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 584
tagccaggtt                                                            10

SEQ ID NO: 585           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 585
cgtgtggcga                                                            10

SEQ ID NO: 586           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 586
atcgaattgc                                                            10

SEQ ID NO: 587           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 587
ccccaatatt                                                            10

SEQ ID NO: 588           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 588
cccgtttctc                                                            10

SEQ ID NO: 589           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
```

```
SEQUENCE: 589
tccgcatcta                                                        10

SEQ ID NO: 590          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 590
caagcctcat                                                        10

SEQ ID NO: 591          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 591
tttcaatccc                                                        10

SEQ ID NO: 592          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 592
ccttcccatc                                                        10

SEQ ID NO: 593          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 593
aggtacaaga                                                        10

SEQ ID NO: 594          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 594
gtgtaatgga                                                        10

SEQ ID NO: 595          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 595
aaactgagct                                                        10

SEQ ID NO: 596          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 596
atctctgccc                                                        10
```

```
SEQ ID NO: 597          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 597
cgacatttgc                                                                   10

SEQ ID NO: 598          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 598
tgtgaacccg                                                                   10

SEQ ID NO: 599          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 599
tgacacccca                                                                   10

SEQ ID NO: 600          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 600
taggccaaag                                                                   10

SEQ ID NO: 601          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 601
gaaattgtag                                                                   10

SEQ ID NO: 602          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 602
gcgtctgatt                                                                   10

SEQ ID NO: 603          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 603
tctcattgtt                                                                   10

SEQ ID NO: 604          moltype = DNA  length = 10
```

```
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 604
ctgacatctc                                                                10

SEQ ID NO: 605          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 605
gtatccagtg                                                                10

SEQ ID NO: 606          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 606
gatggccgtt                                                                10

SEQ ID NO: 607          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 607
tcaccctctc                                                                10

SEQ ID NO: 608          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 608
ggcactattc                                                                10

SEQ ID NO: 609          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 609
aaataactgt                                                                10

SEQ ID NO: 610          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 610
cagctccatt                                                                10

SEQ ID NO: 611          moltype = DNA  length = 10
FEATURE                 Location/Qualifiers
misc_feature            1..10
```

```
                        note = Description of Artificial Sequence: Synthetic
                         oligonucleotide
source                  1..10
                        mol_type = other DNA
                        organism = synthetic construct
SEQUENCE: 611
ctcttgactc                                                                  10

SEQ ID NO: 612          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 612
tttcctatac                                                                  10

SEQ ID NO: 613          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 613
ccatacccga                                                                  10

SEQ ID NO: 614          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 614
tcgccgagcg                                                                  10

SEQ ID NO: 615          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 615
cgctgaagcc                                                                  10

SEQ ID NO: 616          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 616
tctggcccca                                                                  10

SEQ ID NO: 617          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 617
gctacattga                                                                  10

SEQ ID NO: 618          moltype = DNA  length = 10
FEATURE                 Location/Qualifiers
misc_feature            1..10
                        note = Description of Artificial Sequence: Synthetic
                         oligonucleotide
```

```
source                  1..10
                        mol_type = other DNA
                        organism = synthetic construct
SEQUENCE: 618
cgcatcataa                                                   10

SEQ ID NO: 619          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 619
gcaaagggcc                                                   10

SEQ ID NO: 620          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 620
aacggcgcag                                                   10

SEQ ID NO: 621          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 621
cgactgacat                                                   10

SEQ ID NO: 622          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 622
atgacagggc                                                   10

SEQ ID NO: 623          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 623
caagttctcc                                                   10

SEQ ID NO: 624          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 624
tcgccgcttt                                                   10

SEQ ID NO: 625          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

```
                        organism = synthetic construct
SEQUENCE: 625
atgccggaaa                                                          10

SEQ ID NO: 626          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 626
gcggttacta                                                          10

SEQ ID NO: 627          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 627
gacattacaa                                                          10

SEQ ID NO: 628          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 628
cagagagggc                                                          10

SEQ ID NO: 629          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 629
gcaccgcctc                                                          10

SEQ ID NO: 630          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 630
cggtccgagc                                                          10

SEQ ID NO: 631          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 631
tgtccggtgc                                                          10

SEQ ID NO: 632          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 632
```

```
ggtcggttgc                                                        10

SEQ ID NO: 633          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 633
gctcagctaa                                                        10

SEQ ID NO: 634          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 634
agcagttcgt                                                        10

SEQ ID NO: 635          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 635
aaatcgatga                                                        10

SEQ ID NO: 636          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 636
gctcggtatg                                                        10

SEQ ID NO: 637          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 637
cccgccgcgg                                                        10

SEQ ID NO: 638          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 638
gtgtgatagg                                                        10

SEQ ID NO: 639          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 639
ttggactcca                                                        10
```

```
SEQ ID NO: 640          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 640
tgcttatcta                                                    10

SEQ ID NO: 641          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 641
caaaaggcgt                                                    10

SEQ ID NO: 642          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 642
tagggggcct                                                    10

SEQ ID NO: 643          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 643
aagtattaat                                                    10

SEQ ID NO: 644          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 644
gtttagcccg                                                    10

SEQ ID NO: 645          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 645
cgctaatatg                                                    10

SEQ ID NO: 646          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 646
acaacacgtt                                                    10

SEQ ID NO: 647          moltype = DNA  length = 10
FEATURE                 Location/Qualifiers
```

```
misc_feature            1..10
                        note = Description of Artificial Sequence: Synthetic
                         oligonucleotide
source                  1..10
                        mol_type = other DNA
                        organism = synthetic construct
SEQUENCE: 647
agagatgctc                                                                  10

SEQ ID NO: 648          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 648
tgcctgatat                                                                  10

SEQ ID NO: 649          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 649
cttgtaagta                                                                  10

SEQ ID NO: 650          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 650
catattgccg                                                                  10

SEQ ID NO: 651          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 651
cttagaaagt                                                                  10

SEQ ID NO: 652          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 652
atgttgtatt                                                                  10

SEQ ID NO: 653          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 653
cgcattgaag                                                                  10

SEQ ID NO: 654          moltype = DNA  length = 10
FEATURE                 Location/Qualifiers
misc_feature            1..10
                        note = Description of Artificial Sequence: Synthetic
```

```
                         oligonucleotide
source                   1..10
                         mol_type = other DNA
                         organism = synthetic construct
SEQUENCE: 654
ttatgttggt                                                    10

SEQ ID NO: 655           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 655
tcgcctcaga                                                    10

SEQ ID NO: 656           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 656
ttcgttgagg                                                    10

SEQ ID NO: 657           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 657
ggtgccgggc                                                    10

SEQ ID NO: 658           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 658
accattgtaa                                                    10

SEQ ID NO: 659           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 659
ttgattgtca                                                    10

SEQ ID NO: 660           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 660
cggctcacct                                                    10

SEQ ID NO: 661           moltype = DNA  length = 10
FEATURE                  Location/Qualifiers
misc_feature             1..10
                         note = Description of Artificial Sequence: Synthetic
                          oligonucleotide
source                   1..10
```

```
                        mol_type = other DNA
                        organism = synthetic construct
SEQUENCE: 661
ctatcacatg                                                        10

SEQ ID NO: 662          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 662
gtagacagaa                                                        10

SEQ ID NO: 663          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 663
cctttaccaa                                                        10

SEQ ID NO: 664          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 664
gcacatcgac                                                        10

SEQ ID NO: 665          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 665
tctcactttc                                                        10

SEQ ID NO: 666          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 666
ttcgagtact                                                        10

SEQ ID NO: 667          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 667
tagaagagca                                                        10

SEQ ID NO: 668          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
```

```
SEQUENCE: 668
aaccccacca                                                              10

SEQ ID NO: 669          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 669
ctgtatcagt                                                              10

SEQ ID NO: 670          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 670
acataatgag                                                              10

SEQ ID NO: 671          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 671
agccttccgc                                                              10

SEQ ID NO: 672          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 672
cagtgctttt                                                              10

SEQ ID NO: 673          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 673
tagtccgtgt                                                              10

SEQ ID NO: 674          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 674
cggaatcggt                                                              10

SEQ ID NO: 675          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 675
cttgcggaga                                                              10
```

```
SEQ ID NO: 676          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 676
aaaaatttgg                                                            10

SEQ ID NO: 677          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 677
tgttttccgc                                                            10

SEQ ID NO: 678          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 678
atgctaggcg                                                            10

SEQ ID NO: 679          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 679
gactaatttc                                                            10

SEQ ID NO: 680          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 680
ctgtagtaac                                                            10

SEQ ID NO: 681          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 681
cggatgactt                                                            10

SEQ ID NO: 682          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 682
tcagagtgga                                                            10

SEQ ID NO: 683          moltype = DNA  length = 10
```

-continued

```
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 683
caaaatagcg                                                            10

SEQ ID NO: 684         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 684
gaagaagaag                                                            10

SEQ ID NO: 685         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 685
cacccgcacg                                                            10

SEQ ID NO: 686         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 686
acgatgcccg                                                            10

SEQ ID NO: 687         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 687
cctactacac                                                            10

SEQ ID NO: 688         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 688
attgaaacaa                                                            10

SEQ ID NO: 689         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 689
gaccgaagat                                                            10

SEQ ID NO: 690         moltype = DNA  length = 10
FEATURE                Location/Qualifiers
misc_feature           1..10
```

```
                      note = Description of Artificial Sequence: Synthetic
                       oligonucleotide
source                1..10
                      mol_type = other DNA
                      organism = synthetic construct
SEQUENCE: 690
acggcctgaa                                                            10

SEQ ID NO: 691        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 691
aggggaggtc                                                            10

SEQ ID NO: 692        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 692
caatcaactt                                                            10

SEQ ID NO: 693        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 693
ggacaaccga                                                            10

SEQ ID NO: 694        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 694
tccctaaggc                                                            10

SEQ ID NO: 695        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 695
gttctacacg                                                            10

SEQ ID NO: 696        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 696
actaaccagt                                                            10

SEQ ID NO: 697        moltype = DNA  length = 10
FEATURE               Location/Qualifiers
misc_feature          1..10
                      note = Description of Artificial Sequence: Synthetic
                       oligonucleotide
```

```
source                  1..10
                        mol_type = other DNA
                        organism = synthetic construct
SEQUENCE: 697
gaagctggat                                                              10

SEQ ID NO: 698          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 698
ggaaccatgg                                                              10

SEQ ID NO: 699          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 699
ctctacctgg                                                              10

SEQ ID NO: 700          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 700
taatgcctgc                                                              10

SEQ ID NO: 701          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 701
taaaggcaat                                                              10

SEQ ID NO: 702          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 702
cgcctgggaa                                                              10

SEQ ID NO: 703          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 703
tcttggggaa                                                              10

SEQ ID NO: 704          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

```
                         organism = synthetic construct
SEQUENCE: 704
agagagagag                                                              10

SEQ ID NO: 705           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 705
gcgttggcgc                                                              10

SEQ ID NO: 706           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 706
ttacgacaga                                                              10

SEQ ID NO: 707           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 707
ggaactctta                                                              10

SEQ ID NO: 708           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 708
gattgtggag                                                              10

SEQ ID NO: 709           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 709
gggcactgat                                                              10

SEQ ID NO: 710           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 710
agacgcacca                                                              10

SEQ ID NO: 711           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 711
```

```
ccaattataa                                                          10

SEQ ID NO: 712          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 712
tagagacgca                                                          10

SEQ ID NO: 713          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 713
cctcttgtcg                                                          10

SEQ ID NO: 714          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 714
gaggaagctc                                                          10

SEQ ID NO: 715          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 715
agtcccgagt                                                          10

SEQ ID NO: 716          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 716
tgcttgcagt                                                          10

SEQ ID NO: 717          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 717
cccacttccc                                                          10

SEQ ID NO: 718          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 718
cgttgccgcg                                                          10
```

```
SEQ ID NO: 719          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 719
cccctggttc                                                          10

SEQ ID NO: 720          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 720
acgaccaata                                                          10

SEQ ID NO: 721          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 721
cttagggttc                                                          10

SEQ ID NO: 722          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 722
aaacatatca                                                          10

SEQ ID NO: 723          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 723
gggtcgtaga                                                          10

SEQ ID NO: 724          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 724
ctccgtagcg                                                          10

SEQ ID NO: 725          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 725
ctggtcataa                                                          10

SEQ ID NO: 726          moltype = DNA  length = 10
FEATURE                 Location/Qualifiers
```

```
misc_feature            1..10
                        note = Description of Artificial Sequence: Synthetic
                         oligonucleotide
source                  1..10
                        mol_type = other DNA
                        organism = synthetic construct
SEQUENCE: 726
ttgacagatc                                                                10

SEQ ID NO: 727          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 727
gagtaaagtc                                                                10

SEQ ID NO: 728          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 728
atatgggctt                                                                10

SEQ ID NO: 729          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 729
tacaactact                                                                10

SEQ ID NO: 730          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 730
aattcagccg                                                                10

SEQ ID NO: 731          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 731
gattgtacta                                                                10

SEQ ID NO: 732          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 732
tcgtaatgcg                                                                10

SEQ ID NO: 733          moltype = DNA  length = 10
FEATURE                 Location/Qualifiers
misc_feature            1..10
                        note = Description of Artificial Sequence: Synthetic
```

```
                        oligonucleotide
source                  1..10
                        mol_type = other DNA
                        organism = synthetic construct
SEQUENCE: 733
cgataactgc                                                   10

SEQ ID NO: 734          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 734
aacttggcgg                                                   10

SEQ ID NO: 735          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 735
cgtggatgta                                                   10

SEQ ID NO: 736          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 736
ccttcccgaa                                                   10

SEQ ID NO: 737          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 737
ctaaacccgt                                                   10

SEQ ID NO: 738          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 738
caacattccc                                                   10

SEQ ID NO: 739          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 739
cttaccctct                                                   10

SEQ ID NO: 740          moltype = DNA  length = 10
FEATURE                 Location/Qualifiers
misc_feature            1..10
                        note = Description of Artificial Sequence: Synthetic
                         oligonucleotide
source                  1..10
```

```
                         mol_type = other DNA
                         organism = synthetic construct
SEQUENCE: 740
ggaaagttct                                                         10

SEQ ID NO: 741           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 741
cggattggct                                                         10

SEQ ID NO: 742           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 742
aatgtagggc                                                         10

SEQ ID NO: 743           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 743
aatgaatcgc                                                         10

SEQ ID NO: 744           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 744
atcatacacc                                                         10

SEQ ID NO: 745           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 745
agttgggcag                                                         10

SEQ ID NO: 746           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 746
agaagaaggg                                                         10

SEQ ID NO: 747           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
```

```
SEQUENCE: 747
gcgtgcgcta                                                        10

SEQ ID NO: 748         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 748
ccccgataaa                                                        10

SEQ ID NO: 749         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 749
taccaagtgc                                                        10

SEQ ID NO: 750         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 750
tgtgttttcg                                                        10

SEQ ID NO: 751         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 751
cccagatgtc                                                        10

SEQ ID NO: 752         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 752
gcgagcttcc                                                        10

SEQ ID NO: 753         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 753
gtgtcacgta                                                        10

SEQ ID NO: 754         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 754
ataggccgag                                                        10
```

```
SEQ ID NO: 755          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 755
gagctaccag                                                            10

SEQ ID NO: 756          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 756
cgcggcggag                                                            10

SEQ ID NO: 757          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 757
tcttgcacga                                                            10

SEQ ID NO: 758          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 758
tgccctaaag                                                            10

SEQ ID NO: 759          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 759
ttgcgctttg                                                            10

SEQ ID NO: 760          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 760
catataaagg                                                            10

SEQ ID NO: 761          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 761
aatagcgaat                                                            10

SEQ ID NO: 762          moltype = DNA  length = 10
```

-continued

```
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 762
tacgctaagg                                                                 10

SEQ ID NO: 763         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 763
acttagttcg                                                                 10

SEQ ID NO: 764         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 764
cgtgcggaac                                                                 10

SEQ ID NO: 765         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 765
acccgattcg                                                                 10

SEQ ID NO: 766         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 766
tgcagagttt                                                                 10

SEQ ID NO: 767         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 767
gaatcattag                                                                 10

SEQ ID NO: 768         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 768
agtacactgg                                                                 10

SEQ ID NO: 769         moltype = DNA  length = 10
FEATURE                Location/Qualifiers
misc_feature           1..10
```

```
                        note = Description of Artificial Sequence: Synthetic
                         oligonucleotide
source                  1..10
                        mol_type = other DNA
                        organism = synthetic construct
SEQUENCE: 769
ttgtgcggtt                                                                   10

SEQ ID NO: 770          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 770
atgacatgca                                                                   10

SEQ ID NO: 771          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 771
ttctcggacg                                                                   10

SEQ ID NO: 772          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 772
agattgaaga                                                                   10

SEQ ID NO: 773          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 773
ggcggactgt                                                                   10

SEQ ID NO: 774          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 774
tttatggtaa                                                                   10

SEQ ID NO: 775          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 775
cagtagggtg                                                                   10

SEQ ID NO: 776          moltype = DNA  length = 10
FEATURE                 Location/Qualifiers
misc_feature            1..10
                        note = Description of Artificial Sequence: Synthetic
                         oligonucleotide
```

-continued

```
source                  1..10
                        mol_type = other DNA
                        organism = synthetic construct
SEQUENCE: 776
gacaggcaag                                                              10

SEQ ID NO: 777          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 777
gatgtgtcgt                                                              10

SEQ ID NO: 778          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 778
acttgacgga                                                              10

SEQ ID NO: 779          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 779
aagtccgaaa                                                              10

SEQ ID NO: 780          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 780
tgggtgtagg                                                              10

SEQ ID NO: 781          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 781
acttaccgcg                                                              10

SEQ ID NO: 782          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 782
ctgtgcaccc                                                              10

SEQ ID NO: 783          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

```
                         organism = synthetic construct
SEQUENCE: 783
attgctctct                                                                10

SEQ ID NO: 784           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 784
cagaagacaa                                                                10

SEQ ID NO: 785           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 785
ttacgctata                                                                10

SEQ ID NO: 786           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 786
acgtggaaat                                                                10

SEQ ID NO: 787           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 787
tgaggctggt                                                                10

SEQ ID NO: 788           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 788
attatgagat                                                                10

SEQ ID NO: 789           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 789
gacttgtagt                                                                10

SEQ ID NO: 790           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 790
```

```
tcgctgagga                                                            10

SEQ ID NO: 791          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 791
cccaactcta                                                            10

SEQ ID NO: 792          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 792
gatagggagg                                                            10

SEQ ID NO: 793          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 793
tagaaatcag                                                            10

SEQ ID NO: 794          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 794
gtcgctagaa                                                            10

SEQ ID NO: 795          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 795
aaaatagaaa                                                            10

SEQ ID NO: 796          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 796
gctcctgggt                                                            10

SEQ ID NO: 797          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 797
cgcgctcgcg                                                            10
```

```
SEQ ID NO: 798          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 798
ggcaaacgca                                                            10

SEQ ID NO: 799          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 799
tttactacct                                                            10

SEQ ID NO: 800          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 800
atcctaaact                                                            10

SEQ ID NO: 801          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 801
ctccgtatgt                                                            10

SEQ ID NO: 802          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 802
tatcgtccag                                                            10

SEQ ID NO: 803          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 803
gccggcggta                                                            10

SEQ ID NO: 804          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 804
tgctccattt                                                            10

SEQ ID NO: 805          moltype = DNA  length = 10
FEATURE                 Location/Qualifiers
```

```
misc_feature            1..10
                        note = Description of Artificial Sequence: Synthetic
                         oligonucleotide
source                  1..10
                        mol_type = other DNA
                        organism = synthetic construct
SEQUENCE: 805
tggctgttgt                                                            10

SEQ ID NO: 806          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 806
tactgcgcaa                                                            10

SEQ ID NO: 807          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 807
tatacggctt                                                            10

SEQ ID NO: 808          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 808
ggttattacc                                                            10

SEQ ID NO: 809          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 809
atcaggagga                                                            10

SEQ ID NO: 810          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 810
ctattgccag                                                            10

SEQ ID NO: 811          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 811
acgtacacac                                                            10

SEQ ID NO: 812          moltype = DNA  length = 10
FEATURE                 Location/Qualifiers
misc_feature            1..10
                        note = Description of Artificial Sequence: Synthetic
```

```
                        oligonucleotide
source                  1..10
                        mol_type = other DNA
                        organism = synthetic construct
SEQUENCE: 812
cagcctagct                                                            10

SEQ ID NO: 813          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 813
gaaaaacaac                                                            10

SEQ ID NO: 814          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 814
cgttcagtta                                                            10

SEQ ID NO: 815          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 815
caatcagaat                                                            10

SEQ ID NO: 816          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 816
gggctactct                                                            10

SEQ ID NO: 817          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 817
ccccattggg                                                            10

SEQ ID NO: 818          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 818
tagggaacgg                                                            10

SEQ ID NO: 819          moltype = DNA  length = 10
FEATURE                 Location/Qualifiers
misc_feature            1..10
                        note = Description of Artificial Sequence: Synthetic
                         oligonucleotide
source                  1..10
```

```
                        mol_type = other DNA
                        organism = synthetic construct
SEQUENCE: 819
cagctgatac                                                   10

SEQ ID NO: 820          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 820
attcctgtga                                                   10

SEQ ID NO: 821          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 821
tcagagccgt                                                   10

SEQ ID NO: 822          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 822
catgaaaagc                                                   10

SEQ ID NO: 823          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 823
tgacctgtga                                                   10

SEQ ID NO: 824          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 824
gcattagcag                                                   10

SEQ ID NO: 825          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 825
gacagaacca                                                   10

SEQ ID NO: 826          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
```

```
SEQUENCE: 826
tccagtatat                                                            10

SEQ ID NO: 827          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 827
tgttccgcta                                                            10

SEQ ID NO: 828          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 828
gatatccatt                                                            10

SEQ ID NO: 829          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 829
catatggacc                                                            10

SEQ ID NO: 830          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 830
gatatagtaa                                                            10

SEQ ID NO: 831          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 831
cacctttttt                                                            10

SEQ ID NO: 832          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 832
agcttgcggg                                                            10

SEQ ID NO: 833          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 833
cgcacaggga                                                            10
```

```
SEQ ID NO: 834          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 834
tctgggtgct                                                          10

SEQ ID NO: 835          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 835
tgagtcgttt                                                          10

SEQ ID NO: 836          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 836
ttacaatgtg                                                          10

SEQ ID NO: 837          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 837
cttgcaaaca                                                          10

SEQ ID NO: 838          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 838
tgtcgagctg                                                          10

SEQ ID NO: 839          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 839
actttaacct                                                          10

SEQ ID NO: 840          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 840
atataagtgc                                                          10

SEQ ID NO: 841          moltype = DNA  length = 10
```

-continued

```
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 841
ggaagggcgt                                                            10

SEQ ID NO: 842          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 842
tttgacttga                                                            10

SEQ ID NO: 843          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 843
gtataaacgg                                                            10

SEQ ID NO: 844          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 844
taaccggatg                                                            10

SEQ ID NO: 845          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 845
ttctcatcag                                                            10

SEQ ID NO: 846          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 846
ctcggttacg                                                            10

SEQ ID NO: 847          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 847
atatggttct                                                            10

SEQ ID NO: 848          moltype = DNA  length = 10
FEATURE                 Location/Qualifiers
misc_feature            1..10
```

```
                        note = Description of Artificial Sequence: Synthetic
                         oligonucleotide
source                  1..10
                        mol_type = other DNA
                        organism = synthetic construct
SEQUENCE: 848
cgcccccgaa                                                                  10

SEQ ID NO: 849          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 849
acctcgatcg                                                                  10

SEQ ID NO: 850          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 850
ctcgaataat                                                                  10

SEQ ID NO: 851          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 851
gcccgagctt                                                                  10

SEQ ID NO: 852          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 852
aacagtcaac                                                                  10

SEQ ID NO: 853          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 853
ctggaacctc                                                                  10

SEQ ID NO: 854          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 854
aataacgggg                                                                  10

SEQ ID NO: 855          moltype = DNA  length = 10
FEATURE                 Location/Qualifiers
misc_feature            1..10
                        note = Description of Artificial Sequence: Synthetic
                         oligonucleotide
```

```
source                  1..10
                        mol_type = other DNA
                        organism = synthetic construct
SEQUENCE: 855
acgccccact                                                             10

SEQ ID NO: 856          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 856
ggcaacatga                                                             10

SEQ ID NO: 857          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 857
gctatttcgc                                                             10

SEQ ID NO: 858          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 858
ttccacttta                                                             10

SEQ ID NO: 859          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 859
gccgatggat                                                             10

SEQ ID NO: 860          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 860
aagttggtaa                                                             10

SEQ ID NO: 861          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 861
cactagctag                                                             10

SEQ ID NO: 862          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

```
                        organism = synthetic construct
SEQUENCE: 862
acatgcccct                                                                10

SEQ ID NO: 863          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 863
ttcattactc                                                                10

SEQ ID NO: 864          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 864
ggtttaatat                                                                10

SEQ ID NO: 865          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 865
cctgcagtga                                                                10

SEQ ID NO: 866          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 866
tctttaagtt                                                                10

SEQ ID NO: 867          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 867
tggcgatcga                                                                10

SEQ ID NO: 868          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 868
ctttttagct                                                                10

SEQ ID NO: 869          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 869
```

```
cccagtctct                                                            10

SEQ ID NO: 870          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 870
aaatgtttcg                                                            10

SEQ ID NO: 871          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 871
atataagacg                                                            10

SEQ ID NO: 872          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 872
tcactttaca                                                            10

SEQ ID NO: 873          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 873
cctggcgccc                                                            10

SEQ ID NO: 874          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 874
ggattactgg                                                            10

SEQ ID NO: 875          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 875
gaatgatctt                                                            10

SEQ ID NO: 876          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 876
gctcggatcg                                                            10
```

```
SEQ ID NO: 877          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 877
cagctgcgag                                                                10

SEQ ID NO: 878          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 878
acccttacta                                                                10

SEQ ID NO: 879          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 879
aggtgaaact                                                                10

SEQ ID NO: 880          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 880
cgaatttgat                                                                10

SEQ ID NO: 881          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 881
cgctgtgcgg                                                                10

SEQ ID NO: 882          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 882
ttaccgcacc                                                                10

SEQ ID NO: 883          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 883
ggaatcttaa                                                                10

SEQ ID NO: 884          moltype = DNA  length = 10
FEATURE                 Location/Qualifiers
```

```
misc_feature            1..10
                        note = Description of Artificial Sequence: Synthetic
                         oligonucleotide
source                  1..10
                        mol_type = other DNA
                        organism = synthetic construct
SEQUENCE: 884
ctcaacaccc                                                   10

SEQ ID NO: 885          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 885
cgtgcccttg                                                   10

SEQ ID NO: 886          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 886
gcaggctcga                                                   10

SEQ ID NO: 887          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 887
accaacgaag                                                   10

SEQ ID NO: 888          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 888
cctgtaattt                                                   10

SEQ ID NO: 889          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 889
gggtgggatg                                                   10

SEQ ID NO: 890          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 890
ttgctcaccg                                                   10

SEQ ID NO: 891          moltype = DNA  length = 10
FEATURE                 Location/Qualifiers
misc_feature            1..10
                        note = Description of Artificial Sequence: Synthetic
```

```
                         oligonucleotide
source                  1..10
                        mol_type = other DNA
                        organism = synthetic construct
SEQUENCE: 891
ttacgaccac                                                            10

SEQ ID NO: 892          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 892
ttttctaacc                                                            10

SEQ ID NO: 893          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 893
gctttagata                                                            10

SEQ ID NO: 894          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 894
cacgtattgg                                                            10

SEQ ID NO: 895          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 895
aaatatctcc                                                            10

SEQ ID NO: 896          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 896
gctggaaaac                                                            10

SEQ ID NO: 897          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 897
gagcgcatta                                                            10

SEQ ID NO: 898          moltype = DNA  length = 10
FEATURE                 Location/Qualifiers
misc_feature            1..10
                        note = Description of Artificial Sequence: Synthetic
                         oligonucleotide
source                  1..10
```

```
                        mol_type = other DNA
                        organism = synthetic construct
SEQUENCE: 898
gtggaggggt                                                          10

SEQ ID NO: 899          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 899
tccactggga                                                          10

SEQ ID NO: 900          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 900
caatagcgga                                                          10

SEQ ID NO: 901          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 901
catctagttt                                                          10

SEQ ID NO: 902          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 902
gaagttccgg                                                          10

SEQ ID NO: 903          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 903
agcgagattc                                                          10

SEQ ID NO: 904          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 904
ttaaggtcgg                                                          10

SEQ ID NO: 905          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
```

```
SEQUENCE: 905
aatggttagg                                                    10

SEQ ID NO: 906          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 906
cgttattata                                                    10

SEQ ID NO: 907          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 907
acggaaagga                                                    10

SEQ ID NO: 908          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 908
ccttgtcccg                                                    10

SEQ ID NO: 909          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 909
atactttttt                                                    10

SEQ ID NO: 910          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 910
ctgggtctgg                                                    10

SEQ ID NO: 911          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 911
aaccattgcg                                                    10

SEQ ID NO: 912          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 912
agaccgggcc                                                    10
```

```
SEQ ID NO: 913          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 913
tgggacacac                                                            10

SEQ ID NO: 914          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 914
tgcgcagttg                                                            10

SEQ ID NO: 915          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 915
cgttcgcctt                                                            10

SEQ ID NO: 916          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 916
tctcactcgt                                                            10

SEQ ID NO: 917          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 917
acaccgacgt                                                            10

SEQ ID NO: 918          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 918
ttcagcccct                                                            10

SEQ ID NO: 919          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 919
aggcgactaa                                                            10

SEQ ID NO: 920          moltype = DNA  length = 10
```

```
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 920
tgctatcaag                                                              10

SEQ ID NO: 921          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 921
gtccagtagc                                                              10

SEQ ID NO: 922          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 922
cgtgtgggcg                                                              10

SEQ ID NO: 923          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 923
gtggttctcc                                                              10

SEQ ID NO: 924          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 924
gcagccgacg                                                              10

SEQ ID NO: 925          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 925
gctgtccacg                                                              10

SEQ ID NO: 926          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 926
cgacactcat                                                              10

SEQ ID NO: 927          moltype = DNA  length = 10
FEATURE                 Location/Qualifiers
misc_feature            1..10
```

```
                        note = Description of Artificial Sequence: Synthetic
                         oligonucleotide
source                  1..10
                        mol_type = other DNA
                        organism = synthetic construct
SEQUENCE: 927
catggcacct                                                                10

SEQ ID NO: 928          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 928
tgtgacgtgt                                                                10

SEQ ID NO: 929          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 929
tttggactaa                                                                10

SEQ ID NO: 930          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 930
ttcatgcccg                                                                10

SEQ ID NO: 931          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 931
ttgatcgtgg                                                                10

SEQ ID NO: 932          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 932
tagcatagga                                                                10

SEQ ID NO: 933          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 933
gtagttgcaa                                                                10

SEQ ID NO: 934          moltype = DNA  length = 10
FEATURE                 Location/Qualifiers
misc_feature            1..10
                        note = Description of Artificial Sequence: Synthetic
                         oligonucleotide
```

-continued

```
source                1..10
                      mol_type = other DNA
                      organism = synthetic construct
SEQUENCE: 934
gggacagcta                                                        10

SEQ ID NO: 935        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 935
aaacccccaa                                                        10

SEQ ID NO: 936        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 936
actctcacaa                                                        10

SEQ ID NO: 937        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 937
atcattgcca                                                        10

SEQ ID NO: 938        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 938
ccagtttgcg                                                        10

SEQ ID NO: 939        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 939
acattagtca                                                        10

SEQ ID NO: 940        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
                      organism = synthetic construct
SEQUENCE: 940
ctccagggta                                                        10

SEQ ID NO: 941        moltype = DNA  length = 10
FEATURE               Location/Qualifiers
misc_feature          1..10
                      note = Description of Artificial Sequence: Synthetic
                       oligonucleotide
source                1..10
                      mol_type = other DNA
```

```
                        organism = synthetic construct
SEQUENCE: 941
gaagggccaa                                                                10

SEQ ID NO: 942          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 942
cagtctcccc                                                                10

SEQ ID NO: 943          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 943
gagacattcc                                                                10

SEQ ID NO: 944          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 944
aacggtgttg                                                                10

SEQ ID NO: 945          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 945
agcattatca                                                                10

SEQ ID NO: 946          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 946
ctataccgag                                                                10

SEQ ID NO: 947          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 947
aactggatca                                                                10

SEQ ID NO: 948          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 948
```

```
gtcttgtcgg                                                  10

SEQ ID NO: 949         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 949
gacgagccgc                                                  10

SEQ ID NO: 950         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 950
ggaacactgt                                                  10

SEQ ID NO: 951         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 951
taaatgcgtt                                                  10

SEQ ID NO: 952         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 952
gcgaacacag                                                  10

SEQ ID NO: 953         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 953
ttctctcaac                                                  10

SEQ ID NO: 954         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 954
gtcgtactga                                                  10

SEQ ID NO: 955         moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 955
tgtggcgtaa                                                  10
```

```
SEQ ID NO: 956          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 956
tgagcggcgt                                                            10

SEQ ID NO: 957          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 957
cctcgtgaac                                                            10

SEQ ID NO: 958          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 958
gagcaatgaa                                                            10

SEQ ID NO: 959          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 959
cgagacctaa                                                            10

SEQ ID NO: 960          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 960
aactgagcgc                                                            10

SEQ ID NO: 961          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 961
taaagctcgt                                                            10

SEQ ID NO: 962          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 962
ctctttacgt                                                            10

SEQ ID NO: 963          moltype = DNA  length = 10
FEATURE                 Location/Qualifiers
```

```
misc_feature            1..10
                        note = Description of Artificial Sequence: Synthetic
                         oligonucleotide
source                  1..10
                        mol_type = other DNA
                        organism = synthetic construct
SEQUENCE: 963
ccccgtggaa                                                                  10

SEQ ID NO: 964          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 964
tcggttcgtc                                                                  10

SEQ ID NO: 965          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 965
ctgcttacac                                                                  10

SEQ ID NO: 966          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 966
acaccgtaat                                                                  10

SEQ ID NO: 967          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 967
cctggtcggc                                                                  10

SEQ ID NO: 968          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 968
ggttatttgg                                                                  10

SEQ ID NO: 969          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 969
gcaactgagt                                                                  10

SEQ ID NO: 970          moltype = DNA  length = 10
FEATURE                 Location/Qualifiers
misc_feature            1..10
                        note = Description of Artificial Sequence: Synthetic
```

```
                         oligonucleotide
source                  1..10
                        mol_type = other DNA
                        organism = synthetic construct
SEQUENCE: 970
ataaggcctc                                                         10

SEQ ID NO: 971          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 971
cgtgcgaagg                                                         10

SEQ ID NO: 972          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 972
gtcacacact                                                         10

SEQ ID NO: 973          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 973
catacggcaa                                                         10

SEQ ID NO: 974          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 974
gaactgccca                                                         10

SEQ ID NO: 975          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 975
aatatgtgaa                                                         10

SEQ ID NO: 976          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 976
ccgatcctgt                                                         10

SEQ ID NO: 977          moltype = DNA  length = 10
FEATURE                 Location/Qualifiers
misc_feature            1..10
                        note = Description of Artificial Sequence: Synthetic
                         oligonucleotide
source                  1..10
```

```
                        mol_type = other DNA
                        organism = synthetic construct
SEQUENCE: 977
caaagagcct                                                        10

SEQ ID NO: 978          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 978
taacttagag                                                        10

SEQ ID NO: 979          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 979
cagcatgtag                                                        10

SEQ ID NO: 980          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 980
ccccatgcag                                                        10

SEQ ID NO: 981          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 981
tctgaaccac                                                        10

SEQ ID NO: 982          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 982
gcgtgcaaaa                                                        10

SEQ ID NO: 983          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 983
gctagtaccg                                                        10

SEQ ID NO: 984          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
```

```
SEQUENCE: 984
tttcccgcgc                                                        10

SEQ ID NO: 985          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 985
ccttagtagg                                                        10

SEQ ID NO: 986          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 986
ttgtgtcttg                                                        10

SEQ ID NO: 987          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 987
gcaacgaagc                                                        10

SEQ ID NO: 988          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 988
tgaaaccctt                                                        10

SEQ ID NO: 989          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 989
ttctacgatc                                                        10

SEQ ID NO: 990          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 990
attaaaggtg                                                        10

SEQ ID NO: 991          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 991
tatctaacgg                                                        10
```

```
SEQ ID NO: 992          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 992
agtgctcctg                                                            10

SEQ ID NO: 993          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 993
ccgtccctct                                                            10

SEQ ID NO: 994          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 994
ctaacgagcg                                                            10

SEQ ID NO: 995          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 995
aagtccggct                                                            10

SEQ ID NO: 996          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 996
ggcgtataag                                                            10

SEQ ID NO: 997          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 997
agatattagg                                                            10

SEQ ID NO: 998          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 998
tcctaacagc                                                            10

SEQ ID NO: 999          moltype = DNA  length = 10
```

-continued

```
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 999
gaggatacgc                                                            10

SEQ ID NO: 1000          moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
                         organism = synthetic construct
SEQUENCE: 1000
cgctctttaa                                                            10

SEQ ID NO: 1001          moltype = DNA  length = 21
FEATURE                  Location/Qualifiers
misc_feature             1..21
                         note = Description of Artificial Sequence: Synthetic
                          oligonucleotide
source                   1..21
                         mol_type = other DNA
                         organism = synthetic construct
SEQUENCE: 1001
agacgtgtgc tcttccgatc t                                               21

SEQ ID NO: 1002          moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 1002
agatcggaag agcgtcgtgt                                                 20

SEQ ID NO: 1003          moltype = DNA  length = 61
FEATURE                  Location/Qualifiers
misc_feature             1..61
                         note = Description of Artificial Sequence: Synthetic
                          oligonucleotide
misc_difference          32..41
                         note = a, c, t, g, unknown or other
misc_feature             32..41
                         note = This region represents the random sequence fragment
source                   1..61
                         mol_type = other DNA
                         organism = synthetic construct
SEQUENCE: 1003
agacgtgtgc tcttccgatc tgctacataa tnnnnnnnnn nagatcggaa gagcgtcgtg  60
t                                                                     61
```